US009636379B2

(12) United States Patent
Chen et al.

(10) Patent No.: US 9,636,379 B2
(45) Date of Patent: *May 2, 2017

(54) COMPOSITIONS AND METHODS FOR TREATING PRURITUS

(71) Applicant: Washington University, St. Louis, MO (US)

(72) Inventors: Zhou-feng Chen, St. Louis, MO (US); Yan-gang Sun, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,545

(22) Filed: Dec. 22, 2014

(65) Prior Publication Data

US 2015/0250849 A1 Sep. 10, 2015

Related U.S. Application Data

(63) Continuation of application No. 12/740,819, filed as application No. PCT/US2008/082267 on Nov. 3, 2008, now Pat. No. 9,044,510.

(60) Provisional application No. 60/984,532, filed on Nov. 1, 2007, provisional application No. 61/023,478, filed on Jan. 25, 2008.

(51) Int. Cl.
| *A01N 37/18* | (2006.01) |
| *A61K 38/00* | (2006.01) |
| *A61K 45/06* | (2006.01) |
| *A61K 9/00* | (2006.01) |
| *A61K 31/00* | (2006.01) |
| *A61K 31/485* | (2006.01) |
| *A61K 38/16* | (2006.01) |
| *A61K 38/10* | (2006.01) |
| *A61K 31/713* | (2006.01) |
| *A61K 47/10* | (2017.01) |
| *A61K 47/44* | (2017.01) |

(52) U.S. Cl.
CPC .......... *A61K 38/105* (2013.01); *A61K 9/0019* (2013.01); *A61K 31/00* (2013.01); *A61K 31/485* (2013.01); *A61K 31/713* (2013.01); *A61K 38/168* (2013.01); *A61K 45/06* (2013.01); *A61K 47/10* (2013.01); *A61K 47/44* (2013.01)

(58) Field of Classification Search
None
See application file for complete search history.

(56) References Cited

U.S. PATENT DOCUMENTS

| 5,521,183 | A | 5/1996 | Woodward et al. |
| 6,136,839 | A | 10/2000 | Isakson et al. |
| 6,375,957 | B1 | 4/2002 | Kaiko et al. |
| 6,475,494 | B2 | 11/2002 | Kaiko et al. |
| 6,696,066 | B2 | 2/2004 | Kaiko et al. |
| 6,982,283 | B2 | 1/2006 | Ueno |
| 8,957,024 | B2 * | 2/2015 | Chen .................... A61K 38/177 514/18.4 |
| 9,044,510 | B2 * | 6/2015 | Chen .................... A61K 9/0019 |
| 2003/0054030 | A1 | 3/2003 | Gordon |
| 2003/0100057 | A1 | 5/2003 | Feder et al. |
| 2004/0116440 | A1 | 6/2004 | Higginbottom et al. |
| 2007/0225209 | A1 | 9/2007 | Roch et al. |
| 2013/0065832 | A1 | 3/2013 | Chen et al. |

FOREIGN PATENT DOCUMENTS

WO 2005023284 A1 3/2005

OTHER PUBLICATIONS

Bhattacherjee, Laser capture microdissection of fluorescently labeled embryonic cranial neural crest cells, Genesis, 2004, pp. 58-64, vol. 39.
Carroll, The burden of atopic dermatitis: impact on the patient, family, and society, Pediatr Dermatol, 2005, pp. 192-199, vol. 22.
Gong, A gene expression atlas of the central nervous system based on bacterial artificial chromosomes, Nature, 2003, pp. 917-925, vol. 425.
Green, Influence of genotype, dose and sex on pruritogen-induced scratching behavior in the mouse, Pain, 2006, pp. 50-58, vol. 124.
Ikoma, The neurobiology of itch, Nat Rev Neurosci, 2006, pp. 535-547, vol. 7.
Inan, Kappa opioid agonists suppress chloroquine-induced scratching in mice, Eur J Pharmacol, 2004, pp. 233-237, vol. 502.
Kuraishi, Scratching behavior induced by pruritogenic but not algesiogenic agents in mice, Eur J Pharmacol, 1995, pp. 229-233, vol. 275.
Malmberg, Partial sciatic nerve injury in the mouse as a model of neuropathic pain: behavioral and neuroanatomical correlates, Pain, 1998, pp. 215-222, vol. 76.
Ohki-Hamazaki, Mice lacking bombesin receptor subtype-3 develop metabolic defects and obesity, Nature, 1997, pp. 165-169, vol. 390.
Schmelz, A neural pathway for itch, Nat Neurosci, 2001, pp. 4-10, vol. 4.
Shimada, Scratching behavior in mice induced by the proteinase-activated receptor-2 agonist, SLIGRL-NH2, Eur J Pharmacol, 2006, pp. 281-283, vol. 530.
Sun, A gastrin-releasing peptide receptor mediates the itch sensation in the spinal cord, Nature, 2007, pp. 700-703, vol. 448.
Tominaga, Thermosensation and pain, J Neurobiol, 2004, pp. 3-12, vol. 61.
Birren, Sympathetic neuroblasts undergo a developmental switch in trophic dependence, Development, 1993, pp. 597-610, vol. 119.
Buys, Treatment options for atopic dermatitis, Am Fam Physician, 2007, pp. 523-528, vol. 75.
Davidson, The itch-producing agents histamine and cowhage activate separate populations of primate spinothalamic tract neurons, J Neurosci, 2007, pp. 10007-10014, vol. 27.
Flohr, How atopic is atopic dermatitis? J Allergy Clin Immunol, 2004, pp. 150-158, vol. 114.

(Continued)

*Primary Examiner* — Olga N Chernyshev
(74) *Attorney, Agent, or Firm* — Polsinelli PC

(57) ABSTRACT

The present invention encompasses methods and compositions for alleviating pruritus. The compositions may comprise an analgesic agent.

9 Claims, 77 Drawing Sheets
(21 of 77 Drawing Sheet(s) Filed in Color)

(56) References Cited

OTHER PUBLICATIONS

[Book] Goodman & Gilman, The Pharmacological Basis of Therapeutics pp. 617-657 9th ed, 1996.
[Book] Goodman & Gilman, The Pharmacological Basis of Therapeutics pp. 617-657 10th ed, 2001, Appendix II, pp. 475-493.
[Book] Insel P, Analgesic-Antipyretic and Anti-inflammatory Agents and Drugs Employed in the Treatment of Gout.
Jain, Ret is dispensable for maintenance of midbrain dopaminergic neurons in adult mice, J Neurosci, 2006, pp. 11230-11238, vol. 26.
Li, Molecular mapping of developing dorsal horn-enriched genes by microarray and dorsal/ventral subtractive screening, Dev Biol, 2006, pp. 555-564, vol. 292.
Li, Model-based analysis of oligonucleotide arrays: expression index computation and outlier detection, Proc Natl Acad Sci U S A, 2001, pp. 31-36, vol. 98.
Maekawa, (2000) Itch-associated responses of afferent nerve innervating the murine skin: different effects of histamine and serotonin in ICR and ddY mice, Jpn J Pharmacol, Dec. 2000, pp. 462-466, vol. 84(4).
Mantey, Discovery of a high affinity radioligand for the human orphan receptor, bombesin receptor subtype 3, which demonstrates that it has a unique pharmacology compared with other mammalian bombesin receptors, J Biol Chem, 1997, pp. 26062-26071, vol. 272.
[Book] Remington, The Science and Practice of Pharmacy, vol. II, pp. 1196-1221, 19th ed. 1995.
Ryan, Ability of various bombesin receptor agonists and antagonists to alter intracellular signaling of the human orphan receptor BRS-3, J Biol Chem, 1998, pp. 13613-13624, vol. 273.
Abbadie, C. et al., "Comparative Immunohistochemical Distributions of Carboxy Terminus Epitopes From the Mu-Opioid Receptor Splice Variants MOR-1D, MOR-1 and MOR-1C in the Mouse and Rat CNS," Neurosci., 2000, pp. 141-153, vol. 100, No. 1.
Agnati, L. et al., "Molecular Mechanisms and Therapeutical Implications of Intramembrane Receptor/Receptor Interactions among Heptahelical Receptors with Examples from the Striatopallidal GABA Neurons," Pharmacol. Rev., 2003, pp. 509-550, vol. 55, No. 3.
Alvarez, V. et al., "µ-Opioid Receptors: Ligand-Dependent Activation of Potassium Conductance, Desensitization, and Internalization," J. Neurosci., Jul. 1, 2002, pp. 5769-5776, vol. 22, No. 13.
Andoh, T. et al., "Evidence for Separate Involvement of Different µ-Opioid Receptor Subtypes in Itch and Analgesia Induced by Supraspinal Action of Opioids," J. Pharmacol. Sci., 2008, pp. 667-670, vol. 106, No. 4.
Ballantyne, J. et al., "Itching after epidural and spinal opiates," Pain, 1988, pp. 149-160, vol. 33, No. 2.
Berendsen, H., "A glimpse of the Holy Grail?," Science, Oct. 23, 1998, pp. 642-643, vol. 282, No. 5389.
Bergasa, N., "The pruritus of cholestasis," J. Hepatol., 2005, pp. 1078-1088, vol. 43, No. 6.
Bouvier, M., "Oligomerization of G-Protein-Coupled Transmitter Receptors," Nat. Rev. Neurosci., Apr. 2001, pp. 274-286, vol. 2, No. 4.
Bradley, C. et al., "Limits of Cooperativity in a Structurally Modular Protein: Response of the Notch Ankyrin Domain to Analogous Alanine Substitutions in Each Repeat," J. Mol. Biol., 2002, pp. 373-386, vol. 324.
Carstens, E., "Responses of Rat Spinal Dorsal Horn Neurons to Intracutaneous Microinjection of Histamine, Capsaicin, and Other Irritants," J. Neurophysiol., 1997, pp. 2499-2514, vol. 77, No. 5.
Chaney, M., "Side effects of intrathecal and epidural opioids," Can. J. Anaesth., 1995, pp. 891-903, vol. 42, No. 10.
Chen, Z-F. et al., "The Paired Homeodomain Protein DRG11 Is Required for the Projection of Cutaneous Sensory Afferent Fibers to the Dorsal Spinal Cord," Neuron, Jul. 19, 2001, pp. 59-73, vol. 31, No. 1.
Chothia, C. et al., "Conformations of immunoglobulin hypervariable regions," Nature, Dec. 21-28, 1989, pp. 877-883, vol. 342, No. 6252.
Chothia, C. et al., "Canonical Structures for the Hypervariable Regions of Immunoglobulins," J. Mol. Biol., 1987, pp. 901-917, vol. 196, No. 4.
CO, M. et al., "Humanized antibodies for antiviral therapy," PNAS, Apr. 1991, pp. 2869-2873, vol. 88, No. 7.
Cvejic, S. et al., "Dimerization of the Delta Opioid Receptor: Implication for a Role in Receptor Internalization," J. Biol. Chem., Oct. 24, 1997, pp. 26959-26964, vol. 272, No. 43.
Fairbanks, C et al., "Spinal Antinociceptive Synergism between Morphine and Clonidine Persists in Mice Made Acutely or Chronically Tolerant to Morphine," J. Pharmacol. Exp. Ther., 1999, pp. 1107-1116, vol. 288, No. 3.
Final Office Action from related U.S. Appl. No. 13/560,620, dated Oct. 29, 2013, 14 pages.
Fischer, P., "Cellular Uptake Mechanisms and Potential Therapeutic Utility of Peptidic Cell Delivery Vectors: Progress 2001-2006," Med. Res. Rev., 2007, pp. 755-795, vol. 27, No. 6.
Gallup, J. et al., "New quick method for isolating RNA from laser captured cells stained by immunofluorescent Immunohistochemistry; RNA suitable for direct use in fluorogenic TaqMan one-step real-time RT-PCR," Biol. Proced. Dnline, May 30, 2005, pp. 70-92, vol. 7, No. 1.
George, S. et al., "Oligomerization of mu- and delta-Opioid Receptors. Generation of Novel Functional Properties," J. Biol. Chem., Aug. 25, 2000, pp. 26128-26135, vol. 275, No. 34.
Hales, P., "Pruritus After Epidural Morphine," The Lancet, Jul. 26, 1980, p. 204, vol. 2.
Hampton, L. et al., "Loss of bombesin-induced feeding suppression in gastrin-releasing peptide receptor-deficient mice," PNAS, Mar. 1998, pp. 3188-3192, vol. 95, No. 6.
Han, S-K. et al., "Phospholipase Cbeta 3 Mediates the Scratching Response Activated by the Histamine H1 Receptor on C-Fiber Nociceptive Neurons," Neuron, Nov. 22, 2006, pp. 691-703, vol. 52.
Hylden, J. et al., "Intrathecal Morphine in Mice: A New Technique," Eur. J. Pharmacol., 1980, pp. 313-316, vol. 67.
Jensen, R.T. et al., "International Union of Pharmacology. LXVIII. Mammalian Bombesin Receptors: Nomenclature, distribution, pharmacology, signaling and functions in normal and disease states.," Pharmacol. Rev., Mar. 2008, pp. 1-42, vol. 60, No. 1.
Jones, E. et al., "Hypothesis. The Pruritus of Cholestasis: From Bile Acids to Opiate Agonists," Hepatology, 1990, pp. 884-887, vol. 11, No. 5.
Jordan, B. et al., "G-protein-coupled receptor heterodimerization modulates receptor function," Nature, Jun. 17, 1999, pp. 697-700, vol. 399, No. 6737.
Keith, D. et al., "Morphine Activates Opioid Receptors without Causing Their Rapid Internalization," J. Biol. Chem., Aug. 9, 1996, pp. 19021-19024, vol. 271, No. 32.
Kieffer, B., "Opioids: first lessons from knockout mice," TiPS, Jan. 1999, pp. 19-26, vol. 20.
Ko, M.C. et al., "An Experimental Itch Model in Monkeys: Characterization of Intrathecal Morphine-induced Scratching and Antinociception," Anesthesiology, Mar. 2000, pp. 795-805, vol. 92, No. 3.
Ko, M.C.H. et al., "The Role of Central mu Opioid Receptors in Opioid-Induced Itch in Primates," J. Pharmacol. Exp. Ther., Jul. 2004, pp. 169-176, vol. 310, No. 1.
Koch, T. et al., "C-terminal Splice Variants of the Mouse mu-Opioid Receptor Differ in Morphine-induced Internalization and Receptor Resensitization," J. Biol. Chem., Aug. 17, 2001, pp. 31408-31414, vol. 276, No. 33.
Kroog, G. et al., "Mammalian Bombesin Receptors," Med. Res. Rev., 1995, pp. 389-417, vol. 15, No. 5.
Law, P-Y. et al., "Molecular Mechanisms and Regulation of Opioid Receptor Signaling," Annu. Rev. Pharmacol. Toxicol., 2000, pp. 389-430, vol. 40.
Ling, G. et al., "Differential Development of Acute Tolerance to Analgesia, Respiratory Depression, Gastrointestinal Transit and Hormone Release in a Morphine Infusion Model," Life Sci., Aug. 18, 1989, pp. 1627-1636, vol. 45.
LOH, H. et al., "Mu Opioid receptor knockout in mice: effects on ligand-induced analgesia and morphine lethality," Mol. Brain Res., 1998, pp. 321-326, vol. 54.

(56) References Cited

OTHER PUBLICATIONS

Luo, M-C. et al., "An efficient intrathecal delivery of small interfering RNA to the spinal cord and peripheral neurons," Mol. Pain, 2005, pp. 1-8, vol. 1, No. 29.

Luo, J. et al., "The Majority of N-Methyl-D-Aspartate Receptor Complexes in Adult Rat Cerebral Cortex Contain at Least Three Different Subunits (NR1/NR2A/NR2B)," Mol. Pharmacol., 1997, pp. 79-86, vol. 51, No. 1.

Manara, L. et al., "Inhibition of Gastrointestinal Transit by Morphine in Rats Results Primarily from Direct Drug Action on Gut Opioid Sites," J. Pharmacol. Exp. Ther., 1986, pp. 945-949, vol. 237, No. 3.

Mao, L. et al., "The Scaffold Protein Homer1b/c Links Metabotropic Glutamate Receptor 5 to Extracellular Signal-Regulated Protein Kinase Cascades in Neurons," J. Neurosci., Mar. 9, 2005, pp. 2741-2752, vol. 25, No. 10.

Matthes, H. et al., "Loss of morphine-induced analgesia, reward effect and withdrawal symptoms in mice lacking the mu-opioid-receptor gene," Nature, Oct. 31, 1996, pp. 819-823, vol. 383.

McMahon, S. et al., "Itching for an explanation," TINS, 1992, pp. 497-501, vol. 15, No. 12.

Metze, D. et al., "Efficacy and safety of naltrexone, an oral opiate receptor antagonist, in the treatment of pruritus in internal and dermatological diseases," J. Am. Acad. Dermatol., Oct. 1999, pp. 533-539, vol. 41, No. 4.

Ngo, J. et al., "Computational Complexity, Protein Structure Prediction, and the Levinthal Paradox," Computational Complexity, 1994, pp. 491-494, Chapter 14.

Nichols, M. et al., "Transmission of Chronic Nociception by Spinal Neurons Expressing the Substance P Receptor," Science, Nov. 19, 1999, pp. 1558-1561, vol. 286.

Notice of Allowance from related U.S. Appl. No. 13/560,620 dated Feb. 25, 2014, 9 pages.

Notice of Allowance and Examiner Interview Summary from related U.S. Appl. No. 13/560,620 dated Jun. 11, 2014, 29 pages.

Pan, Y-X., "Diversity and Complexity of the Mu Opioid Receptor Gene: Alternative Pre-mRNA Splicing and Promoters," DNA Cell Biol., 2005, pp. 736-750, vol. 24, No. 11.

Pasternak, G., "Multiple opiate receptors: deja vu all over again," Neuropharmacology, 2004, pp. 312-323, vol. 47, Suppl. 1.

Paus, R. et al., "Frontiers in pruritus research: scratching the brain for more effective itch therapy," J. Clin. Invest., May 2006, pp. 1174-1185, vol. 116, No. 5.

Pfeiffer, M. et al., "Heterodimerization of Somatostatin and Opioid Receptors Cross-modulates Phosphorylation, Internalization, and Desensitization," J. Biol. Chem., May 31, 2002, pp. 19762-19772, vol. 277, No. 22.

Rudinger, J., "Characteristics of the amino acids as components of a peptide hormone sequence," Peptide Hormones, 1976, pp. 1-7.

Samways, D. et al., "Opioid elevation of intracellular free calcium: Possible mechanisms and physiological relevance," Cellular Signalling, 2006, pp. 151-161, vol. 18.

Schwarze, S. et al., "In Vivo Protein Transduction: Delivery of a Biologically Active Protein into the Mouse," Science, Sep. 3, 1999, pp. 1569-1572, vol. 285.

Sora, I. et al., "Opiate receptor knockout mice define mu receptor roles in endogenous nociceptive responses and morphine-induced analgesia," PNAS, Feb. 1997, pp. 1544-1549, vol. 94.

Szarvas, S. et al., "Neuraxial Opioid-Induced Pruritus: A Review," J. Clin. Anesth., 2003, pp. 234-239, vol. 15.

Office Action from related U.S. Appl. No. 13/560,620 dated May 16, 2013, 27 pages.

Voet, D. et al., "Chapter 9. Hemoglobin: Protein Function in Microcosm. Section 9-3: Abnormal Hemoglobins," Biochemistry, Second Edition, 1995, pp. 235-241, John Wiley & Sons, Inc.

Waldhoer, M. et al., "A heterodimer-selective agonist shows in vivo relevance of G protein-coupled receptor dimers," PNAS, Jun. 21, 2005, pp. 9050-9055, vol. 102, No. 25.

Whistler, J. et al., "Functional Dissociation of mu Opioid Receptor Signaling and Endocytosis: Implications for the Biology of Opiate Tolerance and Addiction," Neuron, Aug. 1999, pp. 737-746, vol. 23.

Xie, W. et al., "Genetic alteration of phospholipase C beta3 expression modulates behavioral and cellular responses to mu opioids," PNAS, Aug. 1999, pp. 10385-10390, vol. 96.

Zhao, Z-Q. et al., "Central serotonergic neurons are differentially required for opioid analgesia but not for morphine tolerance or morphine reward," PNAS, Sep. 4, 2007, pp. 14519-14524, vol. 104, No. 36.

Hanson, "Analgesic, Antipyretic and Anti-Inflammatory Drugs in Remington: The Science and Practice of Pharmacy vol. II," A. R. Gennaro ed. 19th ed., 1995, pp. 1196-1221 [Book].

* cited by examiner wild-type GRPR mutant
FIG. 5A 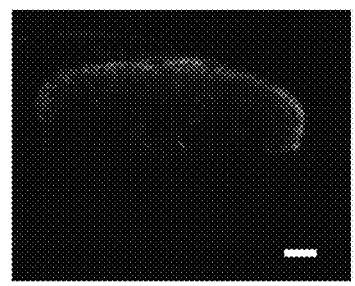 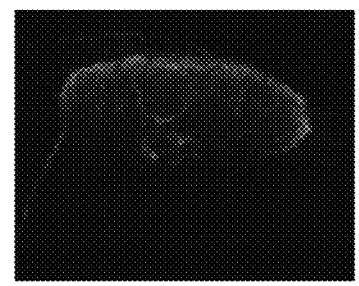 FIG. 5B
FIG. 5C 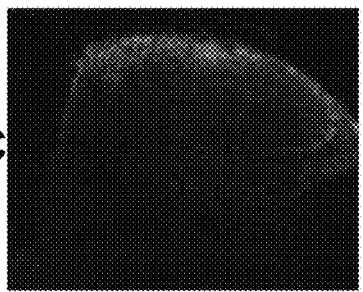 FIG. 5D
FIG. 5E 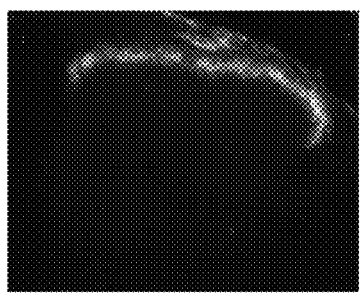 FIG. 5F
FIG. 5G  FIG. 5H

GRPR

Neurotensin

Prodynorphin

FIG. 11G 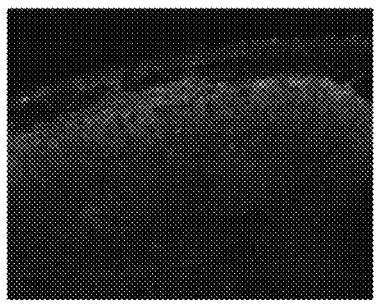 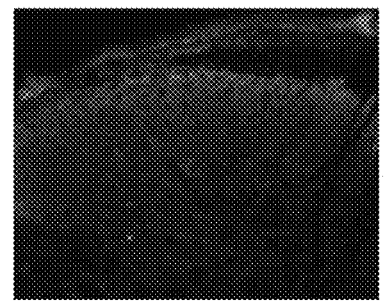 FIG. 11H
FIG. 11I 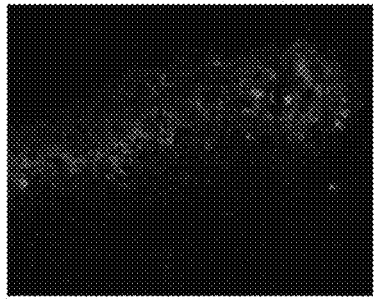 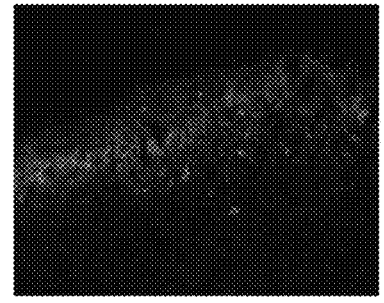 FIG. 11J
FIG. 11K 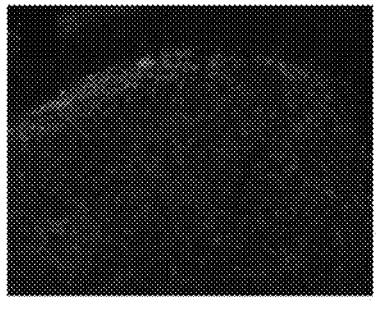 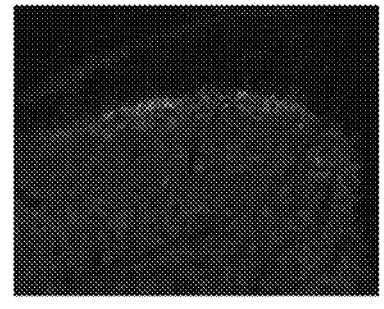 FIG. 11L

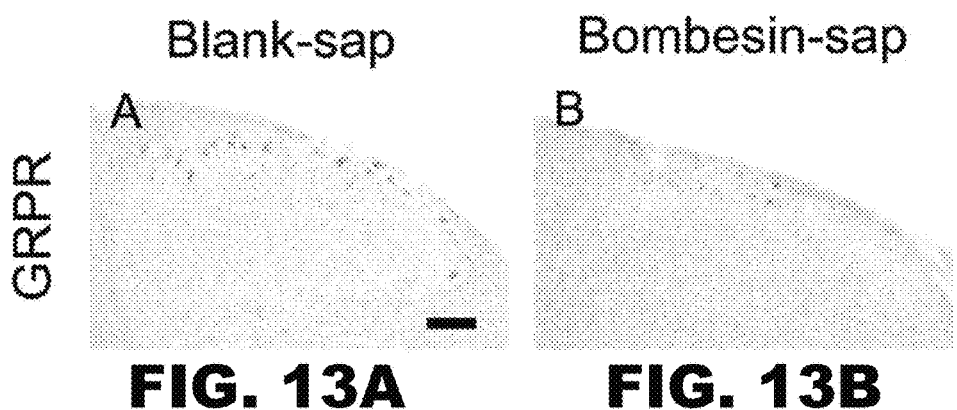
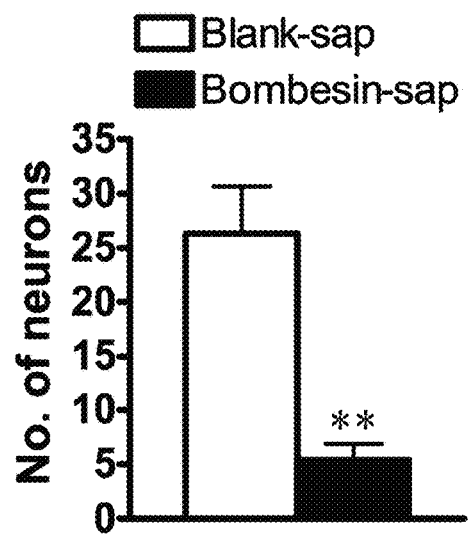
FIG. 13A  FIG. 13B
FIG. 13C

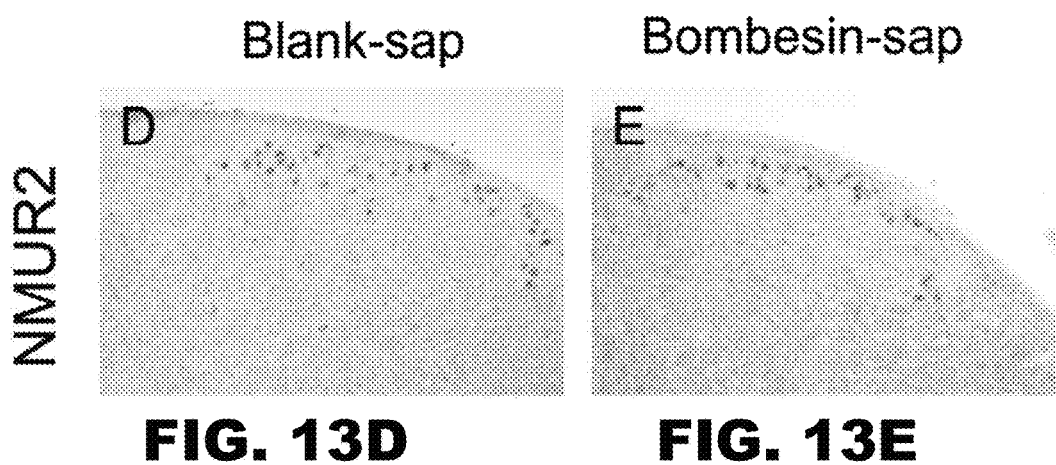
FIG. 13D  FIG. 13E
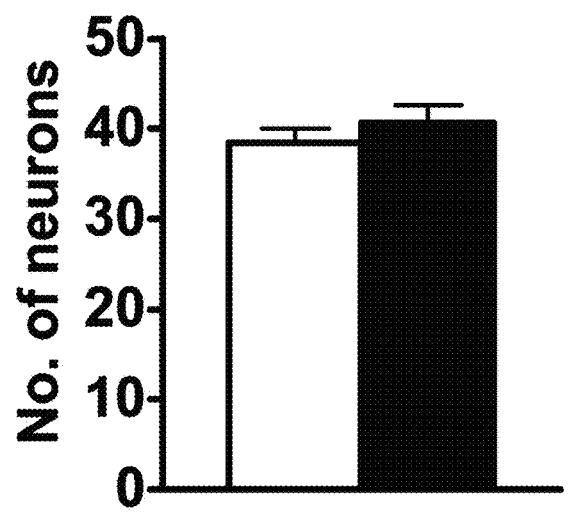
FIG. 13F

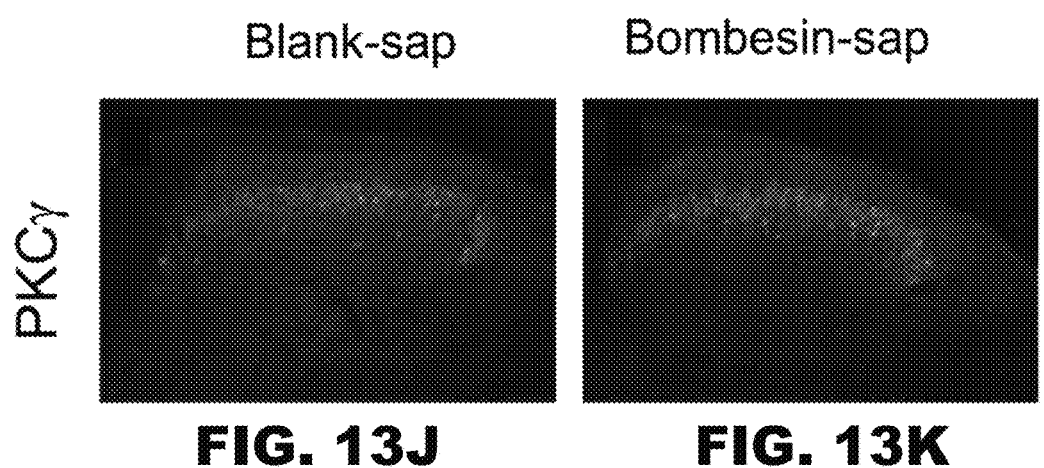
FIG. 13J  FIG. 13K
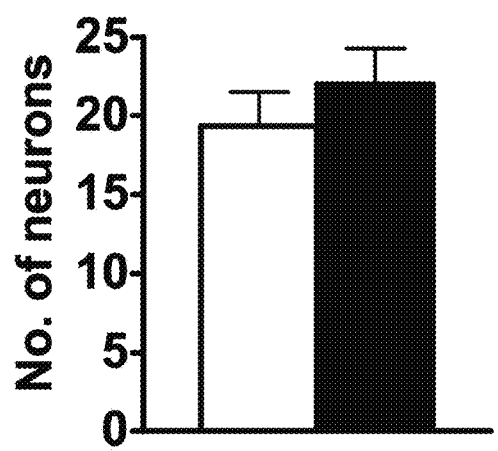
FIG. 13L

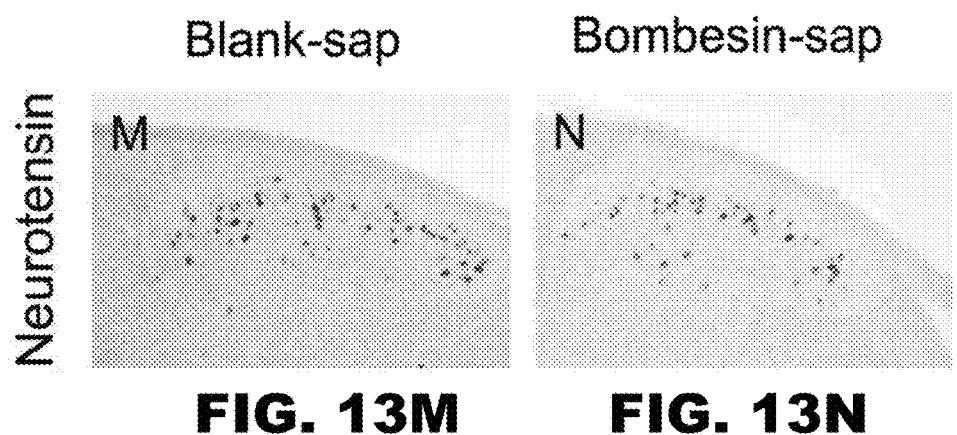
FIG. 13M  FIG. 13N
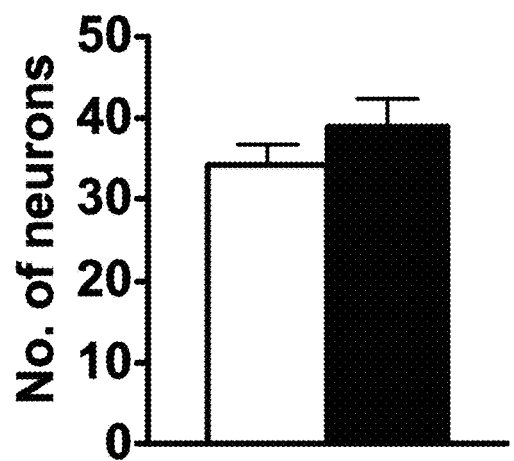
FIG. 13O

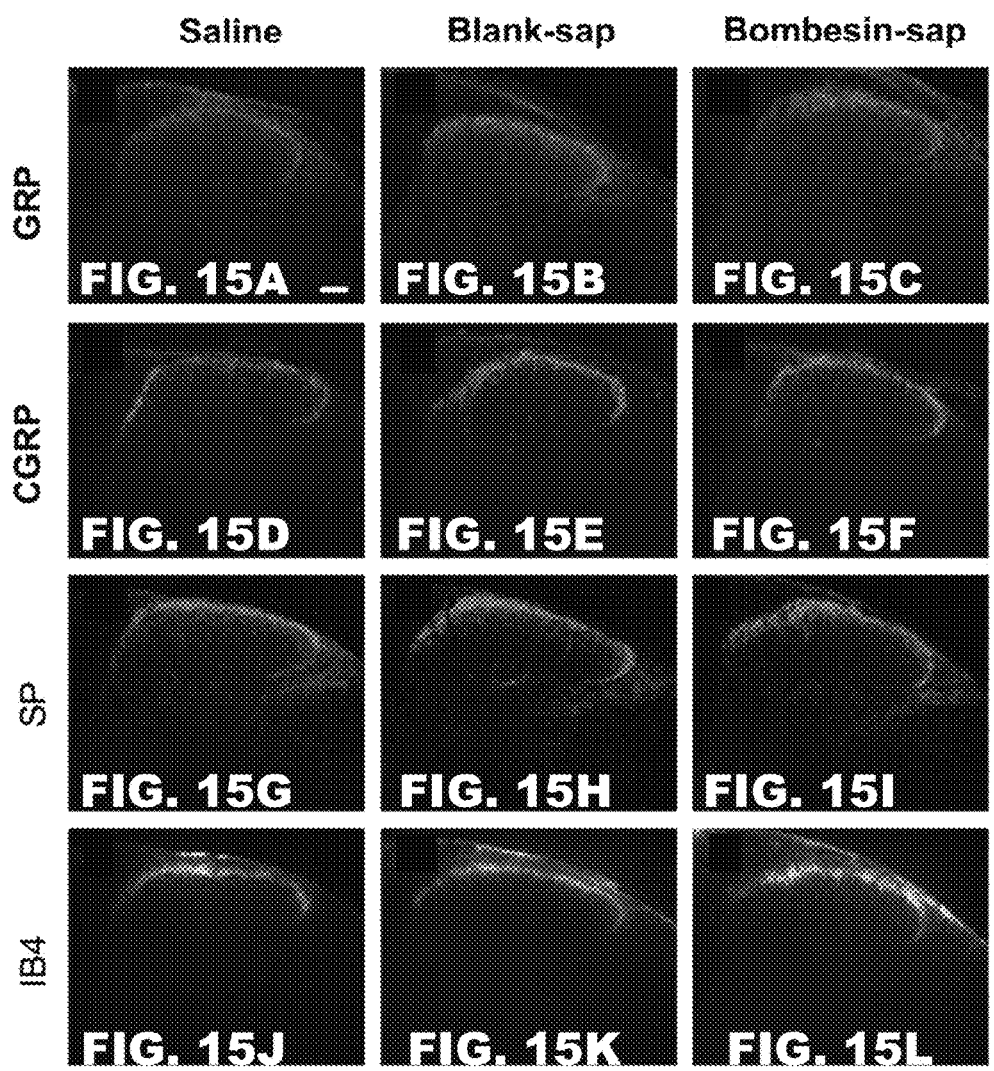

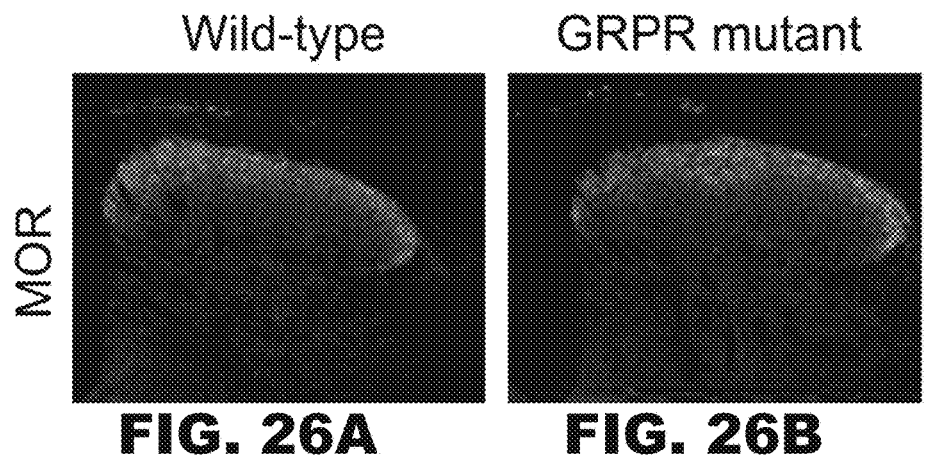
FIG. 26A   FIG. 26B
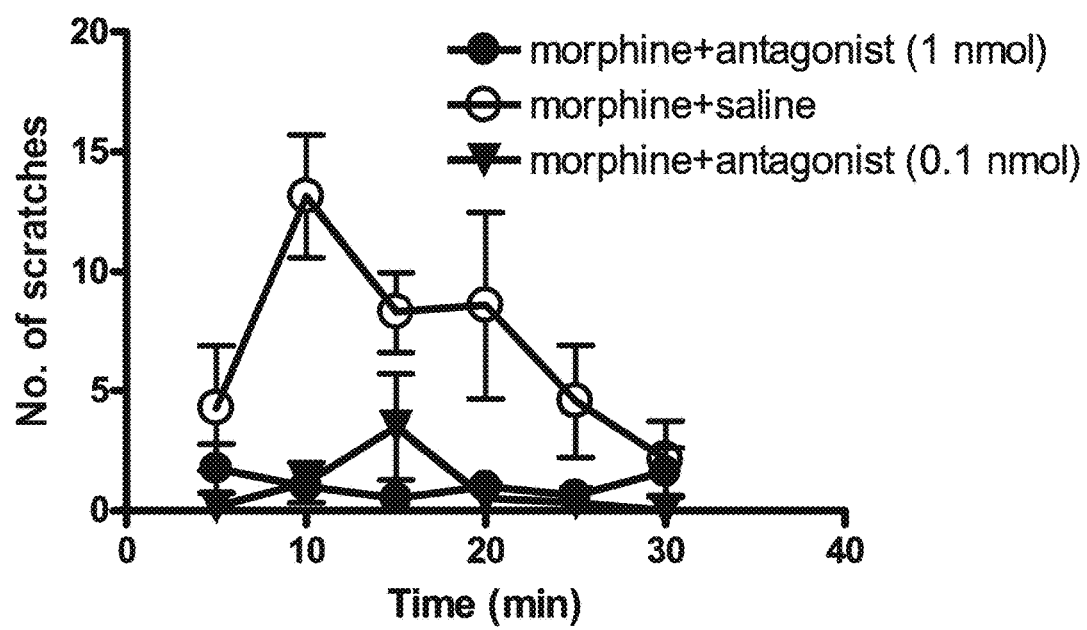
FIG. 27

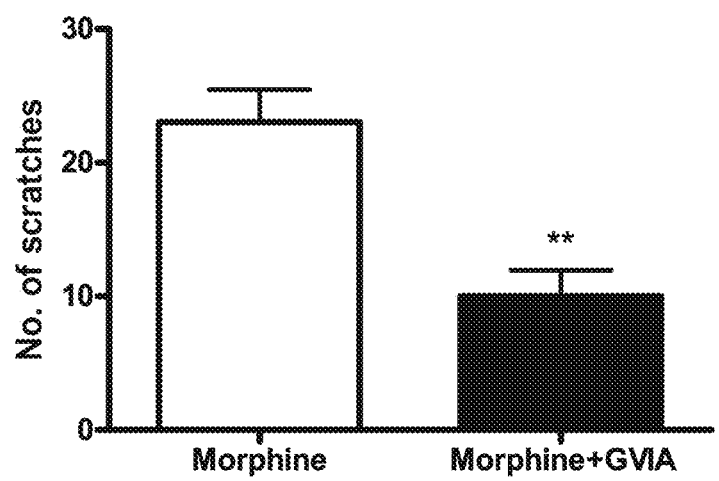
FIG. 30
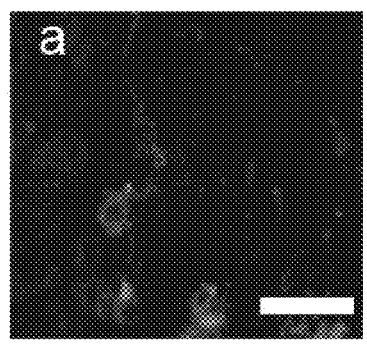 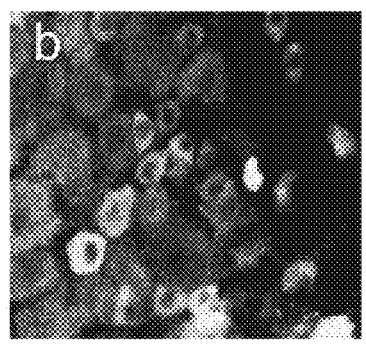
FIG. 31A    FIG. 31B

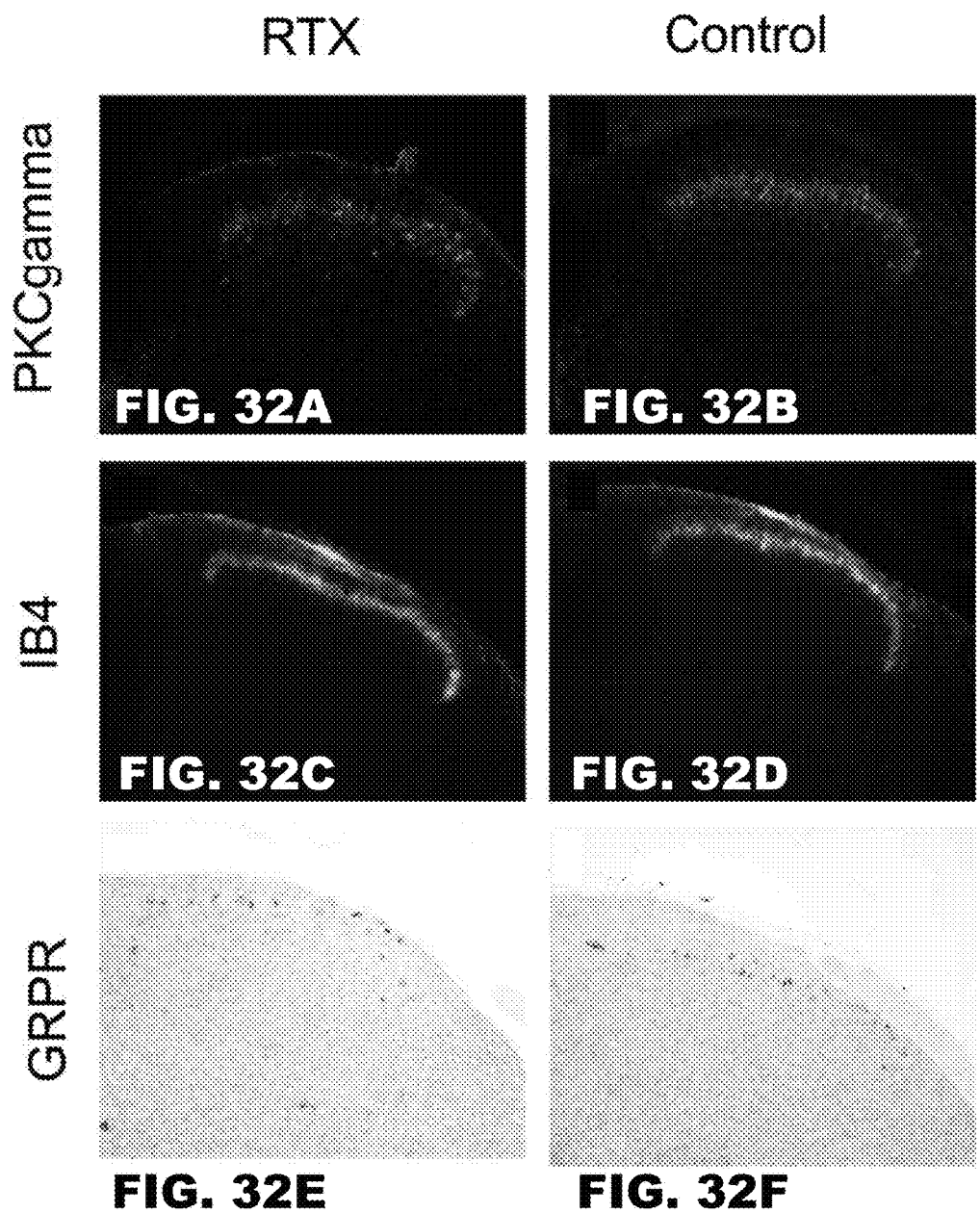

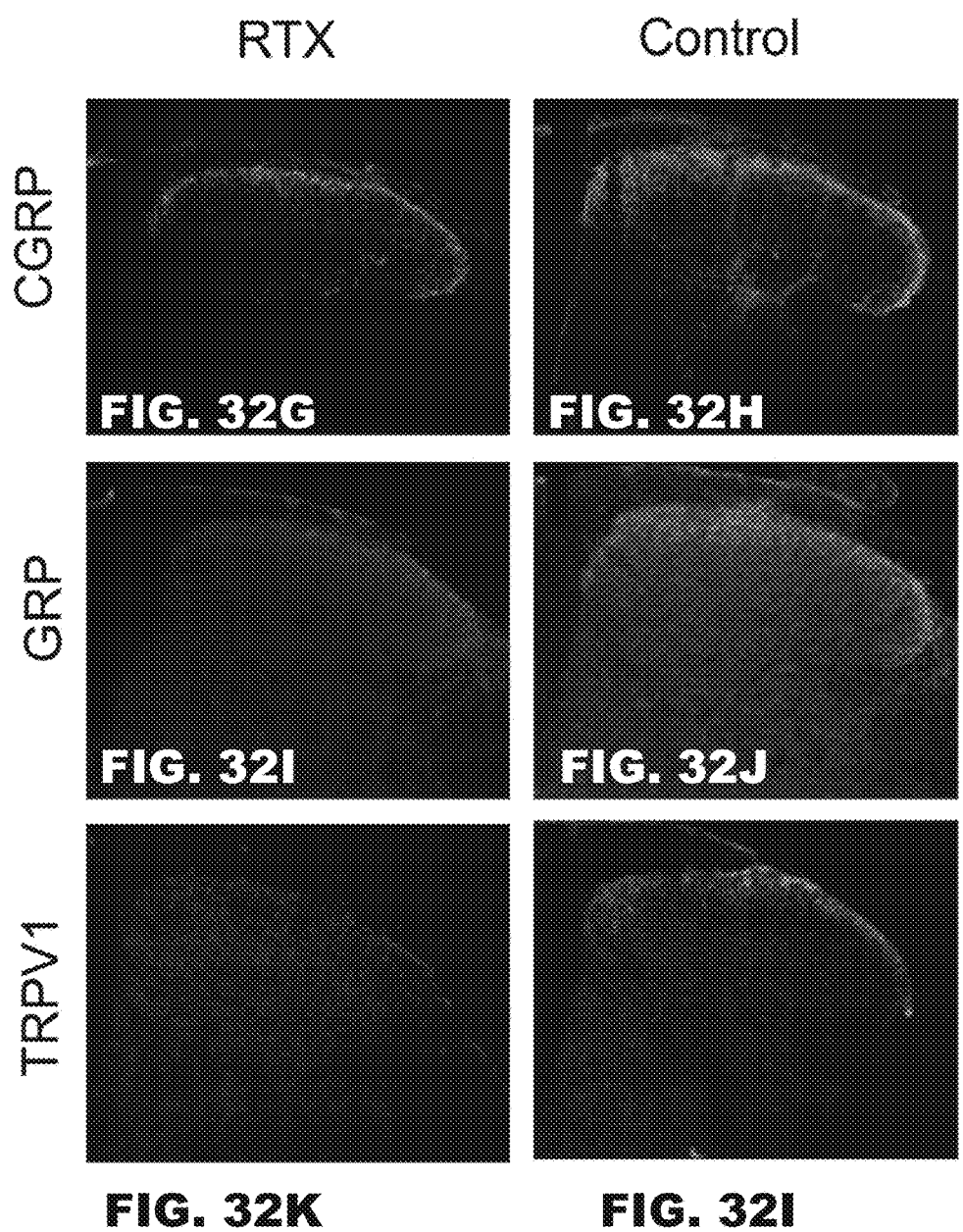

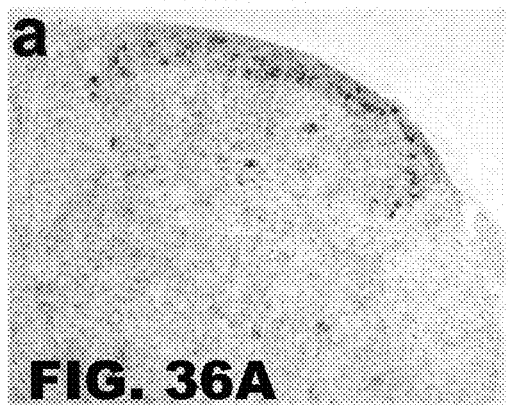
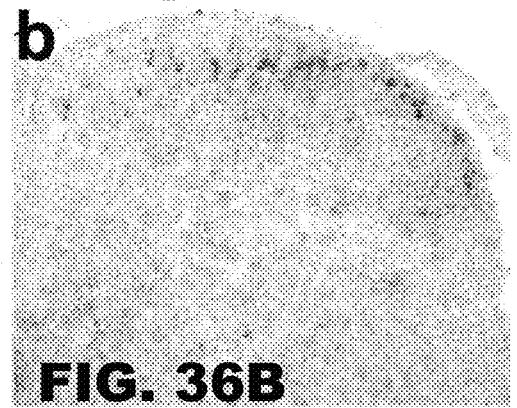
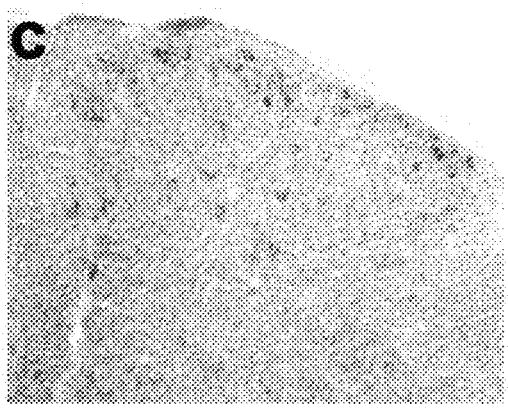
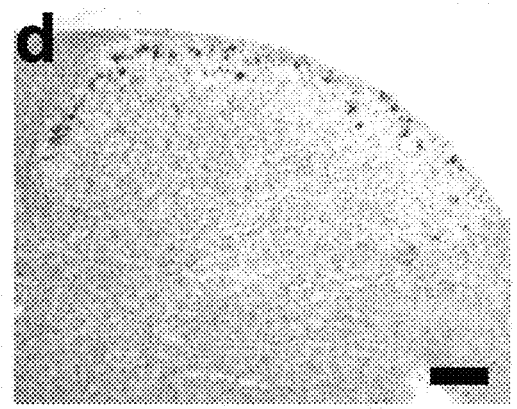
FIG. 36A
FIG. 36B
FIG. 36C
FIG. 36D

COMPOSITIONS AND METHODS FOR TREATING PRURITUS

GOVERNMENTAL INTEREST STATEMENT

This invention was made with government support under 5 RO1 NS043968-05 awarded by National Institutes of Health. The government has certain rights in the invention.

FIELD OF THE INVENTION

The present invention encompasses compositions and methods for treating pruritus.

BACKGROUND OF THE INVENTION

Itch, or pruritus, is an unpleasant sensation that causes the desire to scratch. Itch sensation includes both sensory and affective components, and can be induced by chemical, mechanical and psychological factors. While acute pruritus may serve as a protective mechanism, chronic pruritus represents a significant clinical problem resulting from renal insufficiency, cholestasis, Hodgkin's lymphoma, polycythemia vera, solid tumors, HIV, as well as several serious skin diseases (Twycross et al., 2003; Ikoma et al., 2006). Chronic itching disrupts normal sleep pattern and daily activity. In the US, pruritus occurs in approximately 20% of adults, in 25% of patients with jaundice, and in 50% of patients receiving renal dialysis. Atopic dermatitis, which accompanies severe itch, is the most common childhood skin disorder affecting 15-20% of children in developed countries, and 10% of children worldwide (Flohr et al., 2004). It has been estimated that children with atopic dermatitis lose an average of 1.9 hours of sleep per night, and their parents lose an average of 2.1 hours per night (Buys, 2007). Unfortunately, chronic pruritus is often resistant to treatment (e.g., anti-histamine), and thus represents one of the major problems to society (Carroll et al., 2005). The direct cost of atopic dermatitis in the United States alone has been estimated to be 1 billion dollars per year (Carroll et al., 2005). In contrast to numerous studies on chronic pain, the research on chronic pruritus remains a relatively neglected area (Ikoma et al., 2006; Paus et al., 2006).

While significant progress concerning the cellular mechanisms of itch sensation has been made over the past several years, the molecular basis underlying itch sensation in the central nervous system was heretofore unknown. The lack of understanding of the underlying mechanisms has hindered the development of effective mechanism-based anti-pruritic drugs. There is a need in the art, therefore, for a treatment of pruritus.

Itch sensation can be induced by chemical, mechanical and psychological factors. An opioid or opiate is a general term for natural or synthetic substances that bind to specific receptors ("opioid receptors") in the central nervous system, producing an agonist action. Opioid analgesics are extremely useful in managing severe acute pain, postoperative pain and chronic pain including cancer pain. Opioids, however, are known to induce pruritus. Consequently, there is a need in the art for combinations comprising opioids that alleviate pain, but that do not induce pruritus.

SUMMARY OF THE INVENTION

One aspect of the present invention encompasses a method for treating pruritus in a subject. The method comprises substantially inhibiting the activation of a first pruritus specific neuron receptor in a pruritus specific neuron of the subject.

Another aspect of the invention encompasses a method for treating pruritus in a subject. The method comprises substantially impeding the function of a pruritus specific neuron of the subject, such that the pruritus specific neuron does not relay the itch sensation.

Yet another aspect encompasses a method for identifying a compound that decreases the incidence of pruritus in a subject. The method comprises contacting a pruritus specific neuron receptor in a cell of the subject with both a test compound and a pruritus specific ligand, and comparing the activation of the cell to the activation of a cell contacted with only a pruritus specific ligand. If the activation of the pruritus specific neuron receptor is decreased in the cell contacted with the test ligand, compared to the cell contacted with pruritus specific ligand alone, then the test compound decreases the incidence of pruritus.

Still another aspect encompasses a combination comprising an agent that substantially inhibits the activation of a first pruritus specific neuron receptor in a pruritus specific neuron of a subject, and/or an agent that substantially inhibits the release and/or production of a pruritus specific ligand, and at least one analgesic agent.

A further aspect encompasses a combination comprising an agent that substantially impedes the function of a pruritus specific neuron of the subject, such that the pruritus specific neuron does not relay the itch sensation, and at least one analgesic agent.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

FIG. 5A-H depicts photomicrographs showing immunocytochemical staining of cross sections of the dorsal horn of the spinal cord. (A-D) shows that the peptidergic C-fibers marked by CGRP (A and B) and substance P (C and D) remain the same in GRPR mutant mice compared to wild-type mice. The non-peptidergic fibers marked by IB4 in GRPR mutant mice (F) are comparable to wild-type mice (E). The lamina II inner layer of spinal cord marked by PKCγ remains the same in GRPR mutant mice (H) when compared to wild-type mice (G). Scale bar: a, 100 μm (A-H).

FIG. 11A-L depicts photomicrographs showing mRNA expression of GRPR (A and B) (a, b), neurotensin (C and D), prodynorphin (E and F) detected by in situ hybridization and immunocytochemical staining of mu-opioid receptor (G, H), PKCg (i, j), NK1 (k, l) two weeks after treatment of 10 ng (A, C, E, G, I, K) or 1 mg of bombesin-saporin (B, D, F, H, J, L) intrathecally. GRPR+ neurons are depleted two weeks after intrathecal injection 1 mg of bombesin-saporin (B) but not by 10 ng of bombesin-saporin. Neurotension+ neurons and prodynorphin+ neurons are normal. Immunostaining of mu-opioid receptor, PKCγ, NK1 are normal.

FIG. 15A-L shows that primary afferent fibers detected by immunocytochemical staining were not affected by intrathecal blank-sap or bombesin-sap treatment. (A to C) Similar GRP+ fibers among groups. (D and F) Similar CGRP+ fibers among groups. (G and I) Similar SP+ fibers among groups. (J and L) The non-peptidergic primary afferent fibers labeled by IB4 are not affected by either blank-sap or bombesin-sap. Scale bar: A, 100 μm (A-L). Sap, saporin; GRP, gastrin-releasing peptide; CGRP, calcitonin gene related peptide; SP, substance P; IB4, isolectin B4.

FIG. 26A-B depicts micrographs illustrating that the expression of the mu opioid receptor (MOR) is not affected by the GRPR mutation. Immunocytochemical staining of cross sections of the dorsal horn of the spinal cord shows that the expression of the mu-opioid receptor remains the same in GRPR mutant mice (B) when compared to wild-type mice (A).

FIG. 27 depicts a graph showing that morphine-induced scratching behavior is blocked by co-injection of a GRPR antagonist agent. The scratching behavior induced by intrathecal morphine (0.3 nmol/5 μl) was significantly blocked by GRPR antagonist [D-Phe-6-Bn(6-13)OMe], which was injected together with morphine, compared with vehicle (open circles). Repeated measures analysis of variance (ANOVA); **P<0.01. n=6-8. All data are presented as means±s.e.m.

FIG. 30 depicts a graph showing that an N-type Calcium channel blocker reduces scratching behavior induced by intrathecal injection of morphine. The scratching behavior induced by intrathecal morphine (0.3 nmol/5 μl) is significantly inhibited by co-injection of ω-Conotoxin GVIA (N-type calcium channel blocker, 10 pmol). **P<0.01, Student's t-test. n=6.

FIG. 31A-D depicts several micrographs and an illustration showing the presence of GRP and TRPV1 in the dorsal root ganglion (DRG) neurons. (A-C) Immunocytochemical staining showed overlapping expression of GRP (A, red) and TRPV1 (B, green) in DRG neurons. Note that GRP and TRPV1 are partially overlapping ((C), yellow). (D) GRP+ neurons were detected in 8.6% (41/474) of the DRG neurons, and TRPV1+ neurons were detected in 29.5% (140/474) of the DRG neurons. 80.5% (33/41) of the GRP+ DRG neurons showed TRPV1 staining. Scale bar: a, 50 μm (A-C).

FIG. 32A-L depicts micrographs showing that peptidergic but not non-peptidergic fibers were depleted by resiniferatoxin (RTX) treatment. RTX treatment (intrathecally, 25 ng/5 μl) did not change the expression of PKCγ (A,B) and GRPR (E,F) when comparing the RTX treated group (A,E) with control group (B,F). The IB4 positive non-peptidergic fibers remain the same after RTX treatment (C) compared with the control group (D). Peptidergic fibers labeled by CGRP are largely diminished after treatment of RTX (G) compared with the control group (H). GRP+ fibers are almost lost in the RTX treated group (I) compared with the control group (J). TRPV1 staining is lost after RTX treatment (K) compared to the control group (L).

FIG. 36A-D depicts photomicrographs showing NMBR and GRPR mRNA expression patterns in wild type mouse spinal dorsal horn obtained by in situ in situ hybridization (ISH). (A and B) 1 week age. (C and D) 4 weeks age. Scale bar in (D) for all images, 100 μm.

DETAILED DESCRIPTION OF THE INVENTION

Figure 1A:
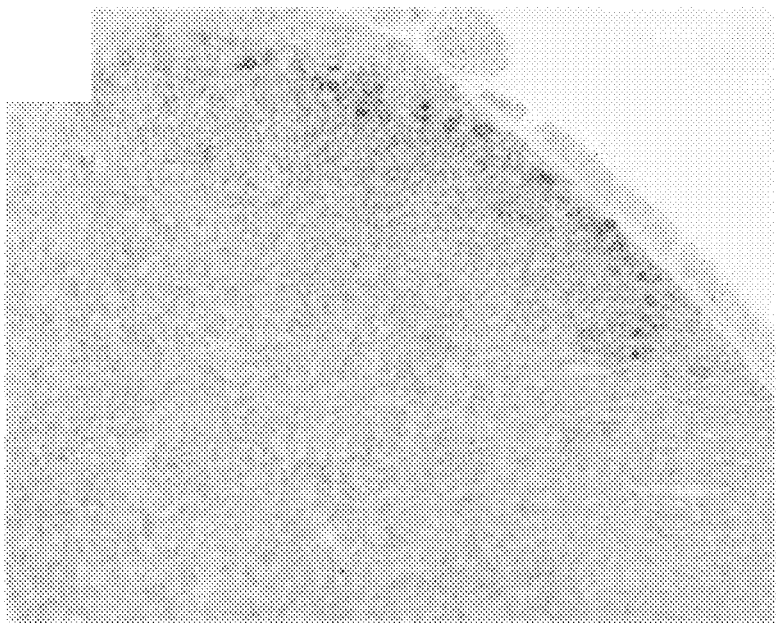
FIG. 1A-B depicts photomicrographs showing GRPR expression in lamina I of the spinal cord detected by in situ hybridization. (A) GRPR expression detected by in situ hybridization is restricted to lamina I of the dorsal horn. (B) higher magnification of (A) showing GRPR+ cells in the dorsal horn (arrows).

The present invention provides methods and combinations for treating pruritus. Generally speaking, the invention provides methods for treating pruritus by providing methods of substantially inhibiting the activation of a pruritus specific receptor on a pruritus specific neuron. In this context, "pruritus specific neurons" refers to neurons that express a pruritus specific receptor, are located in the central nervous system, and are responsible for transmitting the itch sensation, as opposed to pain perception. For instance, GRPR is a pruritus specific receptor, and neurons expressing GRPR in the dorsal horn are pruritus specific neurons. Similarly, NMBR is a pruritus specific receptor, and neurons expressing NMBR in the dorsal horn are pruritus specific neurons.

Advantageously, substantially inhibiting the activation of a pruritus specific receptor on a pruritus specific neuron provides a direct means of treating pruritus by specifically targeting the neurons responsible for the itch sensation, as opposed to other sensations. Similarly, substantially inhibiting the activation of a pruritus specific receptor on a pruritus specific neuron provides a central means of treating pruritus by specifically targeting the neurons of the central nervous system responsible for the itch sensation, as opposed to only inhibiting peripheral mediators, such as histamine.

Usually, an agent that alleviates pruritus may substantially inhibit the activation of a pruritus specific receptor on a pruritus specific neuron, may substantially inhibit the production and/or release of a pruritus specific ligand, may substantially impede the function of a pruritus specific neuron, or any combination thereof. In some embodiments, a combination of the invention may comprise more than one agent that alleviates pruritus. For instance, a combination may comprise an agent that substantially inhibits the activation of a pruritus specific receptor on a pruritus specific neuron and an agent that may substantially inhibit the production and/or release of a pruritus specific ligand.

Pruritus may be histamine dependent or histamine independent. In one embodiment, the methods of the invention may be used to treat histamine dependent pruritus. In another embodiment, the methods of the invention may be used to treat histamine independent pruritus.

Methods of the invention may be used to treat pruritus arising from a variety of causes such as xerosis, skin conditions (such as psoriasis, eczema, sunburn, athlete's foot), insect bites, poisonous plants (such as poison ivy, poison oak, poison sumac), Hodgkin's disease, jaundice, polycythemia, scabies, lice, worms, thyroid illness, diabetes mellitus, dandruff, iron deficiency anemia, parasitic infections, medications, cholestasis, pruritus related to pregnancy, HIV infection or other causes of itching or pruritus.

The present invention also provides a combination comprising an agent to alleviate pruritus and at least one analgesic agent. In particular, the invention provides methods of alleviating pruritus induced by an analgesic agent.

I. Substantially Inhibiting Pruritus Specific Neuron Receptor Activation

One aspect of the invention encompasses treating pruritus by substantially inhibiting the activation of a pruritus specific neuron receptor. In one embodiment, the activation is substantially inhibited by an antagonist to a pruritus neuron specific receptor. Non-limiting examples of pruritus neuron specific receptors include gastrin releasing peptide receptor (GRPR) and NMB receptor (NMBR). In one embodiment, the pruritus specific neuron is contacted by a GRPR antagonist. In another embodiment, the pruritus specific neuron is contacted by a NMBR antagonist. In yet another embodiment, the pruritus specific neuron is contacted by both a GRPR antagonist and a NMBR antagonist.

(a) GRPR Antagonists

In certain embodiments, the activation of a pruritus specific neuron receptor is substantially inhibited by contacting the receptor with a GRPR antagonist. GRPR antagonists are known in the art, and may be peptide or peptide derivative antagonists, small molecular weight antagonists, antibody antagonists, or the like. In certain embodiments, the GRPR receptor antagonist may be selected from the group of antagonists including [Leu$^{13}$, ψ(CH$_2$NH)Leu$^{14}$]Bn, [D-Phe$^6$]Bn(6-13)NH$_2$, [D-Phe$^6$]Bn(6-13)ethylamide, [D-Phe$^6$]Bn(6-13)propylamide, [D-Phe$^6$]Bn(6-13)heptylamide, [D-Phe$^6$]Bn(6-13)phenethylamide, [D-Phe$^6$]Bn(6-13)-4-methylphenethylamide, [D-Tyr$^6$]Bn(6-13)propylamide, [D-Phe$^6$, Val$^{10}$, ψ (CH$_2$NH)Gly$^{11}$]Bn(6-13)PA, [D-Phe$^6$]Bn(6-13)hydrazide, [D-Phe$^6$]Bn(6-13)methyl ester, [D-Phe$^6$]Bn(6-13)ethyl ester and N—Ac-GRP(20-26) ethyl ester. In other embodiments, the GRPR receptor antagonists may include nonapeptide compounds disclosed in U.S. Pat. No. 5,244,883, nonapeptide compounds disclosed in U.S. Pat. No. 5,369,094, analogues of substance P (Coy et al., J. Biol. Chem. 263, 5056 (1988)), and analogues of GRP(20-27) (Heimbrook et al., J. Biol. Chem. 264, 11258 (1989)). In yet other embodiments, the GRPR antagonist may be selected from the group of antagonists comprising RC-3095, RC3940-II, BW2258U89, BW1023U90, PD176252, JMV594, and JMV641.

GRPR antagonists may be purchased commercially or synthesized using methods known in the art.

(b) NMBR Antagonists

In some embodiments, the pruritus specific neurons are substantially inhibited by contacting the neuron with a NMBR antagonist. NMBR antagonists are known in the art, and may be peptide or peptide derivative antagonists, small molecular weight antagonists, antibody antagonists, or the like. In certain embodiments, the NMBR antagonist may be selected from the group of antagonists including BIM 23127, D-Nal, Cys, Tyr, D-Trp, Lys, Val, Cys, Nal-NH$_2$, and PD 168368 (Ryan et al., 1999).

NMBR antagonists may be purchased commercially or synthesized using methods known in the art.

(c) Administering the Pruritus Specific Neuron Receptor Antagonist

The antagonist generally will cross the blood brain barrier (BBB) of the subject to contact the pruritus specific neuron in the central nervous system. The antagonist may inherently be able to cross the (BBB). For example, compounds with a molecular weight below 500 daltons. Alternatively, the antagonist may be delivered across the (BBB). Methods of delivering antagonists across the BBB are known in the art. For instance, antagonists may be delivered via injection into the intrathecal space. Additionally, modalities for drug delivery across the BBB may entail its disruption by osmotic means, biochemically by the use of vasoactive substances such as bradykinin, or even by localized exposure to high intensity focused ultrasound (HIFU). Other strategies to cross the BBB may entail the use of endogenous transport systems, including carrier-mediated transporters, receptor-mediated transcytosis, and blocking of active efflux transporters.

The antagonists of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

Injectable preparations of the antagonists, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

For therapeutic purposes, formulations for administration of the antagonist may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amount of the antagonist that may be combined with the carrier materials to produce a single dosage of the composition will vary depending upon the subject and the particular mode of administration. In some embodiments, the amount of the antagonist may be between about 1 µg to about 100 µg. In other embodiments, the amount of the antagonist may be at least about 1 µg, at least about 10 µg, at least about 20 µg, at least about 30 µg, at least about 40 µg, at least about 50 µg, at least about 60 µg, at least about 70 µg, at least about 80 µg, at least about 90 µg, or at least about 100 µg. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

II. Agents That Substantially Inhibit the Release and/or Production of a Pruritus Specific Ligand In another embodiment, an agent that alleviates pruritus may substantially inhibit the release and/or production of a pruritus specific ligand. An agent used to substantially inhibit the release and/or production of the pruritus specific ligand does not necessarily need to cross the BBB, as it may act on the afferent nerve fibers. In one embodiment, an agent may substantially inhibit the release and/or production of GRP. In another embodiment, an agent may substantially inhibit the release and/or production of NMB.

Agents that substantially inhibit the release and/or production of a pruritus specific ligand are known in the art. For instance, N-type calcium channel blockers are known to inhibit the release of neuropeptides from primary afferent fibers. In one embodiment, therefore, an agent that alleviates pruritus may be an N-type calcium channel blocker. Non-limiting examples include Ziconotide and ω-Conotoxin GVIA. Ziconotide is an FDA approved intrathecally administered peptide that blocks the N-type calcium channel.

As described in section (a)(i) above, agents used to substantially inhibit the release and/or production of the pruritus specific ligand may be in the form of free bases or pharmaceutically acceptable acid addition salts thereof.

The amount of an agent that substantially inhibits the release and/or production of a pruritus specific ligand that may be combined with carrier materials to produce a single dosage of the combination will vary depending upon the subject and the particular mode of administration. For instance, in some embodiments, dosages of Ziconotide may range from about 0.01 mcg/hour to about 0.8 mcg/hr. In other embodiments, dosages may range from about 0.01 mcg/hour to about 0.1 mcg/hour. For instance, the dosage may be about 0.01, 0.02, 0.03, 0.04, 0.05, 0.06, 0.07, 0.08, 0.09, or 0.1 mcg/hour. Alternatively, the dosage may range from about 0.1 mcg/hour to about 0.8 mcg/hour. For instance, the dosage may be about 0.1, 0.2, 0.3, 0.4, 0.5, 0.6, 0.7, or 0.8 mcg/hour. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

In some embodiments, a combination of the invention may comprise an agent from section (I)(a)(i) and an agent from section (I)(a)(ii).

III. Substantially Inhibiting Pruritus Specific Neurons in the Periphery

Pruritus may also be treated by substantially inhibiting the activation of a pruritus specific neuron receptor by blocking a pruritus specific ligand from interacting with a pruritus neuron specific receptor. As used herein, pruritus specific ligand refers to a ligand for a pruritus specific neuron receptor. For example, GRP and NMB are non-limiting examples of pruritus specific ligands. In one embodiment, the activation of a pruritus specific neuron receptor may be substantially inhibited by blocking the interaction of GRP with a pruritus neuron specific receptor. In another example, the activation of a pruritus specific neuron receptor may be substantially inhibited by blocking the interaction of NMB with a pruritus neuron specific receptor. In yet another example, the activation of a pruritus specific neuron receptor may be substantially inhibited by blocking the interaction of both GRP and NMB with one or more pruritus neuron specific receptors.

Methods of blocking the interaction of a pruritus specific ligand from interacting with the pruritus neuron specific receptor are known in the art. Antibodies, peptides, peptide derivatives, or small molecules may be used to block the interaction between the pruritus specific ligand and the pruritus neuron specific receptor. For instance, an antibody that recognizes the pruritus specific ligand and intereferes with the ligand binding to the pruritus neuron specific receptor may be used. For example, the GRP-blocking antibody 2A11 may be used to block the interaction of GRP with a pruritus neuron specific receptor.

Alternatively, the release and/or production of the pruritus specific ligand may be substantially inhibited. Agents used to substantially inhibit the release and/or production of the pruritus specific ligand do not need to cross the BBB to substantially inhibit the pruritus specific neurons in the central nervous system. As described above, agents used to substantially inhibit the release and/or production of the pruritus specific ligand may be in the form of free bases or pharmaceutically acceptable acid addition salts thereof.

Additionally, the agents may be formulated into pharmaceutical compositions and administered by a number of different means that will deliver a therapeutically effective dose. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations and formulations for parenteral administration may be prepared as described above. Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the compound of the invention that may be combined with the carrier materials to produce a single dosage of the composition will vary depending upon the subject and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

IV. Substantially Impeding the Function of a Pruritus Specific Neuron

In some embodiments, the antagonist may be coupled to a neurotoxin that is incapable of independently entering the neuron. In these embodiments, the antagonist binds to the receptor on the pruritus neuron cell membrane, and delivers the neurotoxin to the neuron, thereby selectively impeding the function of the pruritus specific neuron, and hence, substantially inhibiting the pruritus specific neuron. Non-limiting examples of suitable neurotoxins may include saporin, modified botulinum toxin, the enzymatic chain of ricin, the ribosome-inactivating protein gelonin, the enzymatic chain of *Pseudomonas* exotoxin, and the enzymatic chain of diphtheria toxin. Methods of coupling an antagonist to a neurotoxin are well known. For instance, see Nichols et al. Science (1999) 286:1558-1561 and published US Patent Applications 2007/0110769, 2007/0048335, and 20040253248. In one embodiment, the antagonist is coupled to saporin. Methods of coupling an antagonist to saporin are known in the art, and may be found, for example in published US Patent Application 20040253248.

Generally speaking, the amount of antagonist coupled to a neurotoxin may be between about 200 ng to about 2 µg. In certain embodiments, the amount may be less than about 200 ng, at least about 200 ng, at least about 500 ng, at least about 1 µg, at least about 1.5 µg, or at least about 2 µg. The antagonist coupled to a neurotoxin may typically be administered as detailed in section I above.

V. Screening Methods

Another aspect of the invention provides screening methods for identifying compounds that decrease the incidence of pruritus. Typically, the method comprises comparing the activation of a pruritus specific neuron receptor in a cell contacted with both a test compound and a pruritus specific ligand to the activation of a pruritus specific neuron receptor in a cell contacted with only a pruritus specific ligand, wherein if the activation of the pruritus specific neuron receptor is decreased in the cell contacted with the test compound compared to the cell contacted with pruritus specific ligand alone, then the test compound decreases the incidence of pruritus.

In some embodiments, the pruritus specific neuron receptor that is activated is GRPR. In other embodiments, the pruritus specific neuron receptor that is activated is NMBR.

The activation of a pruritus specific neuron receptor may be measured by means known in the art. For instance, a biochemical modification of the receptor itself or a downstream signaling molecule may be quantified. A non-limiting example of a biochemical modification is phosphorylation. Alternatively, neuron activation may be observed as an indicator of pruritus specific neuron receptor activation. Methods of observing neuron activation are known in the art.

VI. Combinations Comprising Agents That Alleviate Pruritus and Analgesic Agents

One aspect of the present invention provides a combination comprising an agent to alleviate pruritus and at least one analgesic agent. Suitable analgesic agents are described below.

(a) Analgesic Agent

A combination of the invention also comprises at least one analgesic agent. For instance, a combination of the invention may comprise at least one, at least two, at least three, at least four, at least five, at least six, or more than six analgesic agents. In some embodiments, at least one analgesic agent may be an opioid. As used herein, an opioid is a substance that binds to an opioid receptor and possesses biological activity. A non-limiting example of an opioid is an opiate. In other embodiments, at least one analgesic agent may be a non-opioid analgesic. In certain embodiments, the combination may comprise at least one opioid analgesic and at least one non-opioid analgesic.

i. Opioid Analgesic Agents

An analgesic agent of the invention may be an opioid analgesic agent. In some embodiments, an opioid analgesic may be a full or a partial opioid receptor agonist. In exemplary embodiments of the invention, the opioid analgesic agent induces pruritus. Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

In other embodiments, a combination may comprise more than one opioid analgesic. For instance, a combination may comprise more than one full opioid agonist, more than one partial opioid agonist, or at least one full opioid agonist and at least one partial opioid agonist.

The amount of the opiate analgesic agent that comprises a combination of the invention depends, in part, upon the analgesic chosen and whether the dosage form is to be formulated for immediate release or sustained release of the analgesic. For example, if morphine is the intended opiate, the morphine may be present in single doses between about 10 mg and about 60 mg including, but not limited to, about 15 mg, about 20 mg, about 30 mg and about 40 mg. Alternatively, a pharmaceutical combination may be formulated to include between about 30 mg to about 60 mg of morphine in a single slow-release tablet or capsule. If meperidine is chosen as the analgesic or a member of the analgesic combination, the meperidine may be present in single doses ranging from about 50 mg to about 150 mg. If fentanyl is chosen as the analgesic or a member of the analgesic combination, the fentanyl may be present in doses equivalent to doses ranging from about 200 μg, to about 1600 μg per single dose, including about 400 μg, about 600 μg, about 800 μg, and about 1200 μg of fentanyl base. If hydromorphone is chosen as the analgesic or a member of the analgesic combination, the hydromorphone may be present in doses ranging from about 1 mg to about 5 mg of hydromorphone per single dose. If oxymorphone is chosen as the analgesic or a member of the analgesic combination, the oxymorphone may be present in doses ranging from about 1 mg to about 10 mg per single dose. If oxycodone is chosen as the analgesic or a member of the analgesic combination, the oxycodone may be present in doses ranging from about 5 mg to about 20 mg per single dose. If hydrocodone is chosen as the analgesic or a member of the analgesic combination, the hydrocodone may be present in doses ranging from about 2.5 mg to about 15 mg, including, but not limited to, about 5 mg, about 7.5 mg and about 10 mg per single dose. If methadone is chosen as the analgesic or a member of the analgesic combination, the methadone may be present in doses ranging from about 5 mg to about 10 mg per single dose. If propoxyphene is chosen as the analgesic or a member of the analgesic combination, the propoxyphene may be present in doses ranging from about 32 mg to about 65 mg of the hydrochloride salt or from about 50 mg to about 100 mg of the napsylate salt per single dose. If pentazocine is chosen as the analgesic or a member of the analgesic combination, the pentazocine may be present in doses including, but not limited to, about 50 mg pentazocine base or doses of a pharmaceutically-acceptable salt of pentazocine approximately equivalent to about 50 mg of pentazocine base per single dose. If levorphanol is chosen as the analgesic or a member of the analgesic combination, the levorphanol may be present in doses including but not limited to about 2 mg of levorphanol tartrate per single dose. If codeine is chosen as the analgesic or a member of the analgesic combination, the codeine may be present in doses including but not limited to doses of a pharmaceutically-acceptable salt of codeine approximately equivalent to a range from about 30 mg to about 60 mg of codeine phosphate or approximately equivalent to a range of about 15 mg to about 60 mg of codeine sulfate per single dose.

ii. Non-Opioid Analgesic Agent

In another embodiment, a combination of the invention may comprise at least one non-opioid analgesic. Non-limiting examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof.

Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone.

For a more detailed description of the NSAIDs, see Paul A. Insel, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995) which are hereby incorporated by reference in their entireties. Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Dosages of non-opioid analgesic agents are known in the art, and depend, in part, on the subject, the analgesic agent, the origin of the pain, and the administration route. For instance, in some embodiments, the dosage of rofecoxib may be between about 5 mg and about 60 mg per day, the dosage of celecoxib may be between about 25 mg and about 500 mg per day, the dosage of naprosyn may be between about 250 mg and 1250 mg per day, and the dosage of aspirin may be between about 80 mg and about 400 mg per day. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

iii. Combinations of Opioid and Non-Opioid Analgesic Agents

As detailed above, a combination of the invention may comprise more than one analgesic agent. This is particularly true if the analgesic agents, when administered together, produce a synergistic analgesic effect. In certain embodiments, a combination comprises at least one opioid analgesic agent and at least one non-opioid analgesic.

As acetaminophen has been shown to have a synergistic analgesic activity with the opiate analgesics, in some embodiments, a combination may comprise at least one opioid analgesic and acetaminophen. In the embodiments of the present invention comprising acetaminophen, the acetaminophen is generally present in a range of between about 10 mg and about 2000 mg. In certain embodiments, the acetaminophen is present in a range of about 50 mg to about 1000 mg per dosage form. In other embodiments, the acetaminophen is present in a range of about 325 mg to about 750 mg per dosage form. In still other embodiments, each dosage form includes about 500 mg of acetaminophen. For more details on combinations comprising acetaminophen, see U.S. Pat. No. 6,375,957, hereby incorporated by reference in its entirety.

iv. Pharmaceutical Compositions Comprising Analgesic Agents

An analgesic agent detailed above may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

(b) Other Agents

Combinations of the present invention may further comprise additional agents. For instance, a combination may comprise an agent directed to alleviating an unwanted side effect of the analgesic agent. Non-limiting examples may include an anti-nausea agent, an anti-vomiting agent, an agent to alleviate constipation, an agent to alleviate respiratory depression, or an opioid antagonist.

Anti-nausea or anti-vomiting agents may include 5-HT3 receptor antagonists such as dolasetron, granisetron, ondansetron, tropisetron, and palonosetron; dopamine antagonists, such as domperidone, droperidol, haloperidol, chlorpromazine, promethazine, prochlorperazine, metoclopramide, and alizapride; antihistamines (H1 histamine receptor antagonists) such as cyclizine, diphenhydramine, dimenhydrinate (Gravol), meclizine, promethazine (pentazine, phenergan, promacot), and hydroxyzine; cannabinoids such as cannabis (marijuana), dronabinol (Marinol), nabilone (Cesamet), and sativex; benzodiazepines, such as midazolam and lorazepam; anticholinergics such as hyoscine (also known as scopolamine); steroids such as dexamethasone; trimethobenzamide; ginger; emetrol; propofol given intravenously; peppermint; or other suitable anti-nasea or anti-vomiting agents. The amount of an anti-nausea or anti-vomiting agent included in a combination of the invention may be readily determined by one of skill in the art. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

Agents to alleviate constipation are well known in the art. In particular, combinations of opioids and agents to alleviate constipation are known in the art. For instance, see U.S. Pat. No. 6,982,283.

Opioid antagonists useful in the present invention may include, for example and without limitation, naltrexone, naloxone, nalmefene, nalide, nalmexone, nalorphine, nalorphine dinicotinate, cyclazocine, levallorphan, pharmaceutically acceptable salts thereof, and mixtures thereof. In certain embodiments, the opioid antagonist is naloxone or naltrexone. Typically the amount of antagonist included in a combination of the invention may vary with the analgesic or analgesics, the patient, and the source of the paint. In certain embodiments, the amount of the opioid antagonist included in the dosage form, may be about 10 ng to 275 mg. Those skilled in the art will also appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493. For instance, see U.S. Pat. No. 6,475,494 or U.S. Pat. No. 6,696,066.

(c) Pharmaceutical Compositions and Routes of Administration

Combinations of the invention may comprise a pharmaceutical composition. The agents of the invention may be formulated separately, or in combination. In some embodiments, the compositions may comprise pharmaceutically acceptable excipients. Examples of suitable excipients may include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The compositions may additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention may be formulated so as to provide quick, sustained or delayed release of the active ingredient after administration to a subject by employing procedures known in the art.

The active compounds of the invention may be effective over a wide dosage ranges and are generally administered in pharmaceutically effective amounts. It will be understood, however, that the amount of the compounds actually administered will be determined by a physician, in the light of the relevant circumstances, including the condition to be treated, the analgesic to be administered, the age, weight, and response of the individual patient, the severity of the patient's symptoms, and the like.

The tablets or capsules of the present invention may be coated or otherwise compounded to provide a dosage form affording the advantage of prolonged action. For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate as are known in the art.

The liquid forms in which the compositions of the present invention may be incorporated for administration include aqueous solutions, suitably flavored syrups, oil suspensions and flavored emulsions with edible oils such as cottonseed oil, sesame oil, coconut oil, or peanut oil as well as elixirs and similar pharmaceutical vehicles. Liquid dosage forms for oral administration may also include pharmaceutically acceptable emulsions, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

DEFINITIONS

As used herein, "subject" encompasses mammals with pruritus specific receptors on pruritus specific neurons. In one embodiment, subject refers to a mammal selected from the group comprising rodents, non-human primates, and humans. In another embodiment, subject refers to humans.

As used herein, "substantially," generally means greater than 50%. For example, "substantially inhibiting activation" means inhibiting greater than 50% of the activation compared to no inhibition. Similarly, "substantially impeding function" means inhibiting greater than 50% of the function compared to no impedance. In some embodiments, substantially may mean greater than 55, 60, 65, 70, 75, 80, 85, 90, or 95%. In other embodiments, substantially may mean greater than 95, 96, 97, 98, or 99%.

As used herein, "treating" means reversing, alleviating, inhibiting the progress of, or preventing pruritus, or one or more symptoms of such disorder or condition. The term "treatment", as used herein, unless otherwise indicated, refers to the act of treating as "treating" is defined immediately above. As used herein, "alleviating" means reversing, inhibiting the progress of, or preventing pruritus, or one or more symptoms of such disorder or condition.

As used herein, full opioid agonist refers to an agent that stimulates activity at opioid receptors in the brain that are normally stimulated by naturally occurring opioids. Examples of full opioid agonists include morphine, methadone, oxycodone, hydrocodone, heroin, codeine, meperidine, propoxyphene, and fentanyl.

As used herein, partial opioid agonist refers to an agent that can both activate and block opioid receptors, depending on the clinical situation. Under appropriate conditions, partial agonists can produce effects similar to those of either agonists of antagonists. Buprenorphine is a partial opioid agonist.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense

Example 1. Expression of GRPR in the Spinal Cord

Figure 1B:
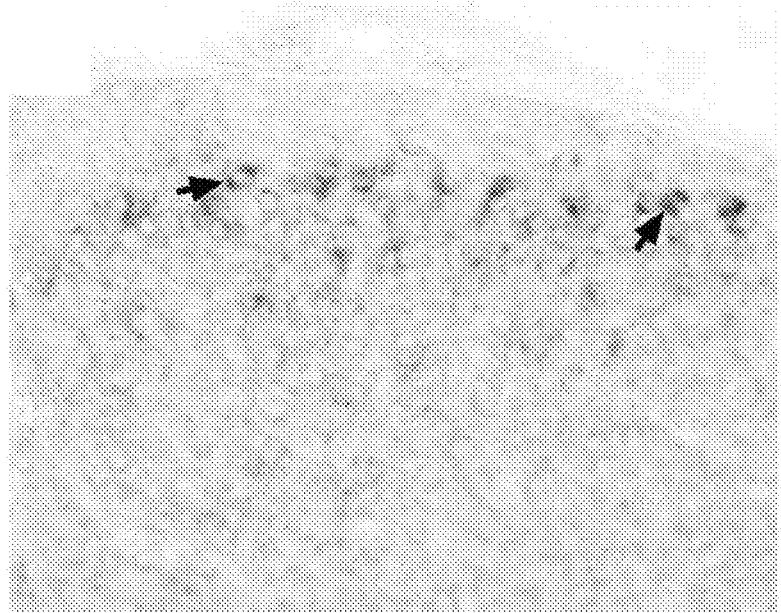

To identify novel genes that are expressed in the dorsal horn of the spinal cord, differential dorsal/ventral screening was performed (Li et al., 2006). The expression of the GRPR gene was found to be restricted to lamina I of the spinal cord (FIG. 1). GRPR expression is located in the most superficial layer of the dorsal horn (FIG. 1). No GRPR+ cells are found in the deep dorsal horn and ventral horn of the spinal cord. Such highly specific expression of a gene in lamina I but not in other regions of the dorsal horn is unprecedented. Because lamina I neurons have been implicated in pain and itch sensation, we postulated that GRPR+ neurons may be important for mediating the itch sensation.

Figure 2A:
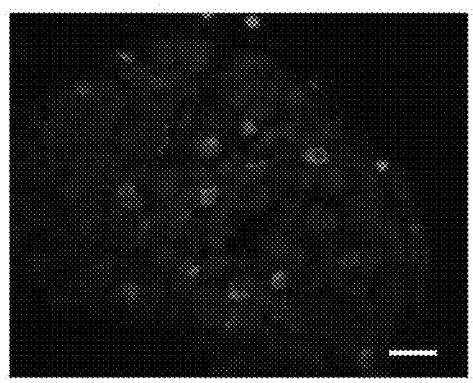
FIG. 2A-F depicts a series of photomicrographs showing GRP expression in DRG neurons. (A) GRP is detected in small-sized DRG neurons by immunohistochemistry. (B-E) Double-staining of GRP with peripherin (B), NF200 (C), IB4 (D) and CGRP (E). In (B), GRP (red) is localized in peripherin+ (green) DRG neurons. In (C), double-staining of GRP (red) and NF200 (green) in adult mouse DRG neurons indicates that GRP and NF200 expression do not overlap. In (D), GRP is present in adult DRG neurons labeled with a CGRP antibody (green in (E)) but not with IB4 (green in (D)). In (B) and (E), arrows indicate double-labeled neurons. In (F), GRP+ fibers (red) are located in lamina I and IIo of the dorsal horn, IB4 (green).
Figure 2B:
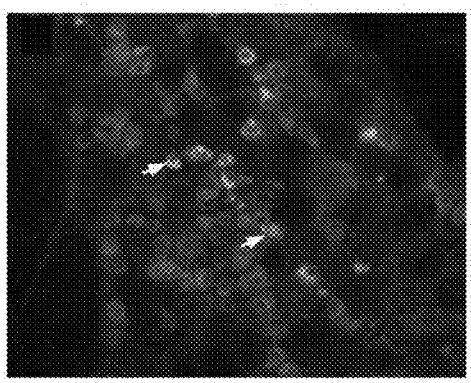
Figure 2C:
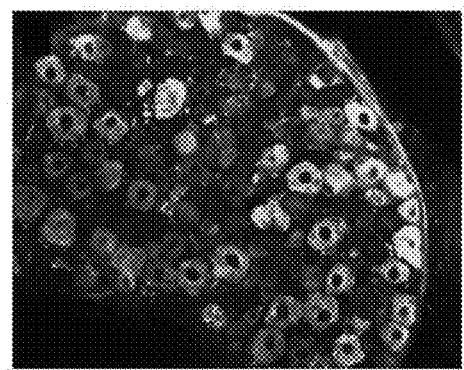
Figure 2D:
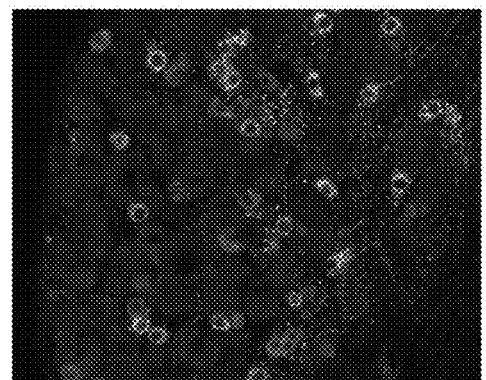
Figure 2E:
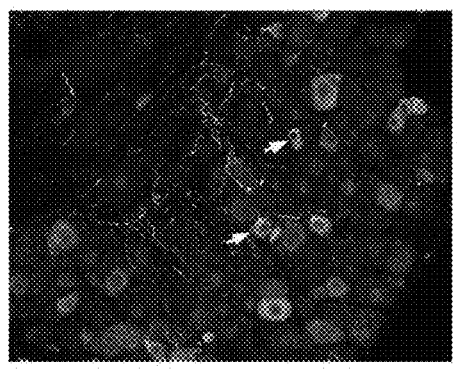
Figure 2F:
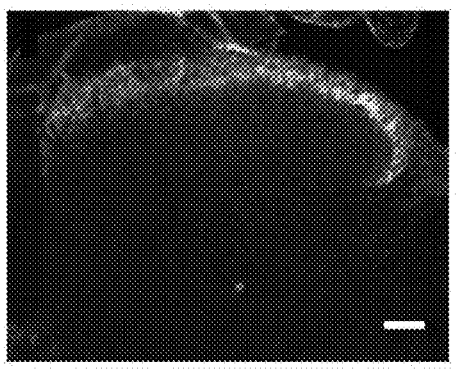

Example 2. Expression of GRP in a Subset of Peptidergic Dorsal Root Ganglion (DRG) Neurons GRP is expressed in a subset of small and medium sized DRG neurons (FIG. 2A), and is colocalized with peripherin, a marker for unmyelinated fibers (FIG. 2B). GRP is also colocalized with CGRP or substance P, but is neither costained with *Griffonia simplicifolia* isolectin B4 (IB4), a nonpeptidergic marker, nor with myelinated marker NF200 (FIG. 2C, D, E, data not shown). Furthermore, about 80% GRP+ neurons express TRPV1 in the DRGs (data not shown). GRP+ fibers project to the superficial layer (laminae I and II outer layers) of the dorsal spinal cord, to which SP+ fibers and CGRP+ fibers project (FIG. 2F). GRP mRNA is not found in the superficial layer of the spinal cord.

Figure 3A:
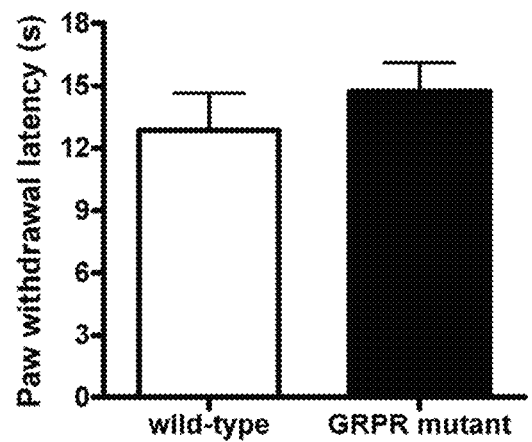
FIG. 3A-F depicts graphs showing pain behaviors were normal in GRPR mutant mice. (A-C) Responses to noxious thermal stimulation were measured by the paw withdrawal latency (Hargreaves test, (A)), hotplate (B) and the water immersion tail-flick latency (C). There were no significant differences in thermal pain responses between wild-type (n=8; white bars) and GRPR mutant mice (n=7; black bars). P>0.05, student's t-test. (D) Sensitivity to mechanical stimuli of GRPR mutant mice (n=7; black bars) as measured by paw withdrawal threshold upon exposure to von Frey filaments was comparable to wild-type mice (n=8; white bars). P>0.05, student's t-test. (E) Spontaneous pain responses in the first (0-10 min) and second phase (10-60 min) of the formalin test are comparable between wild-type (n=8; white bar) and GRPR mutant mice (n=9; black bars). P>0.05, student's t-test. (F) Locomotor activity measured by ambulation distance is comparable between wild-type (n=8; open circles) and GRPR mutant mice (n=7; filled circles). P>0.05, repeated measures analysis of variance (ANOVA). All data are presented as means±s.e.m.
Figure 3B:
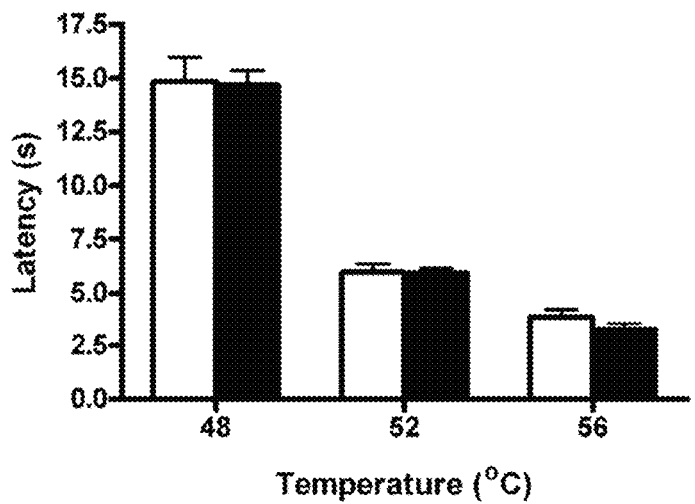
Figure 3C:
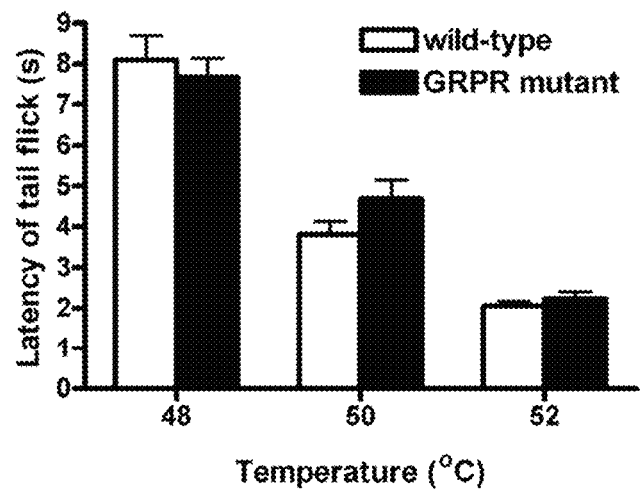
Figure 3D:
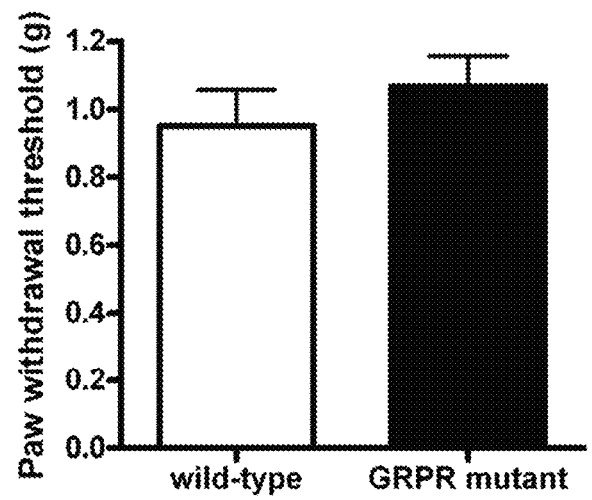
Figure 3E:
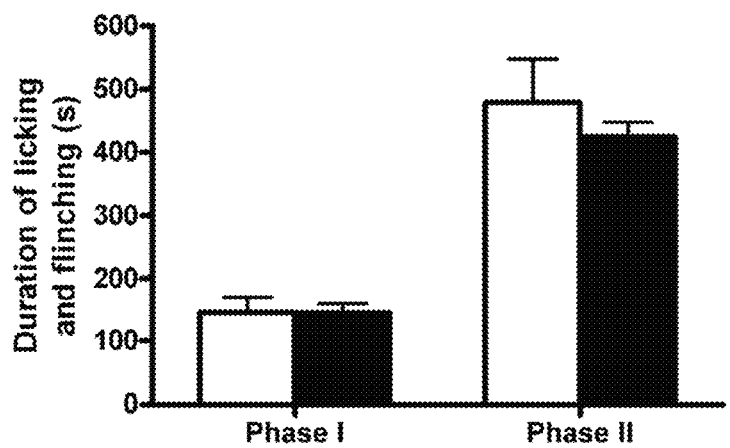
Figure 3F:
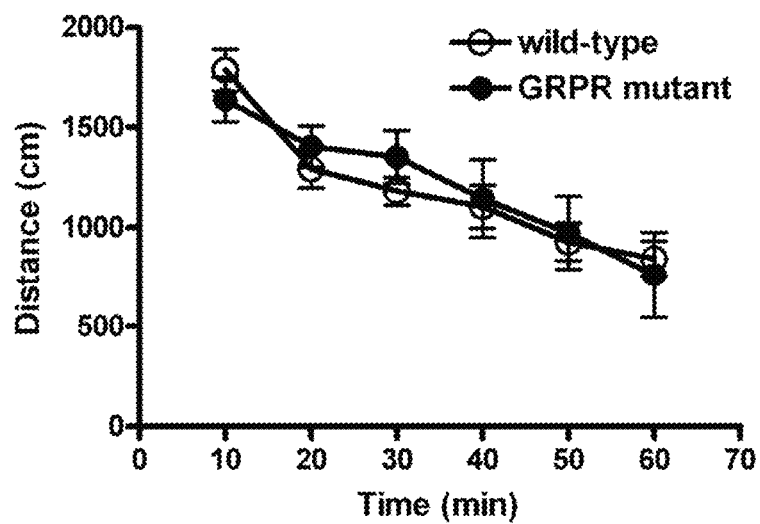

Example 3. Normal Locomotor Activity, Acute and Formalin Pain Behaviors of GRPR Mutant Mice To examine whether GRPR is required for locomotor activity, GRPR mutant and wild-type littermate mice were examined in an open field test. There was no significant difference in locomotor activity between the two genotypes (FIG. 3F). To assess whether GRPR may contribute to pain sensation, the thermal, mechanical, and inflammatory (formalin) pain responses of GRPR mutant mice were examined. We found the GRPR mutant mice and wild-type mice did not differ in any of the pain behaviors examined (FIG. 3A-E), suggesting that GRPR is not required for transmission of noxious information.

Figure 4A:
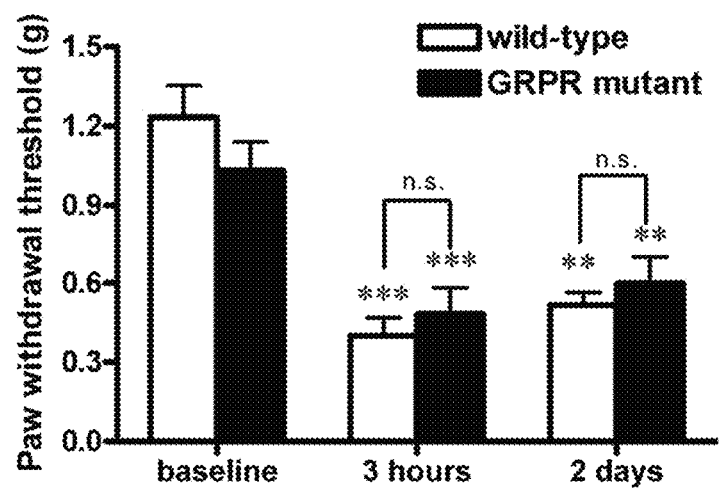
FIG. 4A-B depicts graphs showing GRPR is not necessary for persistent pain. (A) Mechanical sensitivity before (baseline), 3 hrs and 2 days following CFA injection was tested. Hyperalgesia induced by intraplantar injection of CFA (200 is comparable between wild-type (white bars) and GRPR mutant mice (black bars). n=6 for each group. Student's t-test, $P<0.01$, *$P<0.001$ versus baseline. All data are presented as means±s.e.m. CFA, complete Freund's adjuvant; n.s., no significant difference. (B) Mechanical sensitivity was tested before and after partial sciatic nerve injury. Mechanical allodynia of the ipsilateral hindpaw is comparable between wild-type (open circles) and GRPR mutant mice (filled circles). n=7 for each group. Repeated measures analysis of variance (ANOVA) comparing between groups, P>0.05. All data are presented as means±s.e.m.
Figure 4B:
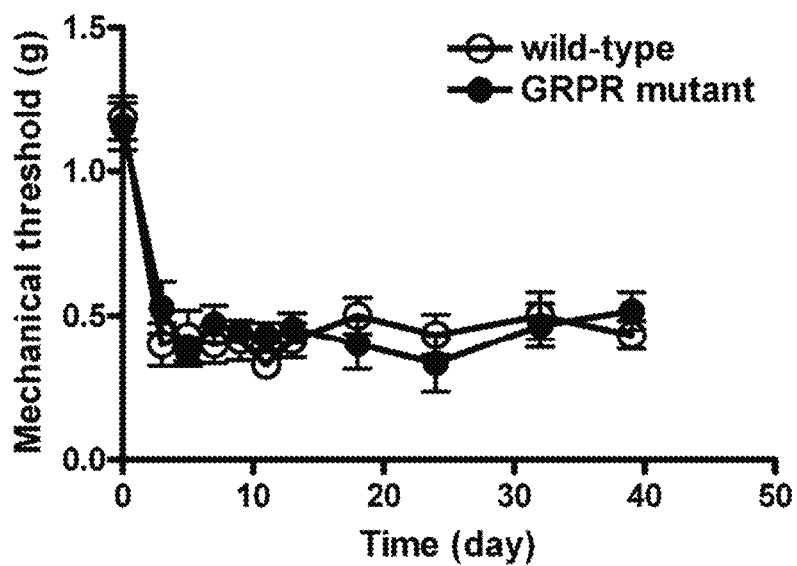

To further examine pain behaviors of GRPR mutant mice in persistent pain models, the mechanical hypersensitivity produced by hindpaw injection of complete Freund's adjuvant (CFA) was examined, and no significant difference was found between GRPR mutant and wild-type littermates (FIG. 4A). To examine if GRPR is required for neuropathic pain, the mechanical thresholds of GRPR mutant and wild-type mice were tested in the partial sciatic nerve injury model (Malmberg and Basbaum, 1998). Comparable mechanical hyperalgesia was found in ipslateral and contralateral sides of the injury between GRPR mutant and wild-type mice (FIG. 4B, data not shown).

To ascertain whether there is an alteration in the expression of pain-related genes in the dorsal horn, a number of pain-related genes were examined by immunocytochemistry and in situ hybridization studies, and no obvious difference in their expression was detected in the dorsal horn between GRPR mutant and wild-type littermate mice (FIG. 5, data not shown). Taken together, the behavioral and molecular analysis suggest that GRPR is not required for pain sensation.

Example 4. The Scratching Behaviors of Wild-Type and GRPR Mutant Mice

Figure 6A:
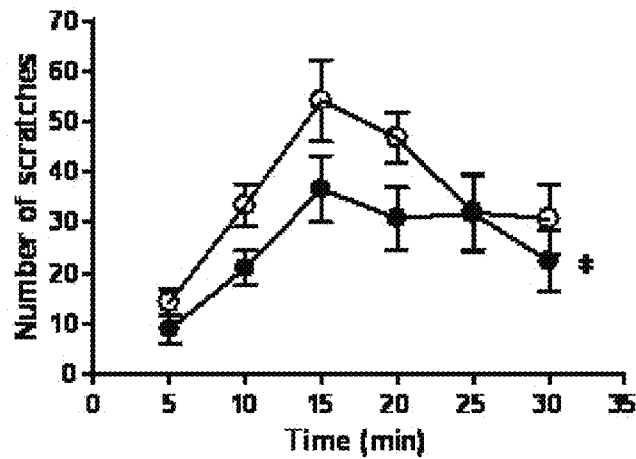
FIG. 6A-C depicts graphs showing scratching behaviors were reduced in GRPR mutant mice. (A) Scratching behavior induced by compound 48/80 is significantly decreased in GRPR mutant mice (n=17; filled circles) compared to wild-type mice (n=14; open circles). Repeated measures analysis of variance (ANOVA); *$P<0.05$. (B) Scratching behavior induced by the PAR2 agonist SLIGRL-NH2 in wild-type (n=11; open circles) and GRPR mutant mice (n=11; filled circles); GRPR mutant mice have a severely blunted response. ANOVA; *$P<0.05$. (C) The scratching behavior induced by chloroquine in wild-type (n=11; open circles) and GRPR mutant mice (n=11; filled circles); GRPR mutant mice showed significantly reduced response. ANOVA; **$P<0.01$. All data are presented as means±s.e.m.
Figure 6B:
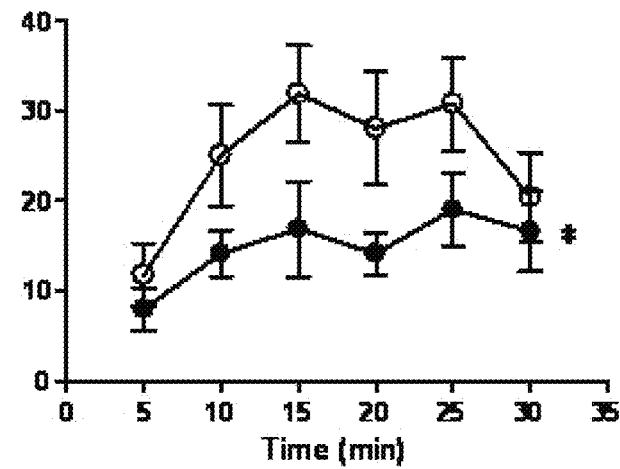
Figure 6C:
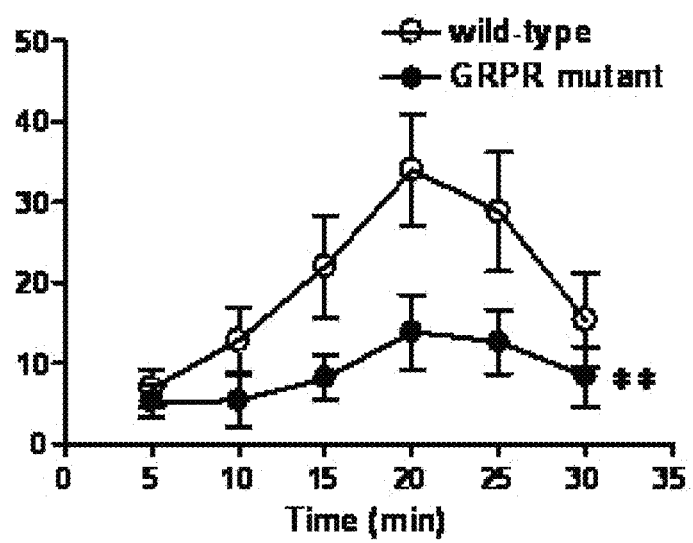

To ascertain whether GRPR is required for itch sensation, we studied the effects of several pruritogenic agents in GRPR mutant mice and wild-type mice. These pruritogens include compound 48/80 which degranulates mast cells, and releases histamine (Kuraishi et al., 1995), a protease-activated receptor 2 (PAR2) agonist (SLIGRL-NH2) which is a histamine-independent itch mediator (Steinhoff et al., 2003; Shimada et al., 2006), and chloroquine pan and Cowan, 2004; Green et al., 2006). In all tests, the scratching behavior induced by i.d. injection of these agents was significantly reduced in GRPR mutant mice compared to wild-type mice (FIG. 6).

Figure 7A:
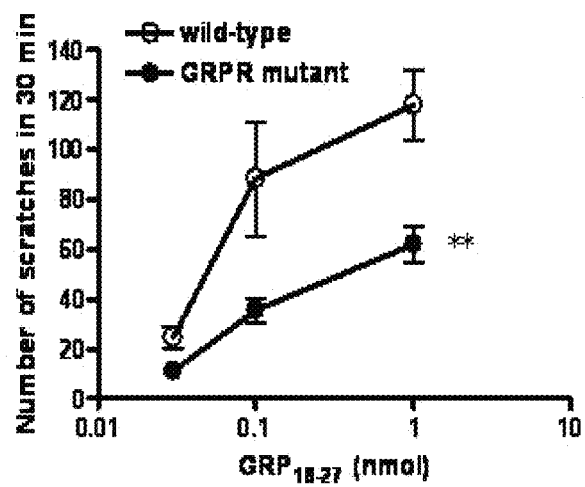
FIG. 7A-E depicts graphs showing the effect of GRPR agonist and antagonist on scratching behavior. (A) Scratching behavior is monitored after intrathecal (i.t.) injection of GRP18-27 (0.03, 0.1 or 1.0 nmol/5 μl). GRP18-27 induced dose-dependent scratching behavior in wild-type mice (n=7; open circles). The number of scratches was markedly reduced in GRPR mutant mice (n=7; filled circles) when compared to wild-type littermate controls. ANOVA; **$P<0.01$. (B) The effect of GRP18-27 (1.0 nmol/2.5 μl) was significantly blocked by i.t. injection of GRPR antagonist (D-Phe-6-Bn(6-13)OMe (1.0 nmol/2.5 μl), n=8; filled circles) compared with vehicle (n=8; open circles). ANOVA; *$P<0.05$. (C-E) Unlike the control group (white bars), intrathecal injection of the GRPR antagonist (black bars) significantly inhibited scratching behavior induced by i.d. injection of pruritogenic agents. *$P<0.05$, **$P<0.01$, Student's t-test.
Figure 7B:
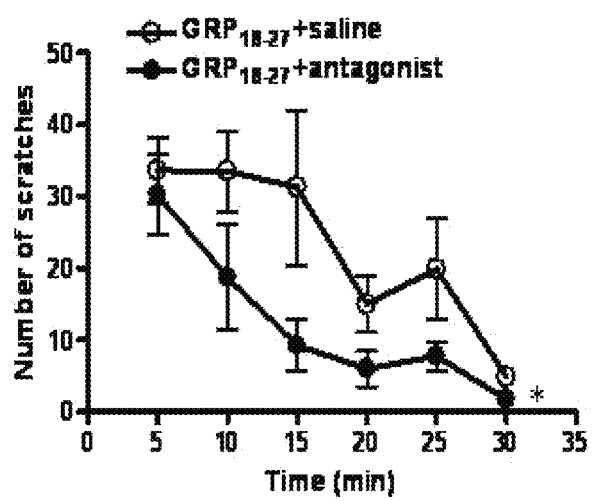
Figure 7C:
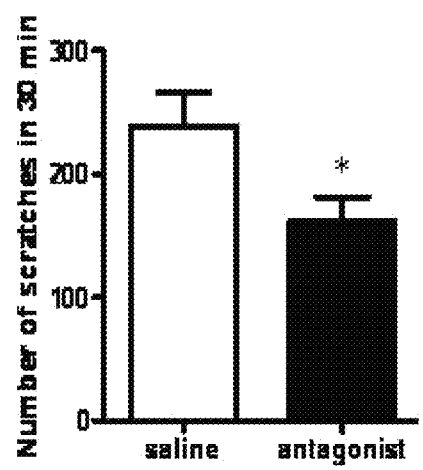
Figure 7D:
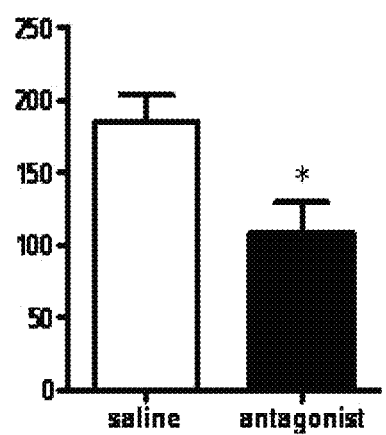
Figure 7E:
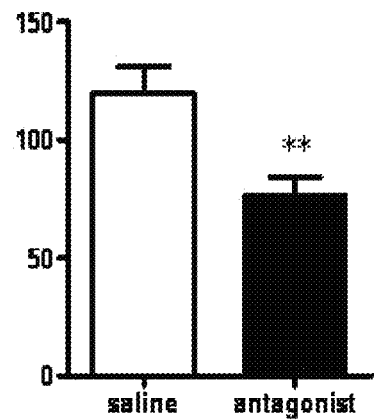

To determine whether an activation of GRPR in the spinal cord may facilitate the transmission of itch signals, which would subsequently result in increased scratching behavior, the GRPR agonist GRP18-27 was intrathecally administered (Ladenheim et al., 1996). Indeed, increased scratching behavior was found in a dose-dependent manner (FIG. 7A, data not shown). However, in GRPR mutant mice injected with this agonist intrathecally, the number of scratching behaviors were significantly lower (FIG. 7A). I.t. injection of the GRPR antagonist D-Phe-6-Bn(6-13)OMe (Wang et al., 1990) significantly inhibited GRP18-27-induced scratching behavior (FIG. 7B). I.t. injection of the GRPR antagonist 10 min before i.d. injection of each of the pruritogenic agents resulted in a significant reduction of the scratching behavior compared with saline control (FIG. 7C, D, E. These results suggest that GRP acts through spinal GRPR to mediate the transmission of information that drives scratching behavior in response to pruritogenic stimuli.

Figure 8A:
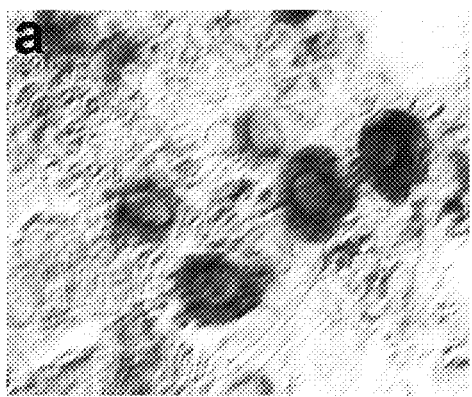
FIG. 8A-C depicts photomicrographs showing the expression of NMB in DRGs and NMBR in the superficial layer of the dorsal horn. (A) NMB is expressed in a subset of DRG neurons detected by in situ hybridization. (B) double-color in situ staining showing that NMB (green) is colocalized with CGRP (red) in DRGs. (C) NMBR mRNA is detected in the marginal zone of the superficial layer of the dorsal horn detected by in situ hybridization studies. The image shown in (C) is provided by St. Jude Children Research Hospital Brain Gene Expression Map (BGEM) database.
Figure 8B:
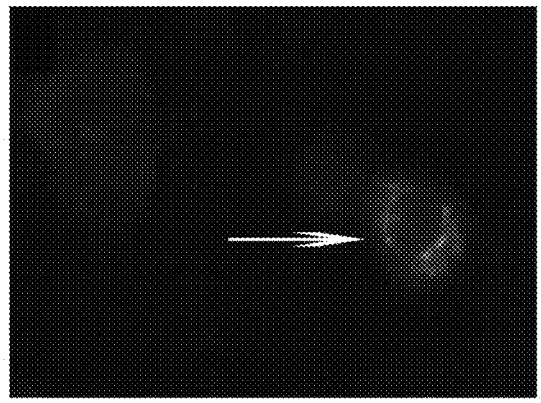
Figure 8C:
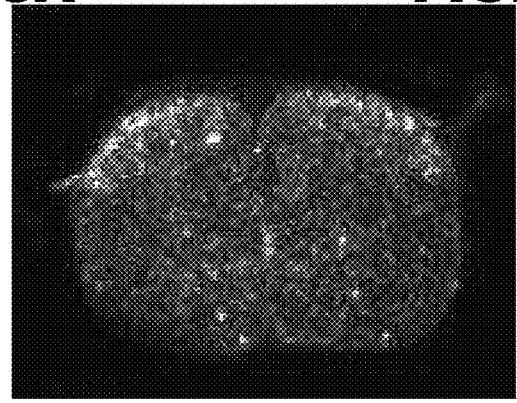

Example 5. Expression of NMB in DRG Neurons and NMBR in the Superficial Layer of the Dorsal Horn The second mammalian bombesin-like peptide NMB and its receptor NMBR appear to show similar expression pattern with that of GRP and GRPR. In DRG cells, NMB is expressed in a subset of neurons, which also express CGRP, indicating that NMB is expressed in a subset of peptidergic C-fibers (FIG. 8A, B, data not shown). In contrast, NMBR is expressed in the most superficial layer of the dorsal spinal cord (FIG. 8C). These expression patterns are consistent with previous literature (Namba et al., 1985; Wada et al., 1990).

Figure 9A:
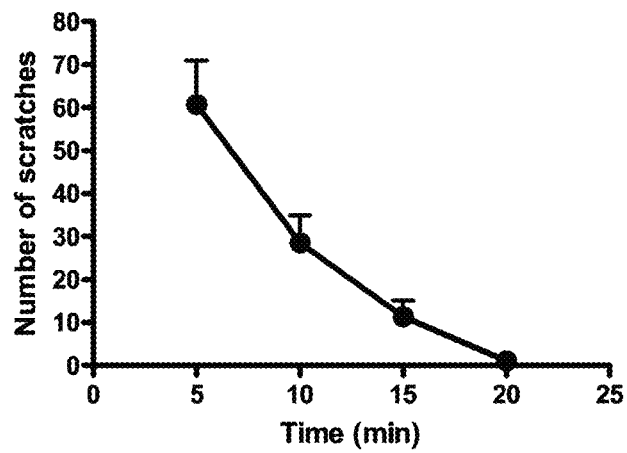
FIG. 9A-B depicts graphs showing the effect of intrathecal NMB on scratching behavior. (A) The scratching behavior is monitored over 20 minutes after i.t. injection of NMB (1.0 nmol/5 μl) in wild-type mice. i.t. injection of NMB induced robust scratching behaviors. (B) Dose response of NMB after i.t. injection, with saline as the vehicle control.
Figure 9B:
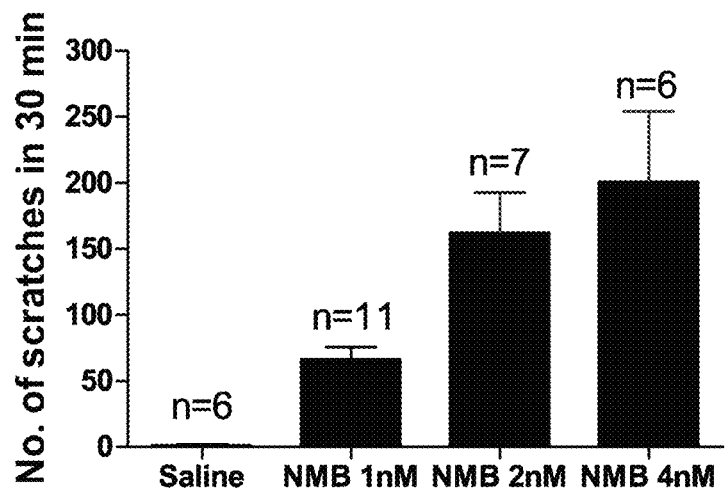
Figure 10:
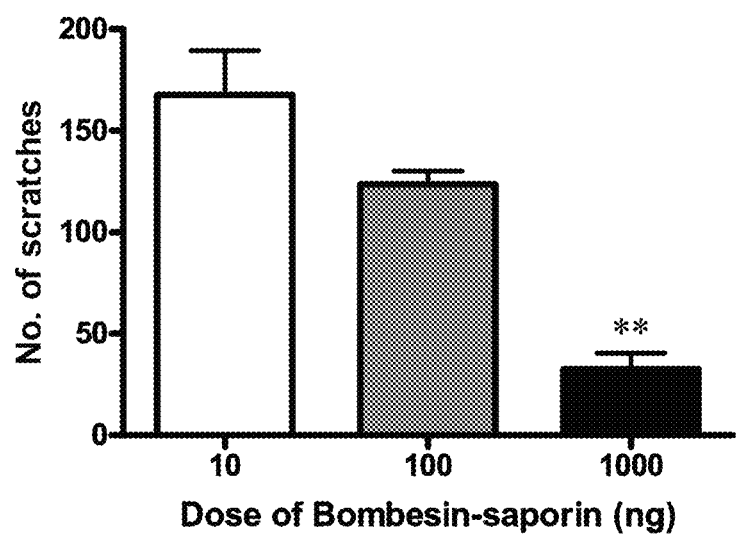
FIG. 10 depicts graphs showing scratching behaviors reduced after bombesin-saporin treatment. Three groups of mice received of 1 μg, 100 ng, or 10 ng of bombesin-saporin intrathecally at the volume of 5-ml. Two week after the treatment of bombesin-saporin, the mice were tested for GRP18-27-induced scratching behavior. The scratching behavior decreased dose-dependently. n=4-5 for each group. Student's t-test; **$P<0.01$, compared with 10-ng group. All data are presented as means±s.e.m.
Figure 11A:
Figure 11B:
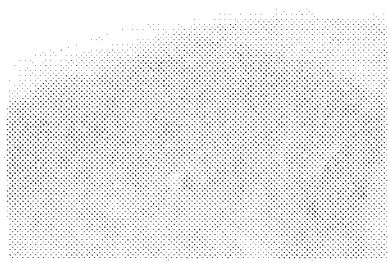
Figure 11C:
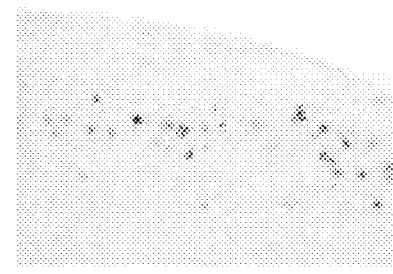
Figure 11D:
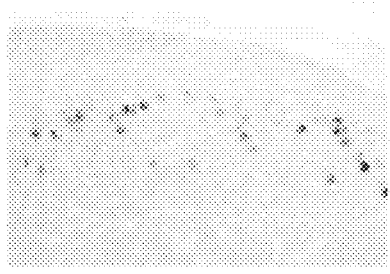
Figure 11E:
Figure 11F:
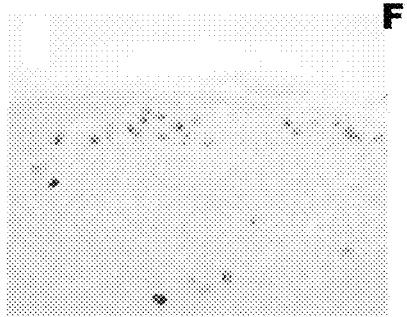

Example 6. The Effect of Intrathecal NMBR Agonist on the Scratching Behavior in Mice NMBR is a mammalian homologue of bombesin-like peptide receptors, and may have a role in mediating itching sensation in the spinal cord. To determine whether neuromedin B (NMB, an NMBR agonist) may mediate some scratching behaviors, we injected NMB into mice intrathecally. Similar to GRP, i.t. injection of NMB (1 nmol/5 μl) induced robust scratching behaviors in wild-type mice (FIG. 9). Because the scratching behaviors are not completely abolished in GRPR mutant mice, this raises the question of whether other bombesin-like peptide receptors such as NMBR may compensate for the loss of GRPR in the spinal cord. Indeed, our preliminary studies (FIG. 9) suggest such a possibility. GRPR and NMBR may have redundant functions for several reasons: 1. NMBR and GRPR share significant homology; 2. NMB is expressed in a subset of small DRG neurons and NMBR is expressed in the superficial layer of the spinal cord (FIGS. 8 and 10, data not shown) (Namba et al., 1985; Wada et al., 1990); 3. Intrathecal NMB induces scratching behavior; 4. In several species examined, GRPR and NMBR are all coupled to downstream intracellular signaling components including phospholipase C and are capable of stimulating tyrosine phosphorylation of some proteins such as p125FAK (Ryan et al., 1998).

Example 7. Confirmation of c-Ret-EGFP Mice in DRG Neurons and Their Projections in the Superficial Dorsal Horn Identification of GRPR and GRP as the itch genes paves the way for the molecular characterization of itch-related genes in the nervous system. Recently National Institute of Neurological Disorders and Strokes (NINDS) The Gene Expression Nervous System Atlas (GENSAT) BAC transgenic project at Rockefeller University has generated GRP-EGFP (GRP-enhanced green fluorescent protein) transgenic mice successfully (Gong et al., 2003). In GRP-EGFP mice, endogenous GRP coding sequence has been replaced by the sequence encoding EGFP protein and EGFP can be used as a molecular tag to label GRP+ cells. Images from GENSAT database showed that that GRP-EGFP+ fibers are present in the superficial layer of the dorsal horn. Although GRP-EGFP staining in DRG cells is not available from GENSAT, the fact that GRP-EGFP+ fiber staining in the superficial dorsal horn provides convincing evidence that GRP-EGFP expression mimics endogenous GRP expression. Moreover, GENSAT database also shows that GRP-EGFP staining in other brain regions of GRP-EGFP mice recapitulates the endogenous expression of GRP in the brain (data not shown), further validating the GRP-EGFP transgenic lines. The availability of GRP-EGFP mice makes it possible, for the first time, to sort GRP+ cells from other types of DRG cells. In contrast to GRP expression in peptidergic cells in the DRGs, c-Ret, a transmembrane signaling component of the receptor for glial cell-derived growth factor (GDNF), is only expressed in non-peptidergic, IB4+/GRP- cells (Molliver et al., 1997; Snider and McMahon, 1998) (FIG. 2). Dr. Jeff Milbrandt at Washington University, has generated c-Ret-EGFP knock-in mice, and expression of c-Ret-EGFP mimics that of endogenous c-Ret (Jain et al., 2006). Examination of EGFP in DRG cells of c-Ret-EGFP mice indicates that EGFP recapitulates endogenous c-Ret expression. It was also confirmed that GRP and IB4 are not coexpressed in DRG cells.

Example 8. To Test Whether i.t. Injection of NMB and NMBR Antagonist Can Modulate Scratching Behaviors in a Dose-Dependent Manner The scratching behaviors of GRPR mutant mice are not completely abolished in some itch models (FIG. 6). For example, in the compound 48/80 model, despite a significant reduction in scratching behaviors of GRPR mutant mice compared with wild-type controls, the mutant mice still scratched in response to itching stimuli (FIG. 6A). Moreover, i.t. injection of the GRPR agonist, GRP18-27, induced dose-dependent scratching behaviors, but GRP-induced scratching behaviors are not completely lost in GRPR mutant mice (FIG. 7A). These observations suggest that GRPR is not the only itch mediator in the spinal cord, and raise the possibility that GRP may cross-talk with other GRPR-like receptors in the spinal cord. A likely candidate is NMBR because it is the closest homologue of GRPR. Anatomically, NMB is expressed in a subset of small DRG cells and NMB+ fibers project to lamina I and II of the dorsal horn (FIG. 8) (Namba et al., 1985; Wada et al., 1990), whereas its receptor, NMBR, is expressed in the dorsal spinal cord (FIG. 8) (Wada et al., 1990). Indeed, preliminary studies indicated that i.t. injection of NMB is capable if inducing robust scratching behaviors (FIG. 9). These studies raise the possibility that NMBR may have compensated for the loss of GRPR in GRPR mutant mice in response to compound 48/80, and GRP may cross talk with NMBR to mediate itch transmission.

To confirm the efficacy of the NMBR antagonist (BIM 23127, Tocris), we will test whether BIM 23127 can inhibit the scratching behavior induced by i.t. injection of NMB, and determine the minimal dose needed to black this effect. Different doses of BIM 23127 (0.1, 0.3, 1.0 nmol/5 µl) diluted in saline or saline only (5 µl) will be injected 10 min before i.t. injection of NMB (1.0 nmol/5 µl), and the number of scratching responses will be counted for 30 min at 5-min intervals after injection. Another group of mice will receive the injection of BIM 23127 (1.0 nmol/5 µl) only to determine whether BIM 23127 itself can cause scratching behavior. All measurement will be performed by a person who is blinded to the experiment condition.

To examine the effect of the NMBR antagonist on the scratching behavior of mice, three animal models for itch will be used. a) compound 48/80 (100 µg, Sigma-Aldrich); b) chloroquine (200 µg, Sigma-Aldrich); c) and the PAR2 agonist SLIGRL-NH2 (100 µg, Bachem). Each pruritogenic reagent is dissolved in saline, in a volume of 50 µl. Saline is injected into different group of mice as the control. Two days before experiments, a 1.5 cm diameter circular area is shaved at the back of the neck where i.d. injections are given. Then the mouse is placed in a small plastic chamber (9×9×13 cm) for 60 min for acclimation prior to experiments. Either NMBR antagonist or saline will be injected intrathecally 10 min before i.d. injection. Immediately after i.d. injection of the pruritogenic agent into the rostral part of the back, mice will be placed back into the same cage for the observation of scratching of the injection site by a hind paw (Maekawa et al., 2000). The mice will be videotaped, beginning 15 min prior to i.d. injection, for later counting of hind paw scratching behavior directed towards the shaved area at the back of the neck.

All the behavioral experiments will be performed by a person who is blinded to the experimental condition. Statistical analyses will be performed using the repetitive ANOVA to compare the effect of NMB or NMBR antagonist with saline group. These comparisons will be made by the use of Prism Software (GraphPad, San Diego, Calif.) and STATISTICA 7 (StatSoft, Tulsa, Okla.). Data will be expressed as the mean±s.e.m, and $p<0.05$ will be considered statistically significant.

Example 9. To Examine the Scratching Behaviors of NMBR Mutant Mice and Wild-Type Littermate Control Mice NMBR heterozygous mice have recently been obtained from Dr. Hiroko OHKI-Hamazaki in Japan and are being bred to generate NMBR mutant mice in our facility. These mice exhibited normal locomotor activity and were fertile (Ohki-Hamazaki et al., 1997), and thus should be valuable for assessing the requirement of NMBR in itch sensation. Mice will be genotyped by PCR as described (Ohki-Hamazaki et al., 1997). For each pruritogenic agent, ten NMBR mutant male mice and 10 wild-type littermate control mice will be used. Three sets of experiments will be performed using three different pruritogenic agents (compound 48/80, PAR2 agonist and chloroquine) as described above. Injection of these pruritogenic agents and the examination of the scratching behaviors of these mice will be performed according the procedure described in Experiment 8. Statistical analyses will be performed using the repetitive ANOVA as described in Experiment 8. All of the experiments will be performed by a person who is blind to the genotype and treatment.

Example 10. To Determine Whether There is a Functional Overlap Between GRPR and NMBR in Itch Transmission by Examining Scratching Behavior of NMBR/GRPR Double Mutant Mice In mammals, often a member of a gene family may substitute for the loss of the function of one of their own members. The mechanism of functional redundancy may provide a safeguard against inadvertent loss of one of their own, and ensure the survival of the animals. GRPR and NMBR are members of mammalian bombesin-like receptor family, and share 56% homology of amino acid sequence. Moreover, the compounds that bind to NMBR also bind to GRPR with a lower affinity (Ryan et al., 1999). In GRPR mutant mice, some scratching behaviors remain in response to pruritogenic stimuli, suggesting that NMBR may compensate for the loss of GRPR in the spinal cord. This possibility can be critically tested by examining the scratching behaviors of GRPR/NMBR double knockout mice, and comparing them with GRPR or NMBR single knockout mice as well as wild-type littermate controls. Regardless of whether NMBR mutant mice show abnormal scratching behaviors in experiment 9, this genetic experiment will help understand the relationship between GRPR and NMBR in the spinal circuitry.

NMBR/GRPR double heterozygous mice will be generated by mating NMBR mutant mice with GRPR mutant mice. NMBR/GRPR double heterozygous mice then will be mated with each other to generate NMBR/GRPR double mutant mice. Because of a low percentage of double mutant mice in one litter, several litters within two weeks of period will be pooled for the experiment. To ensure that the results are comparable in similar genetic background, in addition to GRPR/NMBR double mutants, GRPR and NMBR single mutant mice will also be used for behavioral comparison. Mice with other combination of genotyping such as double heterozygous mice will be tested in pilot experiment to confirm they exhibit normal scratching behaviors like their wild-type littermates do. In all experiments, only male mice will be used, and age of the mice will be similar.

The scratching behavior of GRPR/NMBR double mutant mice will be examined using compound 48/80, PAR2 agonist SLIGRL-NH2 and chloroquine. The scratching behaviors will be induced by i.d. injection of pruritogenic agents, and the number of scratches will be recorded, counted and compared between GRPR single mutant mice, NMBR single, GRPR/NMBR double mutant and wild-type mice. Experimental protocols will be as the same as those described in Experiment 8. Data analysis will also be the same as described in Experiment 8.

Example 11. To Identify Candidate Itch Genes in GRP+ Cells by Performing Differential Screening Between GRP+ Cells and c-Ret+ Cells in DRGs Rapid progress has been made in identifying the receptors such as the transient receptor potential (TRP) channels involved in pain and temperature sensation during the past several years (Tominaga and Caterina, 2004; Wang and Woolf, 2005). In contrast, few itch genes have been found. Several reasons may have hindered the progress in studies of molecular machinery that controls itch sensation: First, our lack of understanding of itch-specific neuronal pathways is an obstacle for molecular study of the itch genes. In fact, the difficulty of identifying itch-specific neurons has made the molecular cloning of itch-specific genes using the differential screening strategy, a common technique for cloning tissue-specific genes, almost impossible. Second, the genes that have been implicated in itch sensation are often implicated in pain, making it difficult to dissociate the itch genes from the pain genes. Third, the lack of adequate animal models and a great variability in animal behavioral tests also represent a problem (Green et al., 2006). Finally, while knockout mice lacking genes expressed in the nociceptive pathway have been routinely examined for potential defects in pain behaviors, it has not been so for itch-related behaviors. Identification of GRP and GRPR as "itch genes" should provide an opportunity for molecular cloning of itch-related genes in GRP+ or GRPR+ cells.

In this experiment, the genes that are expressed in GRP+ cells in DRGs will be identified. There are several compelling reasons for us to use GRP+ DRG neurons as a starting point for molecular cloning of itch-related genes: 1). Our studies suggest that GRP+ sensory neurons mediate the transmission of itch signals from the skin to the spinal cord. In line with this, GRP is expressed in a rare subset of small-diameter, unmyelinated C-fibers which project to lamina I and IIo (outer layer) of the dorsal horn. This expression pattern is in accordance with what we know about the itch neuronal pathway (Schmelz, 2001; Davidson et al., 2007). The finding that only approximately 8% of total DRG cells express GRP (FIG. 2) makes these cells a unique population for identifying their underlying molecular signature. 2). The genetic tools for isolating GRP+ cells are now available (FIG. 10A), thereby making tissue-specific molecular cloning feasible. EGFP as an intracellular reporter is a very useful tool for flow cytometric separation of different populations of cells and therefore can be exploited to sort EGFP+ cells from EGFP- cells (Bhattacherjee et al., 2004). 3) Rapid improved gene-chip technology now only requires a minimal amount of cRNA (and thus very small number of cells) for hybridization. In addition, GRP-EGFP mice are available in MMRRC at University of California, Davis, a NIH-sponsored service. We are currently in the process of importing GRP-EGFP mice from MMRRC to our facility at Washington University.

Because of the difficulties of dissociating adult DRG neurons due to abundance of fibers in DRGs, P0 DRGs will be used for dissecting DRG out from mice. In addition, no co-expression of GRP and IB4 is found at this stage. Because of a low percentage of GRP+ cells, approximately 8 GRP-EGFP mice will be used for sampling. In contrast, c-Ret+ expression is much more abundant than GRP in DRG cells (about 60-70% of total DRG cells), and thus one c-Ret-EGFP mouse will be used for sampling. The DRGs will be dissected out, and kept in 1% Fetal Calf Serum (FCS) for nutrition at 4° C. To generate goodyields for cell sorting, the DRGs will be dissociated in 0.1% trypsin and resuspended into single cell suspension in Hank's Balanced Salt Solution (HBSS) with no calcium or magnesium, and no phenyl red. The suspension will be filtered through a 40-50 micron cell strainer (B-D Falcon 352340). Except for the digestion step, the sample will be kept cold at all times to minimize RNA degradation and cell death. Washington University provides an excellent facility for cell sorting, and it is expected that GRP+ and c-Ret+ cells will be isolated. Total RNAs are prepared from sorted from GRP-EGFP+ cells and c-Ret-EGFP+ cells respectively by using RNA-Bee reagent (Tel-Test, Friendswood, Tex.). Total RNAs are further obtained using the RNeasy mini kit (Valencia, Calif.), and the quality of RNAs is assessed by agarose gel electrophoresis. cDNA will be made from GRP-EGFP+ cells and c-Ret-EGFP+ cells respectively followed by RT to make cRNA for subtractive screening.

GRP+ and c-Ret+ cDNAs for subtractive hybridization are prepared using smart PCR cDNA Synthesis Kit (Clontech). GRP+ and c-Ret+ cDNA subtractions will be performed using Clontech PCR-Select cDNA subtraction Kit (Clontech). In forward subtraction, GRP+ cDNA (tester) will be suppressed by excess c-Ret+ (driver) to enrich GRP+ high cDNA. In reverse subtraction, GRP+ cDNA (tester) is suppressed by excess c-Ret+ cDNA (driver) to enrich c-Ret+ cDNA. The subtracted forward products, which enrich GRP+ cDNA will be subcloned into PCRII vector using TA Cloning Kit (Invitrogen, Life technologies) and transformed into TOP10F' competent *E. coli* to construct subtracted GRP+ cDNA library as described (Li et al., 2006).

Picked clones will be randomly selected from the subtracted GRP+ cDNA library. Differential screening will be performed according to the manual in the PCR-Select Differential Screening Kit (Clontech) as we have previously described (Li et al., 2006). In brief, the insert of each clone will be amplified and quantified. About 20-30 ng PCR product will be dissolved in denaturation solution at a 1:1 ratio and dotted on a nylon membrane (Hybond-XL, Amersham). Hybridizations will be performed with both subtracted and unsubtracted GRP+ and c-Ret+ probes, which are labeled with [$^{32}$P] dUTP by using Prime-a-Gene Labeling system (Promega). Candidate clones showing GRP+ hybridization signals will be selected and sequenced by the WUSTL Sequencing Core facility (St. louis, Mo.). Sequences will be identified in GenBank.

Tissue collection and the isolation of GRP+ and c-Ret+ cells will be the same as described above. Total RNA will be isolated from the spinal cords using Trizol RNA extraction protocol (available from Invitrogen). The quality of total RNA is critical for the success of microarray experiment. To ensure the high quality of total RNA, a small amount of total RNA will be subjected to spectrophotometric and electrophoretic analysis. Only total RNA with high quality will be used for further experiments. cRNA targets for microarray analysis will be generated according to the Affymetrix Genechip Expression Analysis Manual (Affymetrix, Santa Clara, Calif.). Briefly, double-stranded cDNA will be synthesized from 5.0 µg of total RNA directly using Gibco-BRL's SuperScript choice system. cDNA will be purified using phenol/chloroform extraction with Phase Lock Gel (Eppendorf) and concentrated by ethanol precipitation. In vitro transcription will be performed to produce biotin-labeled cRNA using a BioArray High Yield RNA Transcription Labeling Kit (Enzo Diagnostics). Affymetrix murine expression MOE430 sets, which contain approximately 45,000 probe sets, will be hybridized with labeled GRP+ and c-Ret+ cRNA targets. Hybridization, washing and scanning of Genechips will be carried out on an Affymetrics Fluidics Station following the standard procedures at the WUSTL Genechip Facility (St. Louis, Mo.). The arrays will be washed and stained using a fluidics system with streptavidin-phycoerythin (Molecular Probes), amplified with biotinylated anti-streptavidin antibody (Vector laboratories), and then scanned with a GeneArray Scanner (Affymetrix). A total of three independent GRP+ and c-Ret+ hybridizations will be carried out to reduce the experimental variations. These are standard techniques that we have previously used (Li et al., 2006).

The CEL files will be obtained with Affymetrix Microarray Suite software. DNA-Chip Analyzer (dChip, version 1.3. Harvard) (Li and Wong, 2001) will be used to normalize all CEL files to the baseline arrays, compute the model-based expression (PM-only model), and import the normalized values into Microsoft Excel where probe sets absent from all chips will be removed. The fold change (FC) in GRP+ expression for each probe set will be calculated using Excel. Significance analysis of microarrays (SAM) (Tusher et al., 2001) will be applied to analyzing the expression difference between GRP+ and c-Ret+ probe sets. Candidate genes will be filtered out by the use of two criteria: FCs>1.5 and SAM with false discovery rate (FDR)<0.05. Multiple probe sets representing a single gene transcript will be combined into one data point using NetAffyx and Genebank in order to reduce duplicate candidate genes. To validate whether our approach works, we will examine whether GRP is among those genes, which show the highest ratio between GRP+ and c-Ret+ cells. If GRP or other peptides known to be expressed in peptidergic neurons are present in the top of the gene list for GRP group identified in microarray, it should validate the microarray results.

The genes which show fold-change above the cut-off line between GRP+ cells and c-Ret+ cells will be subcloned by PCR. To amplify the gene of interest, the primers flanking about 1 kb cDNA sequence will be designed based on the sequence information in GeneBank. Amplified PCR fragments will be subcloned into pREM-T vector (Promega) and sequenced for confirmation. Once it is confirmed, the subcloned plasmids will be used as templates for synthesizing anti-sense RNA probes by in vitro transcription using T7 RNA polymerase. Sense probes will be synthesized as a control for non-specific signals. Digoxigenin-labled RNA probes will be made and hybridized as described (Birren et al., 1993). In our hands, approximately 30-40 candidate genes can be screened simultaneously within one week (Li et al., 2006). The expression of these genes in the DRG cells will be examined by the use of in situ hybridization.

Once the gene is confirmed to be expressed in a subset of DRG cells, we will determine whether the candidate gene is colocalized with GRP by in situ hybridization followed by immunostaining using anti-GRP antibody. This technique has been routinely used in our lab to verify the gene expression (Li et al., 2006). Using this approach, we should be able to validate whether the candidate genes are indeed expressed in GRP+ cells.

Example 12. Saporin Damage to Pruritus Specific Neurons

Three groups of mice were given bombesin-saporin (Advanced Targeting Systems, CA), at the dose of 1 microgram, 100 ng, 10 ng, intrathecally at the volume of 5-µl. Two weeks after the bombesin-saporin treatment, the mice were tested for GRP18-27-induced scratching behavior. The scratching behavior was obviously reduced dose-dependently. (See FIG. 10) The depletion of GRPR positive neurons are confirmed by in situ hybridization. (See FIG. 11) Other markers of the superficial dorsal horn are normal.

Example 13. Selective Ablation of GRPR+ Neurons by Bombesin-Sap

Bombesin, originally isolated from frog skin, is an exogenous agonist of high affinity for GRPR and bombesin-saporin (bombesin-sap), a toxin-coupled to bombesin, can bind and kill $GRPR^+$ neurons upon its internalization after intrathecal injection into the spinal cord. In example 8, $GRPR^+$ neurons in the spinal cord were selectively ablated and itch and pain behaviors of these mice was assessed.

Figure 12A:
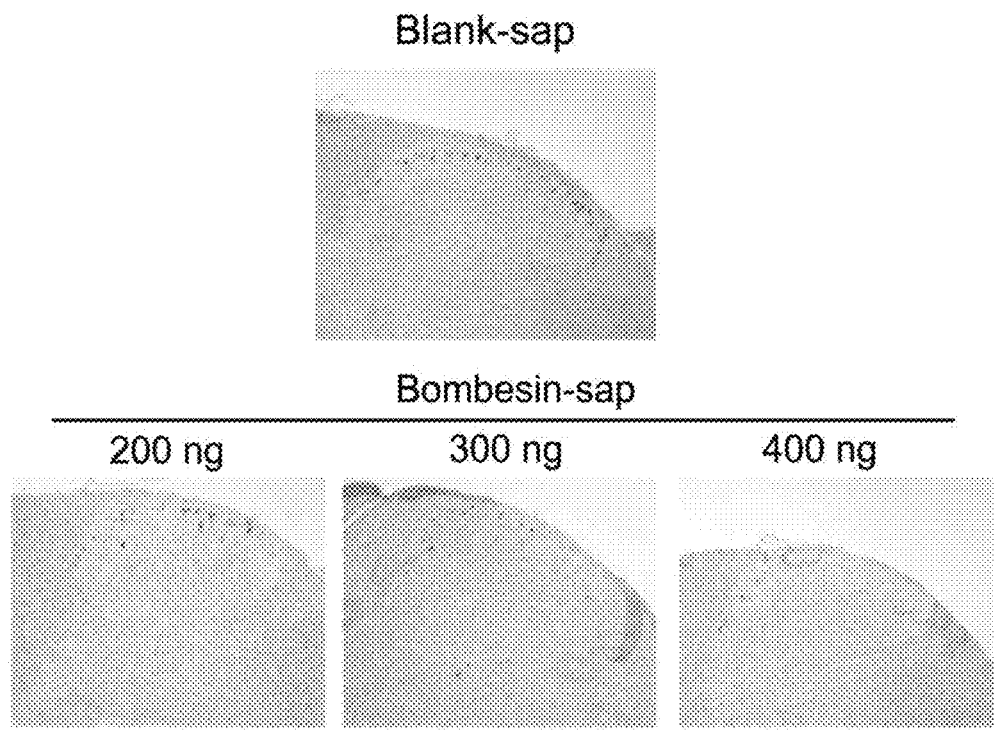
FIG. 12A-D depicts dose and time course effect of bombesin-saporin. (A) GRPR expression detected by in situ hybridization in the superficial spinal cord of mice at 2 weeks after intrathecal injection of blank-sap (400 ng) or bombesin-sap (200, 300, 400 ng). GRPR expression decreased when the dose of bombesin-sap increased. (B) The number of GRPR+ neurons decreased dose-dependently 2 weeks after intrathecal injection of bombesin-sap. (C) GRPR+ neurons were counted in two groups of mice at 2 or 4 weeks after the intrathecal injection of bombesin-sap (400 ng), respectively. No significant difference was found in the number of GRPR+ neurons between 2 weeks and 4 weeks groups. P>0.05. (D) The number of scratches elicited by i.d. chloroquine (200 μg/50 μl) decreased dose-dependently after treatment of bombesin-sap. $P<0.01$, *$P<0.001$ compared to the blank-sap group. Scale bar: A, 100 μm (A-D). n=2-4 for each group. Sap, saporin. Student's t-test.
Figure 12B:
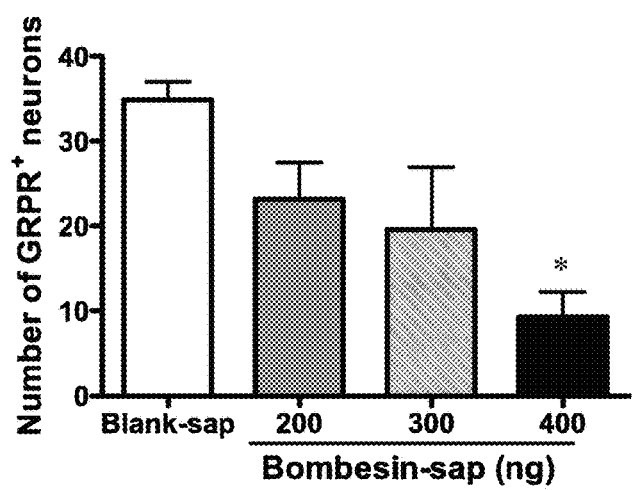
Figure 12C:
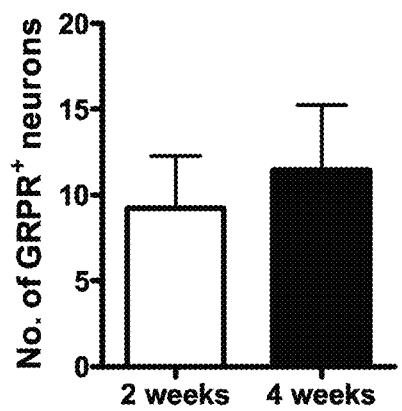
Figure 12D:
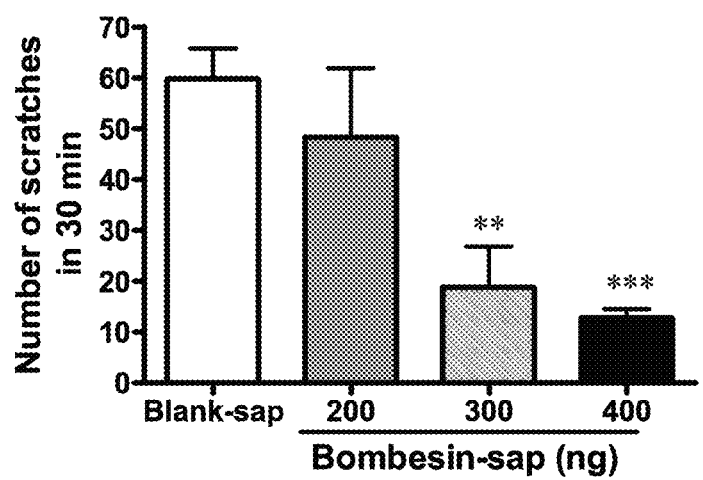
Figures 13G, 13H:
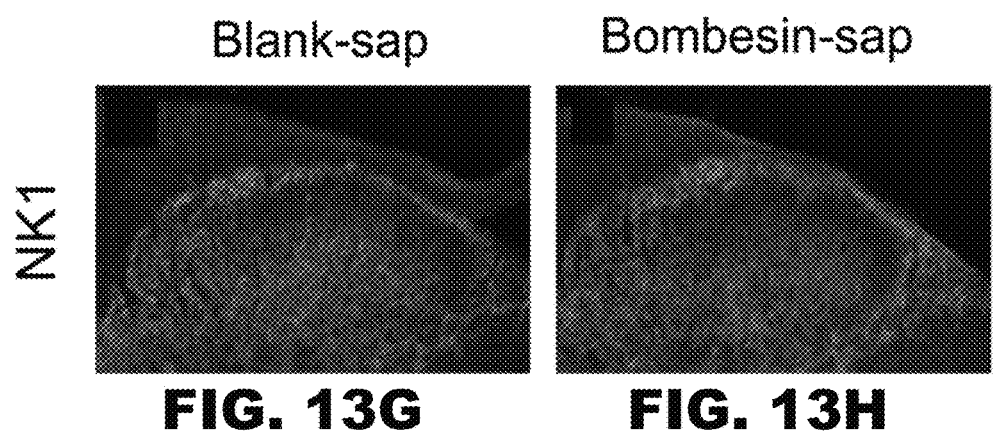
FIG. 13A-O depicts selective ablation of GRPR+ neurons in the spinal cord. (A to O) Comparison of molecular expression detected by in situ hybridization or immunocytochemistry and of the number of cells expressing the markers (C, F, I, L and O; black bars: bombesin-sap group; white bars: blank-sap group) in the superficial spinal cord of mice treated with intrathecal blank-sap (A, D, G, J, M) and intrathecal bombesin-sap (B, E, H, K, N). (A and B) GRPR expression in lamina I detected by in situ hybridization; (C) The number of GRPR+ neurons in the bombesin-sap group decreased significantly compared to the blank-sap group (**P<0.01). (D and E) NMUR2 expression in lamina I detected by in situ hybridization. (F) Similar numbers of NMUR2+ neurons between the bombesin-sap and blank-sap groups (P>0.05). (G and H) NK1 expression in the dorsal spinal cord detected by immunocytochemistry. (I) The density of NK1 signal in lamina I was comparable between the bombesin-sap and blank-sap groups (P>0.05). (J and K) PKCg in lamina IIi layer detected by immunocytochemistry. (L) The numbers of PKCg+ neurons are comparable between groups (P>0.05). (M and N) Neurotensin expression in Lamina II detected by in situ hybridization. (O) Comparable numbers of neurotensin+ neurons between the bombesin-sap and blank-sap groups (P>0.05). Scale bar: A, 100 μm (A and B, D and E, G and H, J and K, M and N). Student's t-test. n=4-6 for each group. Sap, saporin. Error bars represent s.e.m.
Figure 14A:
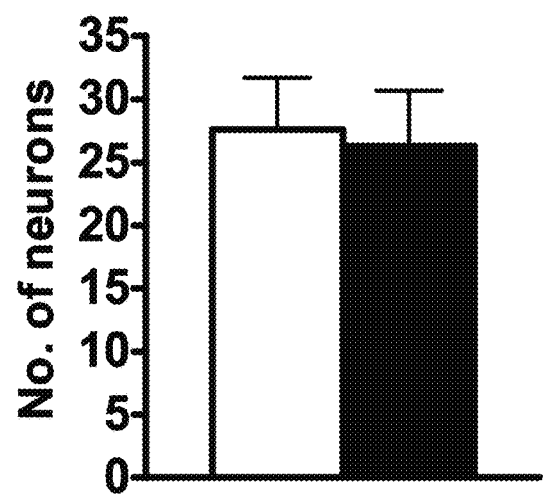
FIG. 14A-E shows that intrathecal injection of blank-sap did not cause toxic effect. (A and B) The numbers of GRPR+ (A) and NMUR2+ (B) neurons in blank-sap group (black bars) were comparable to the saline group (white bars, P>0.05). (C) The density of NK1 signal was not significantly affected by the treatment of blank-sap (black bar) compared with the saline group (white bar, P>0.05). (D and E) The numbers of PKCγ+ (D) and neurotensin+ (E) neurons in blank-sap group (black bars) are comparable to the saline group (white bars, P>0.05). n=4-6 for each group. Sap, saporin. Student's t-test.
Figure 14B:
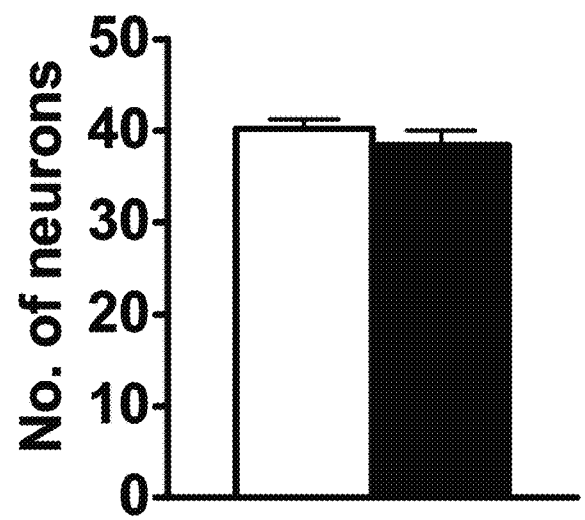
Figure 14C:
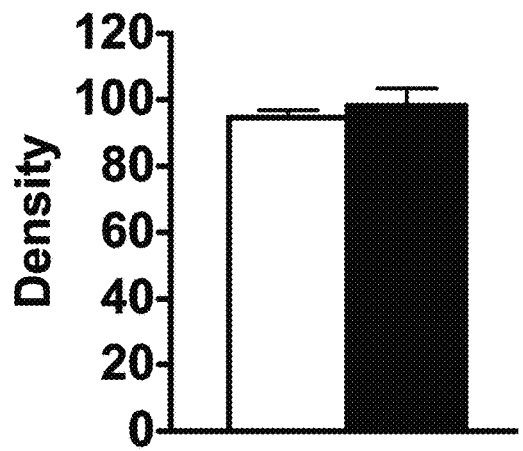
Figure 14D:
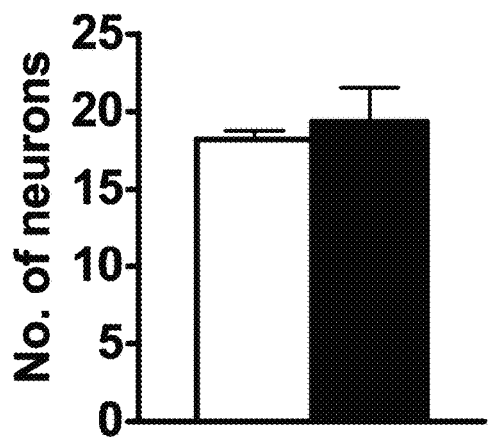
Figure 14E:
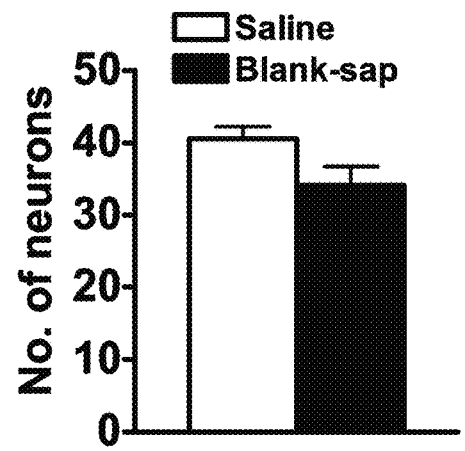

To employ the bombesin-sap ablation approach in mice, the dose of bombesin-sap and time points that were appropriate for intrathecal injection were first assessed using blank-sap, in which saporin is conjugated to a peptide of random sequence, as the controls. Mice treated with a single injection of bombesin-sap using three different doses (200 ng, 300 ng and 400 ng) showed reduced scratching behaviors in response to intradermal (i.d.) injection of chloroquine, a histamine-independent pruritogenic agent, as well as a dose-dependent decrease of $GRPR^+$ neurons as detected by in situ hybridization in the spinal cord compared with blank-sap (FIG. 12). At 400 ng, after two weeks of injection more than 80% of the $GRPR^+$ neurons were ablated (FIG. 13A to C), and this number of $GRPR^+$ neurons remained relatively same after 4 weeks of treatment (FIG. 12C). The number of GRPR+ neurons was similar between the control groups treated with blank-sap or saline (FIG. 14A). Moreover, no severe behavioral abnormalities were noted in bombesin-sap treated mice. Therefore, bombesin-sap at 400 ng with two weeks of treatment was chosen in all the experiments.

Figure 13I:
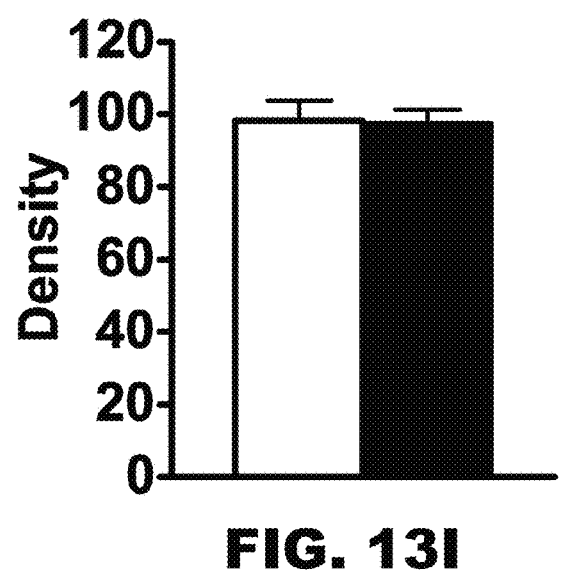

To determine whether bombesin-sap might ablate other subsets of cells in the dorsal horn, different populations of the superficial dorsal horn neurons were analyzed using lamina-specific markers. Expression of neuromedin U receptor 2 (NMUR2), a marker for a subset of lamina I neurons in the spinal cord, was not affected in mice treated with bombesin-sap (FIG. 13D-F). Expression of dynorphin, another lamina I-specific marker, was also unchanged (data not shown). Neurokinin 1 receptor (NK1) is primarily expressed in lamina I and ablation of $NK1^+$ neurons in the spinal cord by substance P-sap reduced the persistent but not acute pain responses in rats. $NK1^+$ signals in lamina I did not change as assessed by density of the fluorescence signal after immunocytochemistry (FIG. 13G-I). Expression of lamina II markers such as neurotensin and PKCγ did not reveal significant change in their expression in the bombesin-sap group (FIG. 13J-O). A comparison of the same panel of molecular markers in the spinal cords between the blank-sap and saline groups showed no significant changes in subpopulations of laminae I & II either in their numbers or their expression patterns (FIG. 14). In addition, the subsets of primary fibers examined by a variety of markers including GRP, CGRP, Substance P (SP) and IB4 remained unaffected by the bombesin-sap treatment (FIG. 15). Together, these data demonstrate that only GRPR+ cells were ablated, whereas neither other subpopulations of lamina I neurons and lamina II nor the primary afferents were affected. Moreover, the normal expression pattern of NK1 in mice treated with bombesin-sap indicates that GRPR⁺ neurons and NK1⁺ neurons whose neuroanatomic, electrophysiological and functional features have been most intensively studied are two distinct subpopulations in lamina I of the spinal cord.

Figure 16A:
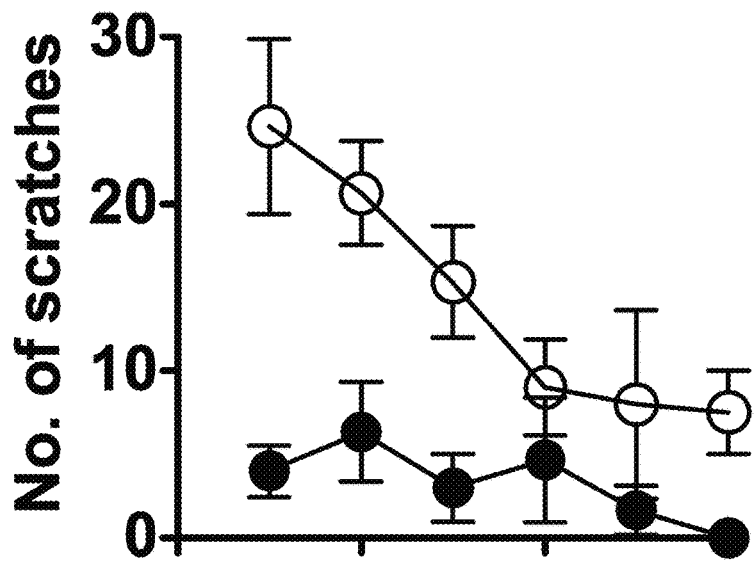
FIG. 16A-F depicts significant reduction of scratching behaviors in mice treated with bombesin-sap (filled circles) relative to the blank-sap control (open circles). (A) i.d. injection of histamine (500 μg/50 μl) (P<0.001). (B) i.d. injection of the compound 48/80 (100 μg/50 μl) (P<0.05). (C) i.d. injection of a PAR2 agonist (SLIGRL-NH2, 100 μg/50 μl) (P<0.001). (D) i.d. injection of chloroquine (200 μg/50 μl) (P<0.001). (E) i.d. injection of endothelin-1 (25 ng/50 μl) (P<0.001). (F) i.d. injection of 5-HT (10 μg/50 μl) (P<0.001). Two way repeated measured analysis of variance (ANOVA). n=6-9 for each group. Sap, saporin; i.d. intradermal. Error bars represent s.e.m.
Figure 16B:
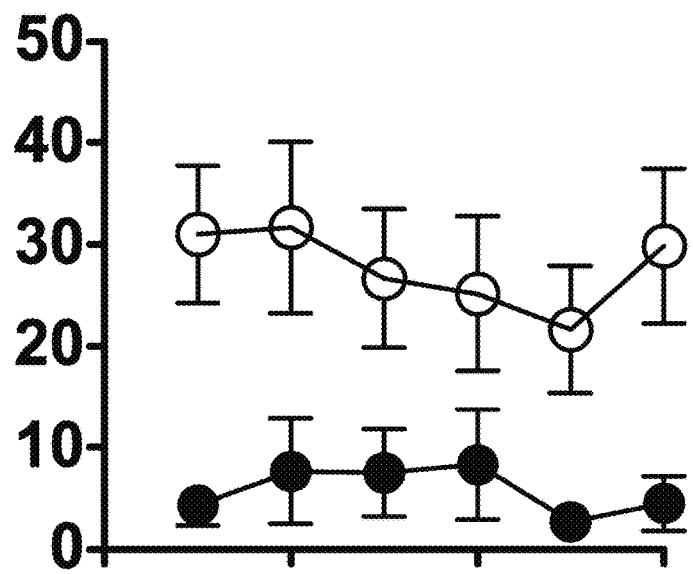
Figure 17A:
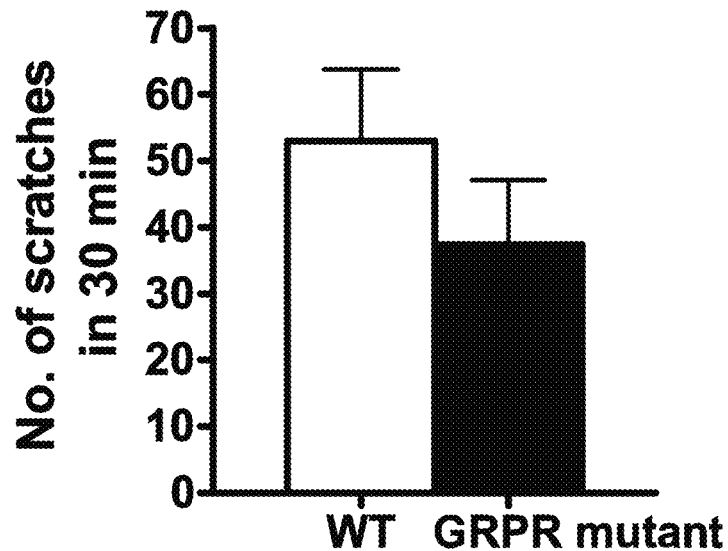
FIG. 17A-C depicts scratching behavior induced by i.d. injection of histamine, endothelin-1 or 5-HT in GRPR mutant (black bars) and wild-type mice (white bars). Scratching behavior elicited by i.d. injection of histamine (A), endothelin-1 (B) or 5-HT (C) in GRPR mutant mice are comparable to that in the wild-type littermates. n=6-7 for each group. i.d. intradermal. P>0.05, Student's t-test.

Example 14. GRPR+ Neurons Mediate Histamine or Histamine-Dependent Itch Sensation To assess the role of GRPR⁺ neurons in itch sensation, mice treated with bombesin-sap and blank-sap were subjected to i.d. injection of a panel of pruritogenic agents followed by counting scratching behaviors. Unlike the control mice which exhibited vigorous scratching, mice treated with bombesin-sap rarely showed scratching behaviors in response to injection of histamine, a potent pruritogen (FIG. 16A). Consistently, scratching behavior evoked by compound 48/80, a mast cell degranulator, was also largely lost (FIG. 16B). These results are in a striking contrast with that of GRPR mutant mice whose scratching behavior evoked by histamine or compound 48/80 was either not significantly affected or modestly reduced (FIG. 17A). Thus, GRPR⁺ neurons are a subpopulation of lamina I cells pivotal for mediating histamine or histamine-dependent itch sensation.

Example 15. GRPR+ Neurons Mediate Histamine-Independent Itch Sensation

Figure 16C:
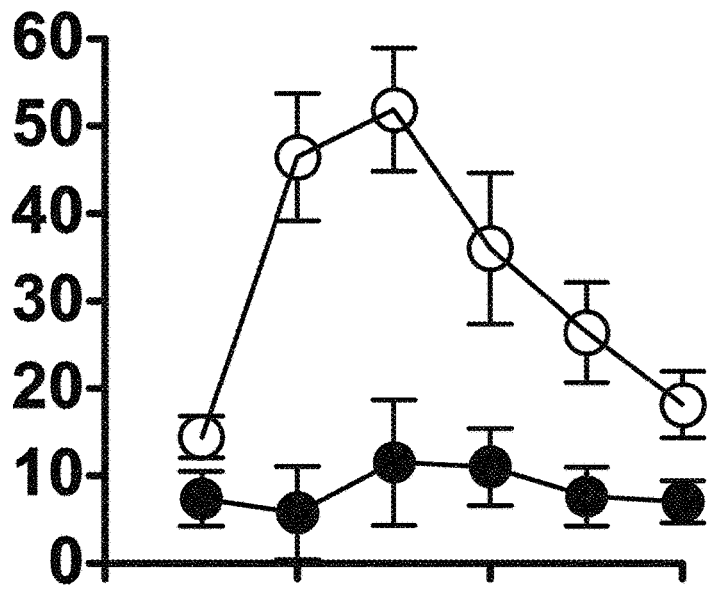
Figure 16D:
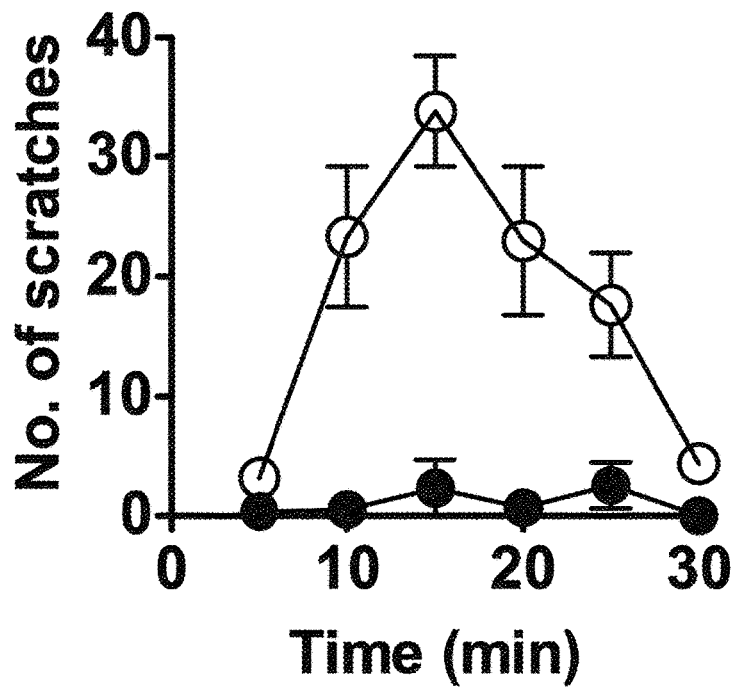
Figure 16E:
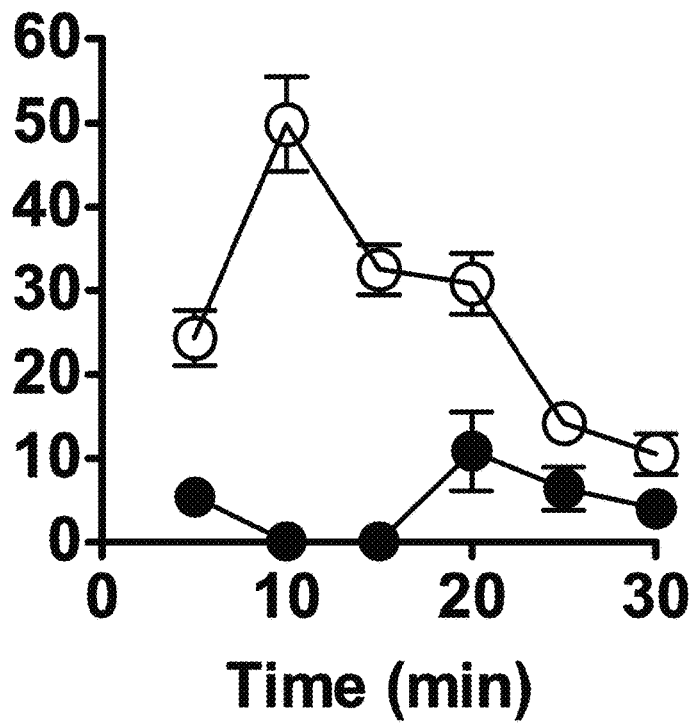
Figure 16F:
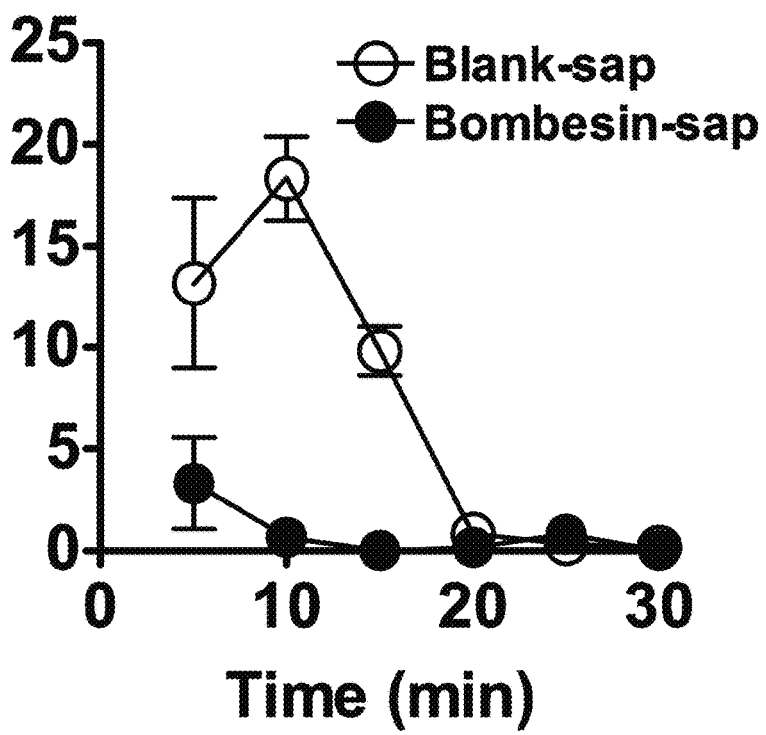
Figure 17B:
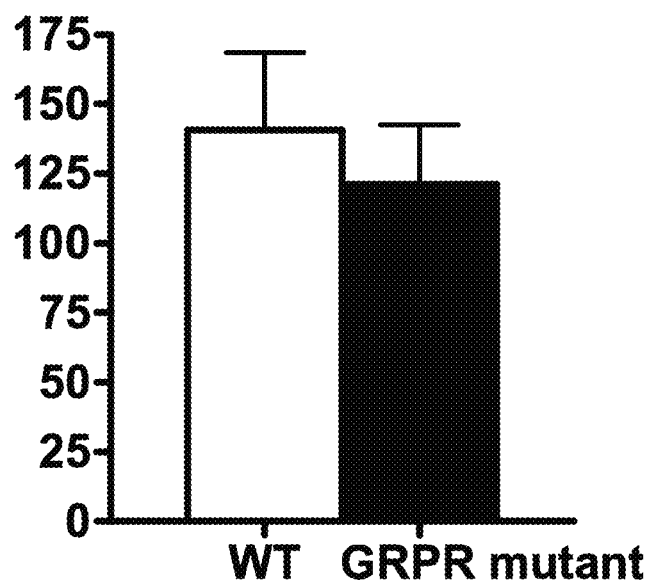
Figure 17C:
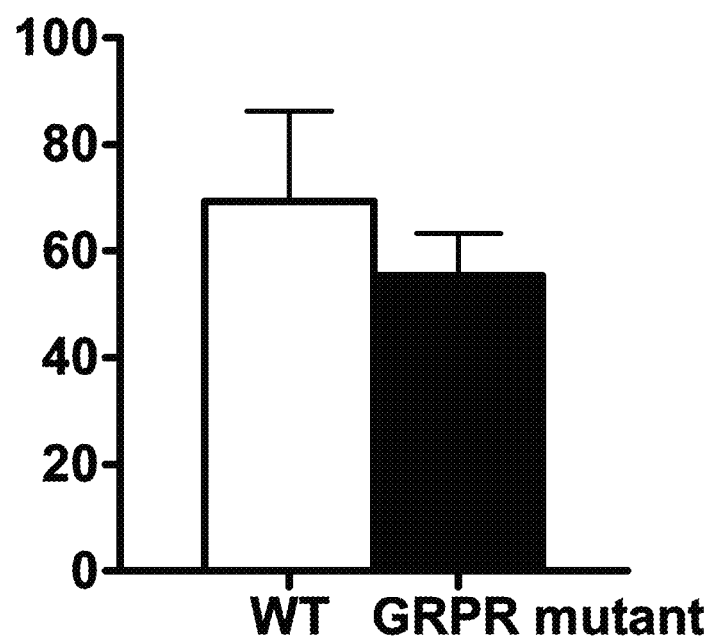
Figure 18A:
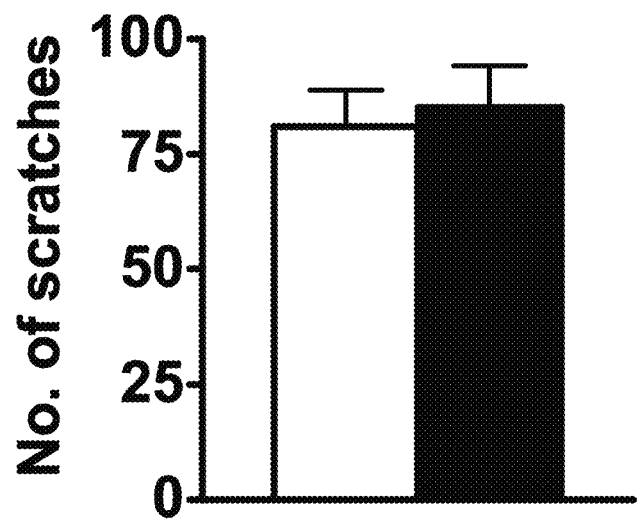
FIG. 18A-F shows that scratching behaviors are not affected by intrathecal blank-sap in wild-type mice. Scratching behaviors elicited by i.d. injection of histamine (A), compound 48/80 (B), a PAR2 agonist (SLIGRL-NH2, C), chloroquine (D), endothelin-1 (E) or 5-HT (F) in mice treated with intrathecal blank-sap are comparable to the saline group. n=6-7 for each group. Sap, sap, i.d. intradermal. Error bars represent s.e.m.
Figure 18B:
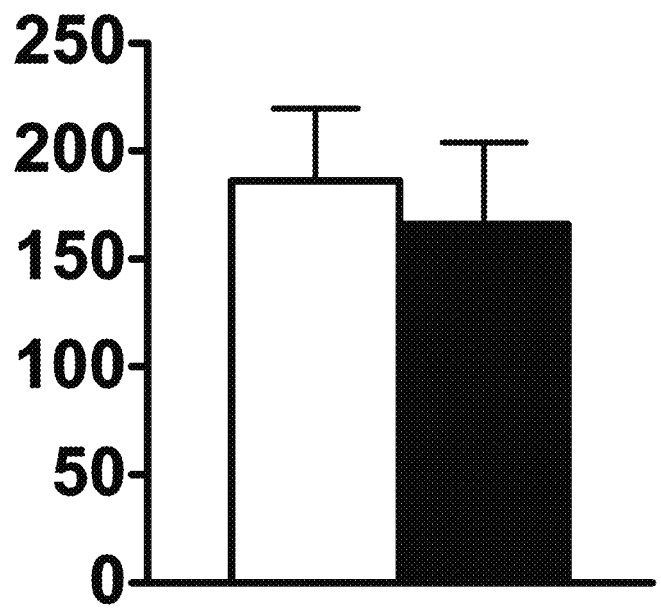
Figure 18C:
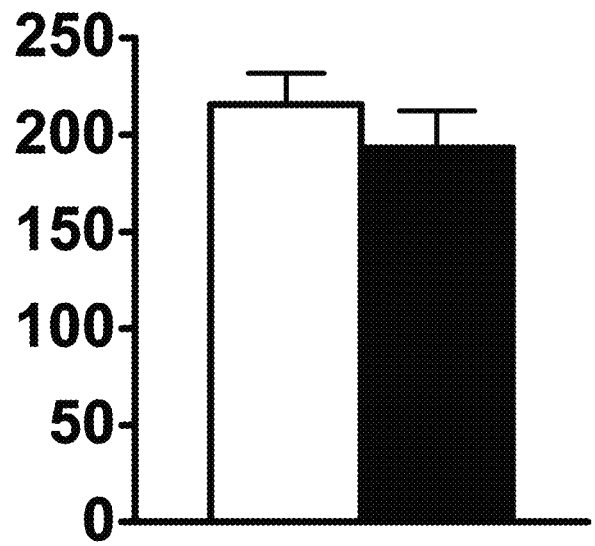
Figure 18D:
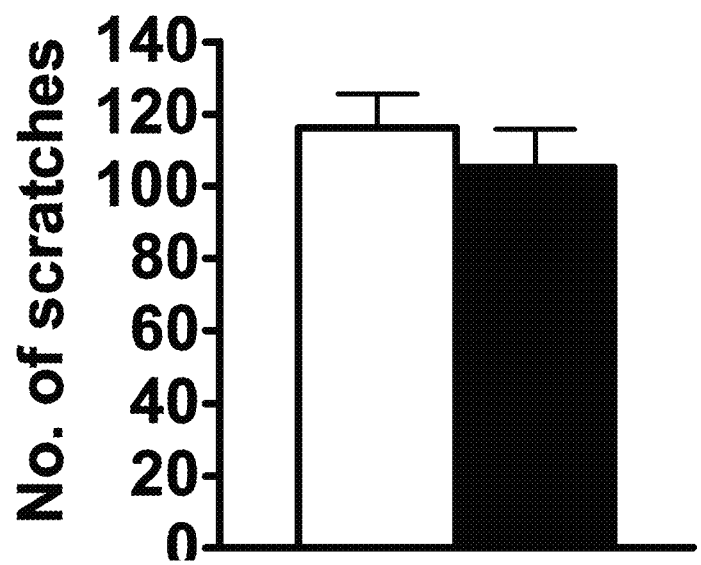
Figure 18E:
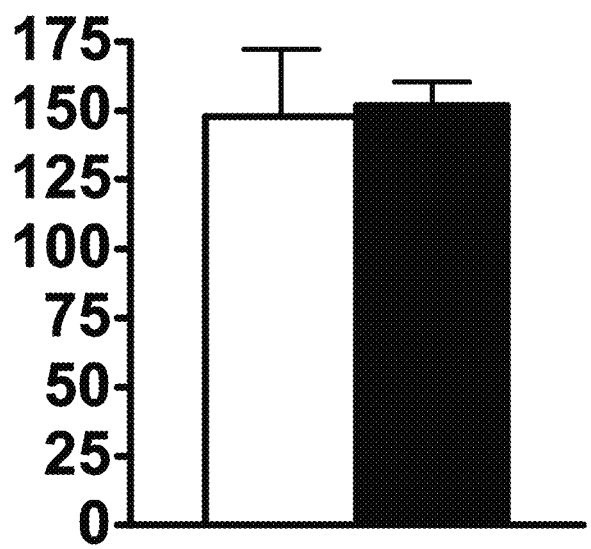
Figure 18F:
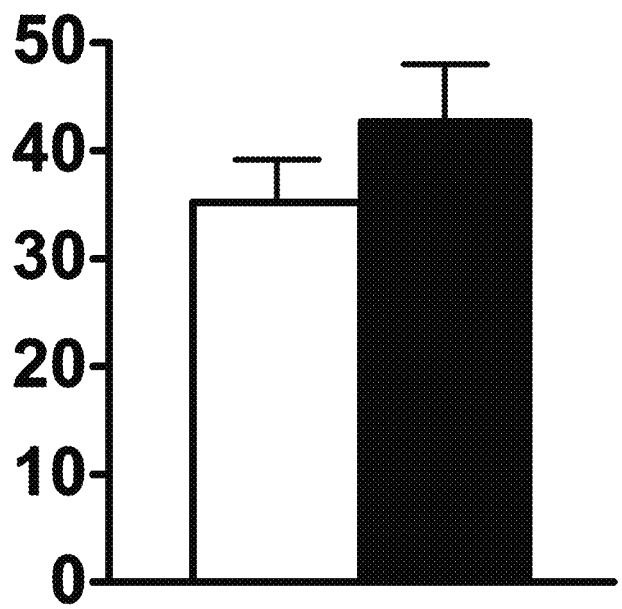
Figure 19A:
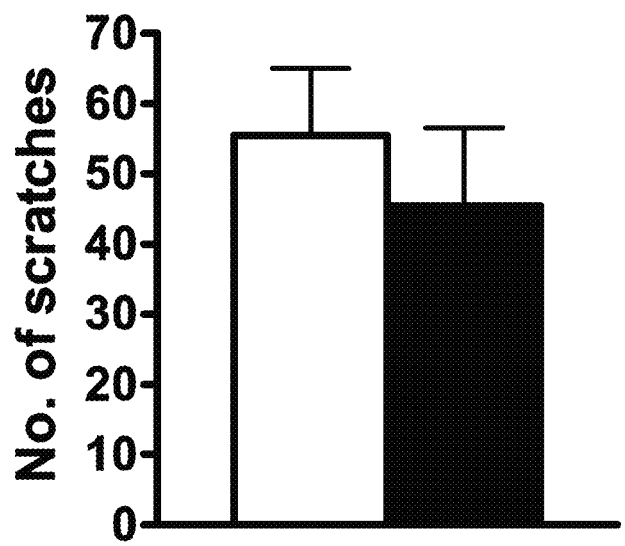
FIG. 19A-F shows that the effect of bombesin-sap on scratching behaviors was abolished in GRPR mutant mice. Scratching behaviors elicited by intradermal injection of histamine (A), compound 48/80 (B), a PAR2 agonist (SLIGRL-NH2, C), chloroquine (D), endothelin-1 (E), and 5-HT (F) are comparable between the bombesin-sap (black bars) and the blank-sap groups (white bars) in GRPR mutant mice. P>0.05, Student's t-test. n=6-13 for each group. Sap, saporin. Error bars represent s.e.m.
Figure 19B:
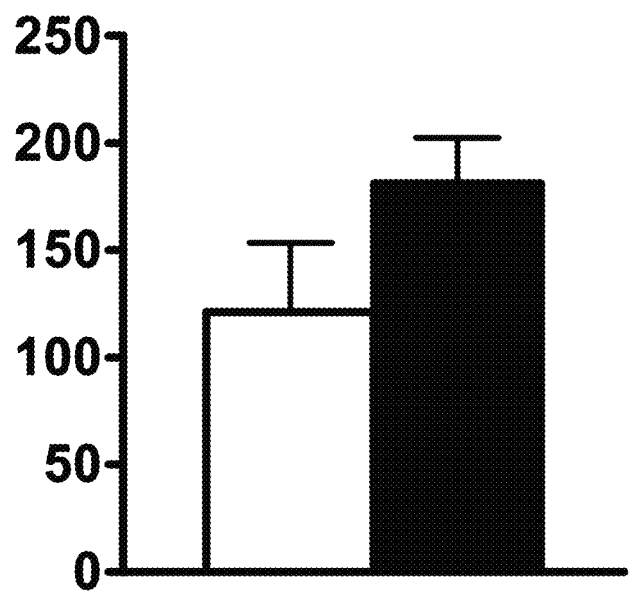
Figure 19C:
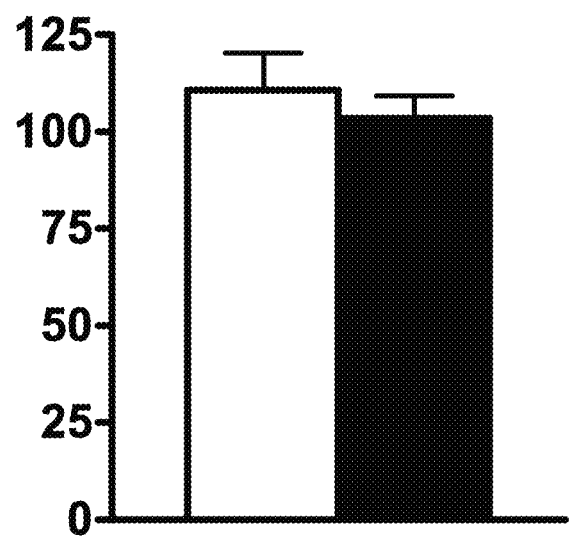
Figure 19D:
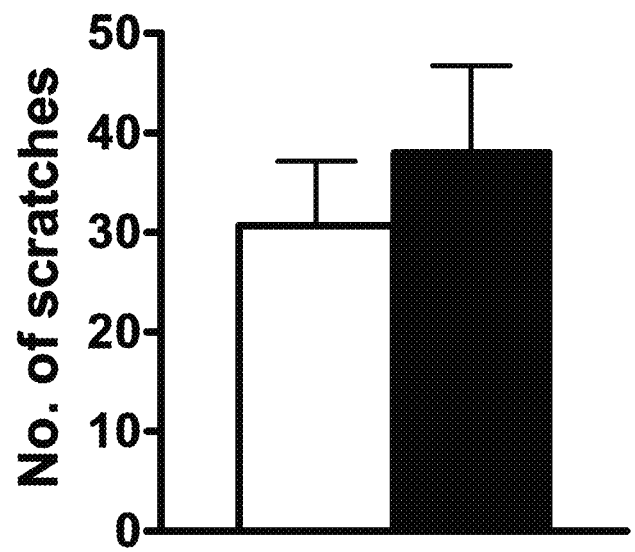
Figure 19E:
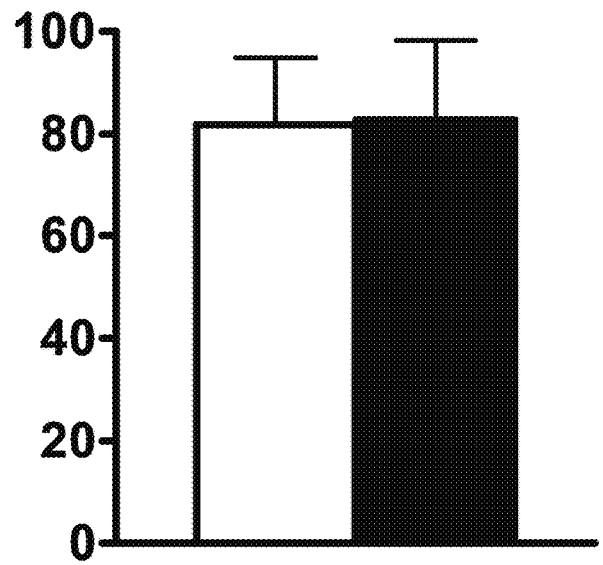
Figure 19F:
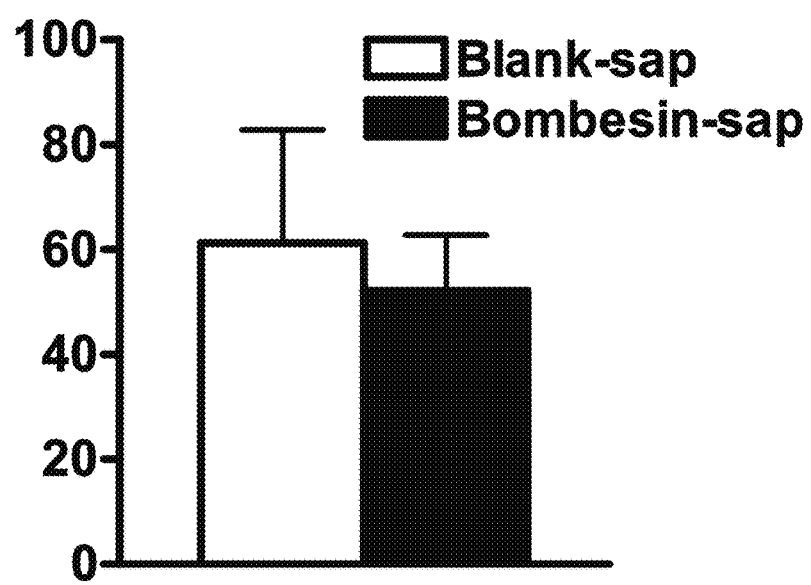

We next determined scratching behaviors elicited by an agonist for PAR2, a receptor which mediates histamine-independent itch via protease mucunain and chloroquine, an antimalarial drug which also causes pruritus in Africans. Similarly, mice treated with bombesin-sap rarely scratched in these tests, whereas the control mice responded vigorously (FIG. 16C, D). Our data thus identify GRPR⁺ neurons as a subpopulation of lamina I cells pivotal for mediating both histamine-dependent and histamine-independent itch sensation. Finally, we asked whether GRPR⁺ neurons may mediate the sensation of itching whose histamine-dependence is yet to be determined. Examination of scratching behaviors elicited by endothelin-1, which exerts its pruritic effect through $ET_A$ receptors, and serotonin or 5-HT also found that a nearly lack of responses to these stimuli in mice treated with bombesin-sap (FIG. 16E, F). In contrast, GRPR mutant mice exhibited normal scratching behaviors in response to endothelin-1 and 5-HT (FIG. 17B, C). In all pruritic agents tested the scratching behaviors of the blank-sap group and the saline group were similar, demonstrating that blank-sap had no neurotoxicity on the dorsal horn neurons (FIG. 18). Taken together, these results suggest that GRPR+ neurons are required for itch sensations mediated by varying mechanisms.

Example 16. GRPR+ Neurons are the Only Population of Cells Responsible for Loss of Scratching in Mice Treated with Bombesin-Sap Although molecular analysis has suggested that subpopulations of GRPR⁺-independent neurons in the dorsal spinal cord were normal after intrathecal bombesin-sap treatment, we did not know whether some subsets of GRPR-independent neurons not identified by available lamina I markers might have been killed by bombesin-saporin, thereby contributing to the phenotype. This issue is important because we cannot exclude the possibility that bombesin may also bind to some receptors that may be expressed in non-GRPR⁺ neurons. Because the GRPR mutation should protect GRPR⁺ neurons from being ablated by bombesin-sap, we reasoned that if GRPR cells were only population being killed in the dorsal spinal cord and responsible for the phenotype, GRPR mutant mice treated with bomesin-sap and with blank-sap respectively should exhibit comparable scratching responses. Indeed, we found that scratching behaviors of GRPR mutant mice were similar between the bombesin-sap and blank-sap groups in all itch models tested (FIG. 19), demonstrating that a lack of neurotoxicity effect of bombesin-sap in the spinal cord of GRPR mutant mice. Therefore, we conclude that GRPR⁺ neurons are the only population of cells responsible for the loss of scratching behaviors in wild-type mice treated with bombesin-sap.

Example 17. Pain Behavior of Mice Treated with Bombesin-SAP

Figure 20A:
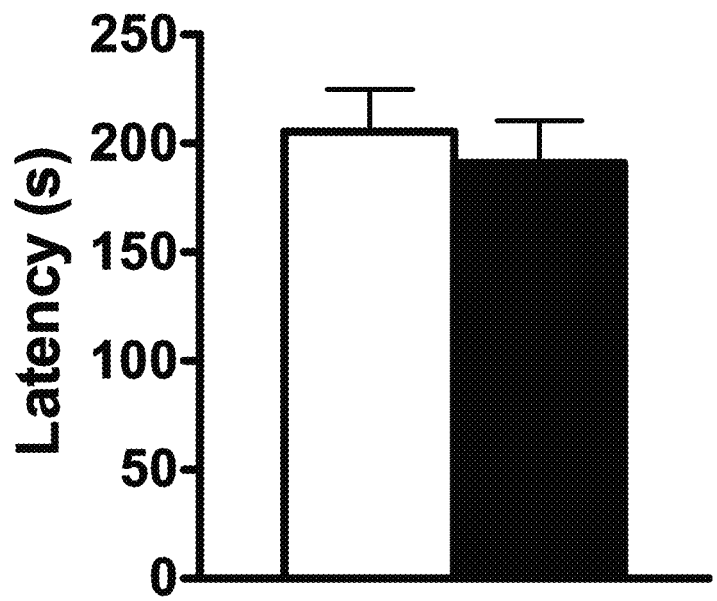
FIG. 20A-E depicts the effects of a loss of GRPR+ neurons on pain behaviors in mice treated with bombesin-sap (black bars) compared to the blank-sap (white bars) group. (A) Motor function assessed by the rotarod test is comparable between groups. P>0.05. (B) Mechanical sensitivity in mice treated with bombesin-sap as measured by paw withdrawal threshold upon exposure to von Frey filaments is comparable to mice treated with blank-sap. P>0.05. (C and D) Responses to noxious thermal stimulation measured by the paw withdrawal latency (Hargreaves test, C), and the water immersion tail-flick latency (D) were indistinguishable between groups. P>0.05. (E) Spontaneous pain response in mustard oil test was significantly reduced in bombesin-sap treated group relative to the control group. *P<0.05. Student's t-test. n=8 for each group. Sap, saporin. Error bars represent s.e.m.
Figure 20B:
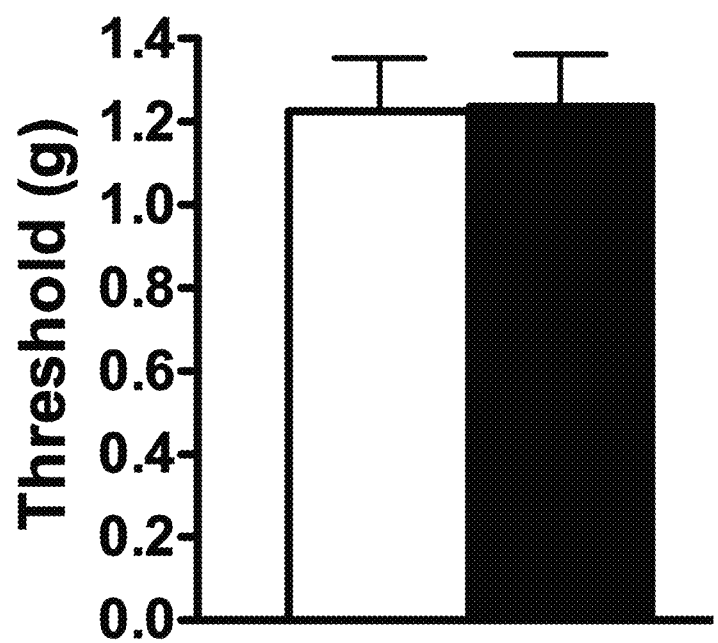
Figure 20C:
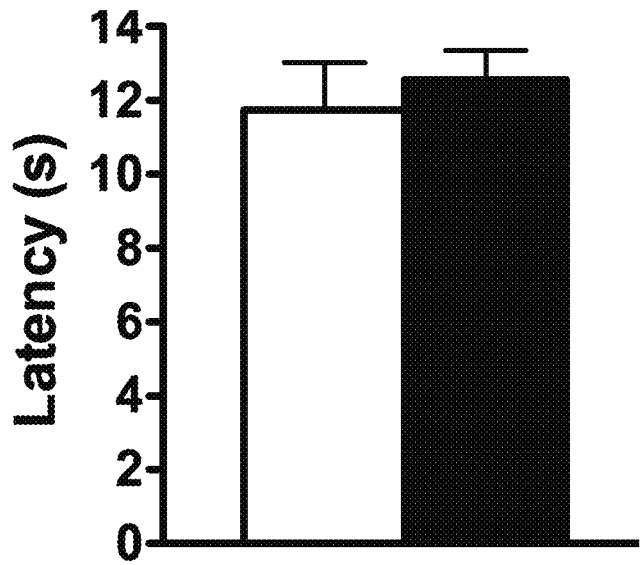
Figure 20D:
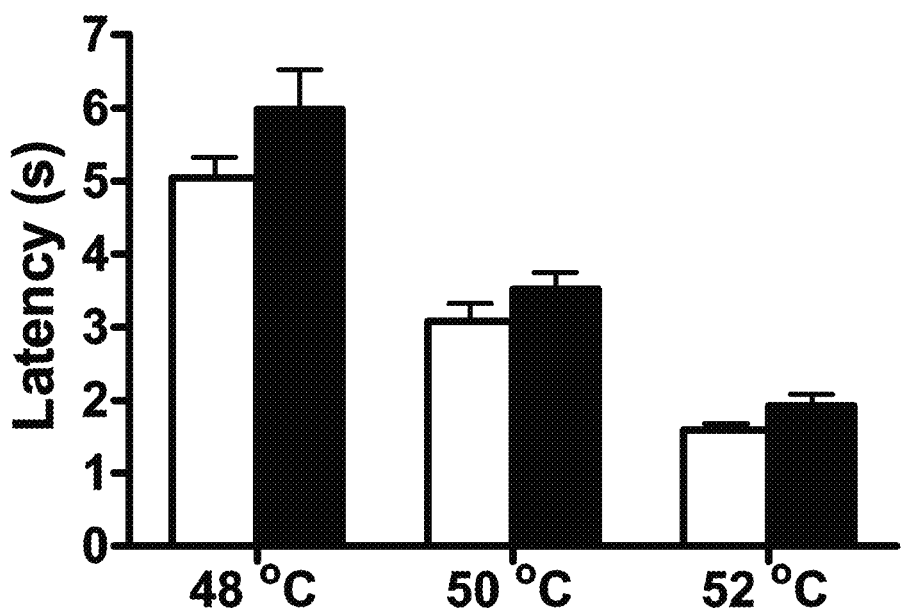
Figure 20E:
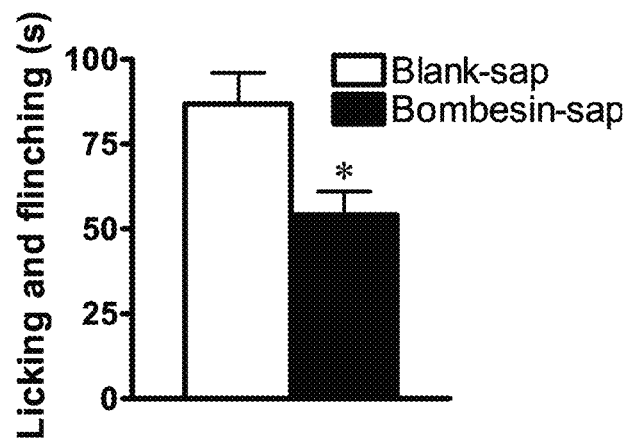
Figure 21A:
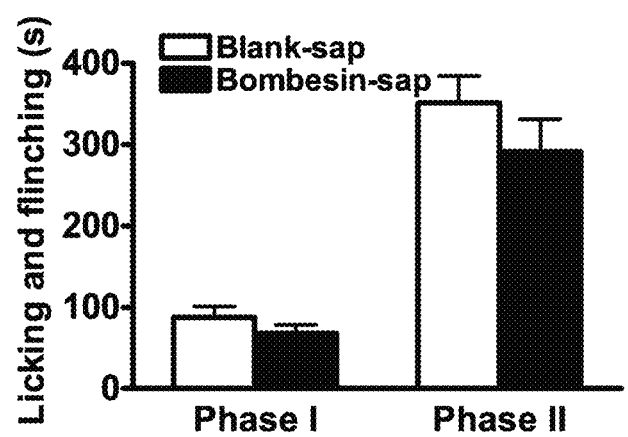
FIG. 21A-C depicts the effects of a loss of GRPR+ neurons on persistent inflammatory and neuropathic pain behaviors. (A) Spontaneous pain responses in first (0-10 min) and second phase (10-60 min) of the formalin test are comparable between mice treated with blank-sap (white bars) and bombesin-sap (black bars). P>0.05, Student's t-test. (B) Mechanical hyperalgesia induced by intraplantar injection of CFA (20 μl) is comparable between mice treated with blank-sap (open circles) and bombesin-sap (filled circles). Two way repeated measured analysis of variance (ANOVA) comparing between groups, P>0.05. (C) Mechanical sensitivity was tested before and after partial sciatic nerve injury. Mechanical allodynia of the ipsilateral hindpaw is comparable between mice treated with blank-sap (open circles) and bombesin-sap (filled circles). Two way ANOVA comparing between groups, P>0.05. n=5-7. CFA, complete Freund's adjuvant; sap, saporin; PNI, partial sciatic nerve injury. Error bars represent s.e.m.
Figure 21B:
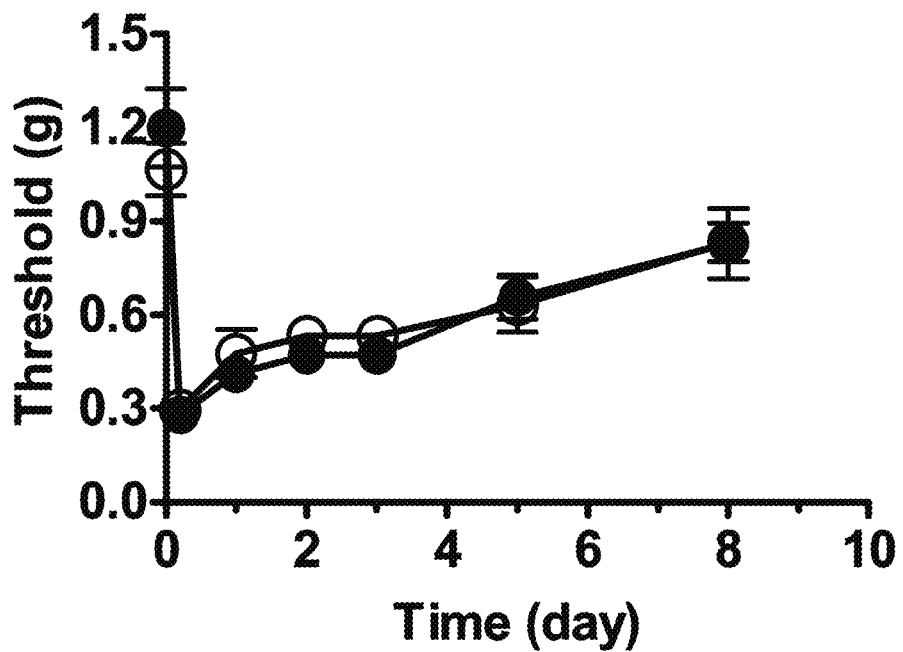
Figure 21C:
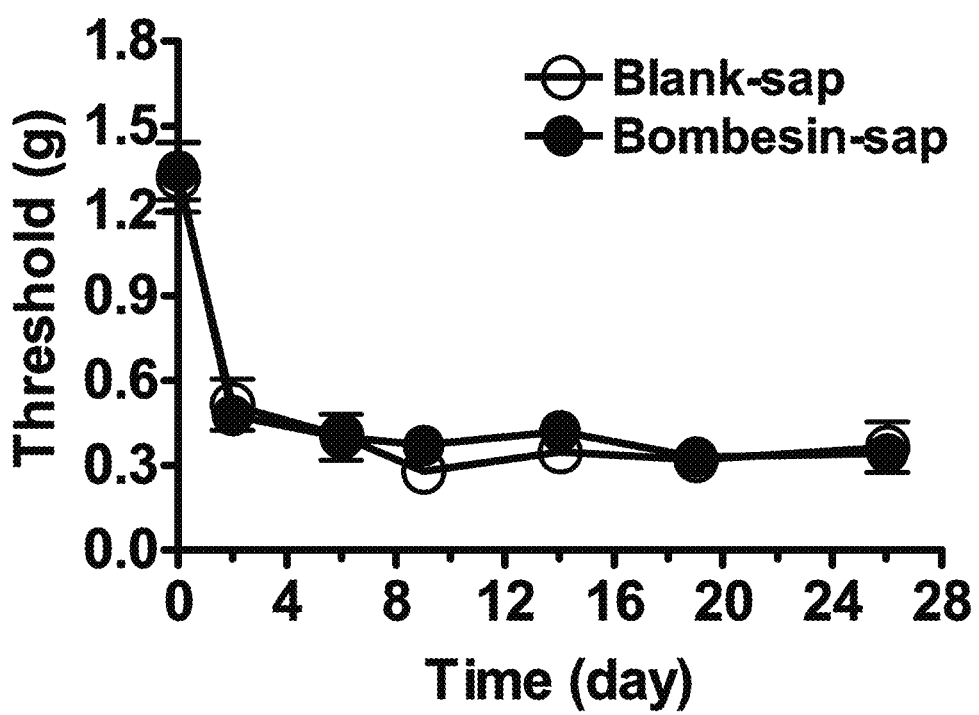
Figure 22A:
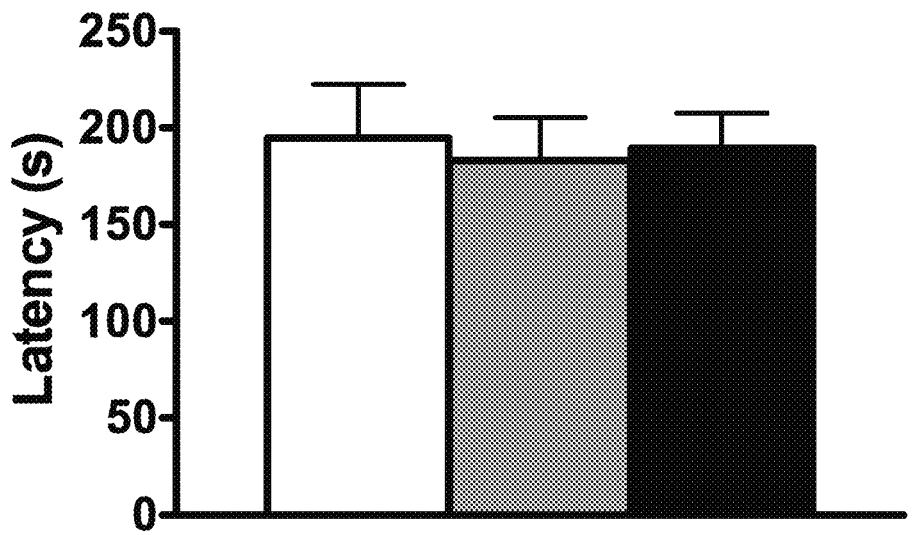
FIG. 22A-F shows that pain behaviors in GRPR mutant mice are not affected by blank-sap (gray bars) or bombesin-sap (black bars) as compared to the saline group (white bars). (A) Comparable motor function assessed by the rotarod test among groups. P>0.05. (B) Comparable mechanical sensitivity of mice among groups. P>0.05. (C and D) Responses to noxious thermal stimulation measured by the paw withdrawal latency (Hargreaves test, C), and the water immersion tail-flick latency (D). There were no significant differences in thermal pain responses among groups. P>0.05. (E) Spontaneous pain responses in mustard oil test were not affected by blank-sap or bombesin-sap treatment. (F) Spontaneous pain responses in first (0-10 min) and second phase (10-60 min) of formalin test were not affected by treatment of either blank-sap or bombesin-sap as compared with the saline group. P>0.05. n=6-8 for each group. Student's t-test. Error bars represent s.e.m.
Figure 22B:
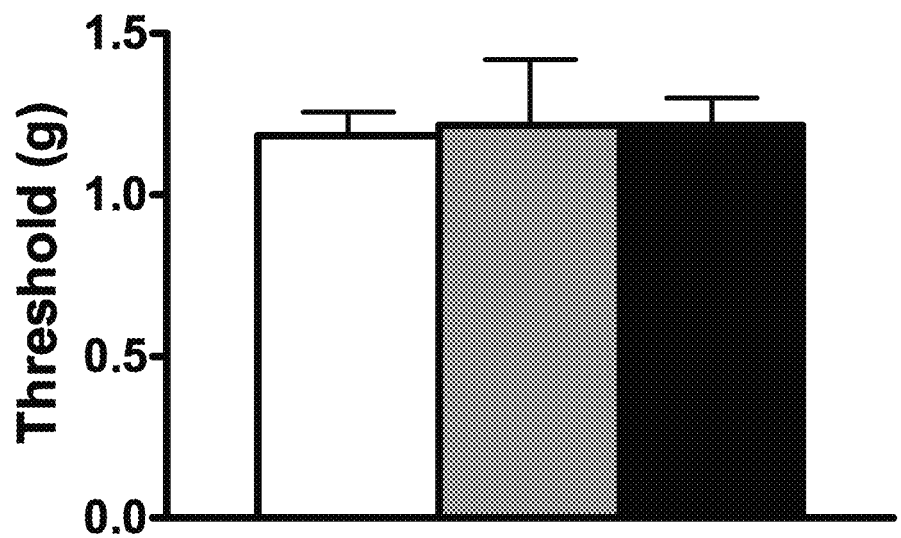
Figure 22C:
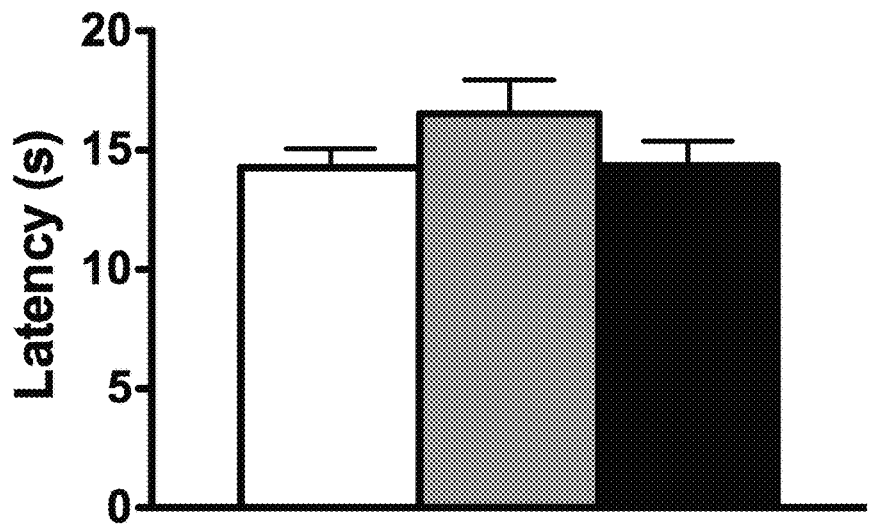
Figure 22D:
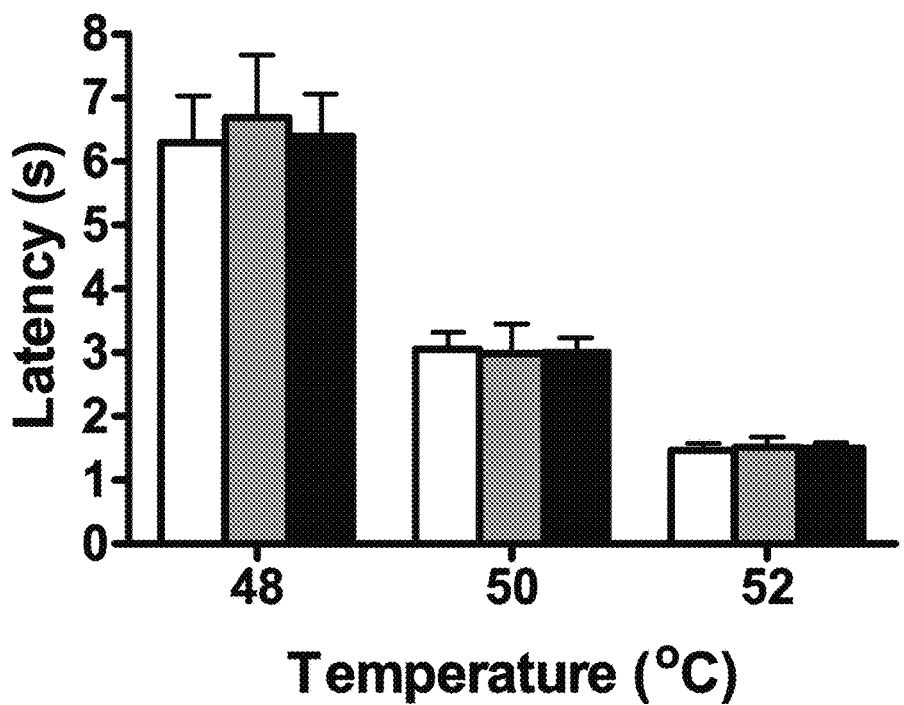
Figure 22E:
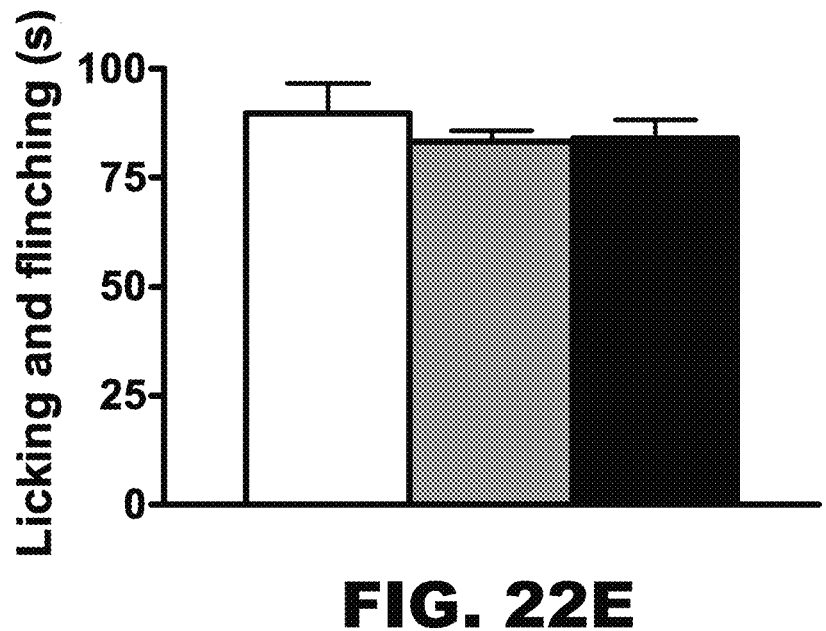
Figure 22F:
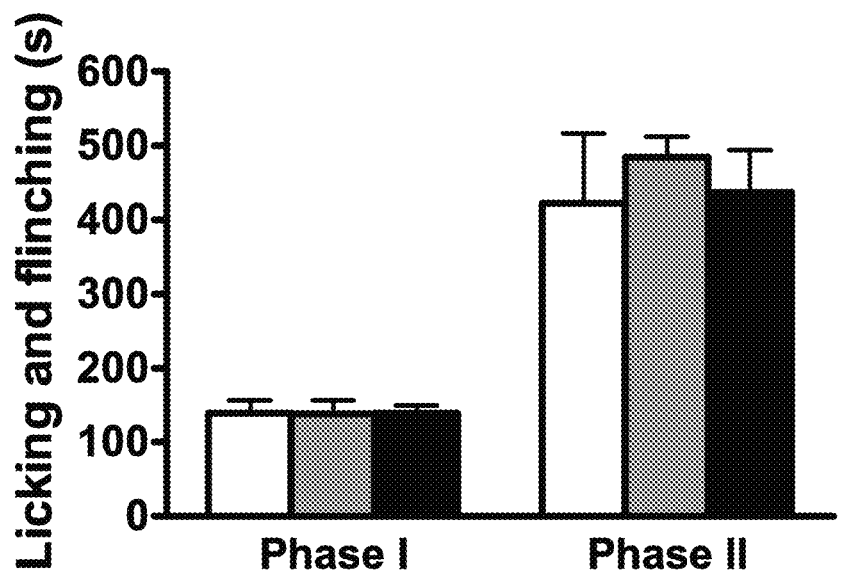

To exclude the possibility that a loss of scratching behaviors of mice treated with bombesin-sap may be attributed by the impaired motor function, the motor activity of treated mice was assessed by the rotarod test. No significant difference in time mice spent on the accelerating rotating rod was found between the bombesin-sap and the control groups, indicating that the ablation of GRPR⁺ neurons did not influence the motor function (FIG. 20A). Thus, these mice should provide a unique venue to address whether itch and pain signals are relayed by the same neural pathway. Next we tested mice treated with bombesin-sap using a variety of acute and persistent pain behavioral paradigms. Mechanical withdrawal threshold was examined by von Frey filaments and no significant difference between two groups was found, indicating that GRPR⁺ neurons are dispensable for mechanical pain (FIG. 20B). The acute thermal pain was assessed by the paw withdrawal (Hargreaves) and tail-flick tests, and in both paradigms the latency of the responses to thermal stimuli in the bombesin-sap group was also similar to the control mice (FIG. 20C, D). Mustard oil, which elicits a sensation of burning pain via TRPA1, was used for testing acute inflammatory pain. However, the licking and flinching behaviors evoked by the injection of mustard oil (0.75%) into the plantar surface of one hindpaw were reduced significantly in mice treated with bombesin-saporin (FIG. 20E), suggesting that GRPR⁺ neurons are involved in mustard oil-evoked pain. We also tested acute and persistent inflammatory pain responses using the formalin which elicited a biphasic response lasting about 10 min (the first phase) and from 10 min to one hr (the second phase) respectively. We found that licking and flinching behaviors elicited by intraplantar injection of 5% formalin in both phases were indistinguishable between the treated group and the control group (FIG. 21A). To evaluate whether GRPR⁺ neurons are required in persistent inflammatory pain, we used Complete Freund's adjuvant (CFA) model. CFA was injected into the plantar of the right hindpaw of mice followed by measuring their mechanical sensitivity using a set of calibrated von Frey filaments. Mechanical hypersensitivity in mice treated with bombesin-sap was comparable to that in the control group (FIG. 21B). These data suggest that GRPR⁺ neurons are not important for the development of persistent inflammatory pain. Finally, we asked whether there was an alteration of neuropathic pain in treated mice using partial sciatic nerve injury (PNI) model. The mechanical hyperalgesia (increased sensitivity to noxious stimuli) after bombesin-sap treatment remained comparable to that in the control group (FIG. 21C). With the exception of mustard oil test, mice lacking GRPR⁺ neurons in the spinal cord showed normal pain behaviors which are reminiscent of that of GRPR mutant mice. To determine whether bombesin-sap might have killed some of GRPR-independent neurons which may not be important for itch but have accounted for the compromised pain behaviors elicited by mustard oil, we compared pain responses of GRPR mutant mice treated with bombesin-sap and blank-sap. Similar to other pain tests, we did not find any difference between the groups with respect to their responses to mustard oil (FIG. 22). These results again reinforce the notion that the impaired mustard oil-elicited pain can be ascribed to the loss of GRPR$^+$ neurons only. Together, except for mustard oil, our data suggest that GRPR$^+$ neurons are not important for acute pain, persistent inflammatory and neuropathic pain.

Materials and Methods for Examples 13-17

Animals:

Both male GRPR mutant mice and C57BL/6J mice (The Jackson Laboratory) of age between 8 and 12 weeks age were acclimatized to the experimental room and used for experiments. All behavioral tests were done by observers blinded to the treatment or genotype of the animals. All the experiments were performed in accordance with the guidelines of the National Institutes of Health and the International Association for the Study of Pain and were approved by the Animal Studies Committee at Washington University School of Medicine.

Toxin Treatment:

Mice were intrathecally injected with blank-sap (400 ng/5 µl, Advanced Targeting Systems, CA), bombesin-sap (400 ng/5 µl, Advanced Targeting Systems, CA), saline (5 µl), and the intrathecal injection was performed as described previously.

Itch Behavior:

The itch behavioral tests were performed as previously described. Briefly, prior to experiments, mice were given 30 min to acclimate to a small plastic chamber (15×26×12 cm). Mice were briefly removed from the chamber and intradermally injected with drugs at a volume of 50 µl. Hindlimb scratching behavior directed towards the injection site at the back of the neck was observed for 30 min at 5-min intervals. One scratch is defined as a lifting of the hind limb towards the injection site and then a replacing of the limb back to the floor, regardless of how many scratching strokes take place between those two movements. For intradermal injection, the following drugs was dissolved in sterile saline and administered at a volume of 50 µl: endothelin-1 (25 ng/50 µl), 5-HT (10 µg/50 µl, Sigma), compound 48/80 (100 µg/50 µl, Sigma), SLIGRL-NH2 (100 µg/50 µl, Bachem), chloroquine (200 µg/50 µl, Sigma), histamine (500 µg/50 µl, Sigma).

Assessment of Motor Function:

A rotarod system of accelerating treadmills (Ugo Basile, Italy) was used to assess coordinate motor activity and general motor disability as described. The mice were tested for 3 trials with 15-min intervals, and the latencies of animals to fall were averaged.

Pain Behavior Tests:

Pain behaviors were assessed as described previously. Mechanical sensitivity was assessed using a set of calibrated von Frey filaments (Touch-Test kit, Stoelting). Each filament was applied 5 consecutive times and the smallest filament that evoked reflexive flinches of the paw on 3 of the 5 trials was taken as paw withdrawal threshold. Thermal sensitivity was determined by Hargreave's test and water immersion tail-flick methods. For the water immersion tail-flick test, tails were dipped beneath the water in a temperature-controlled water bath (IITC Inc.). The latency to withdrawal was measured.

Mustard Oil Test:

Mustard oil (0.75%, Sigma, St. Louis, Mo.) in 20 µl vehicle (mineral oil) was injected into the plantar surface of one hindpaw, and the duration of licking and flinching of the injected paw was recorded for the first 5 min.

Formalin Test:

Inflammatory pain was determined using a formalin test by intraplantar injection of formalin (Sigma, 10 µl of 5% formalin in saline) into the plantar surface of the right hindpaw. The total time spent in licking and flinching of the injected paw was monitored for 60 min.

Complete Freund's Adjuvant (CFA) Model:

In CFA induced inflammatory pain, the mice received an injection of CFA (20 µl, Sigma) into the plantar of the right hindpaw. Mechanical sensitivity was assessed using a set of calibrated von Frey filaments (Touch-Test kit, Stoelting).

Neuropathic Pain:

Surgery was performed as described before. In deeply anaesthetized mice (sodium pentobarbital, 50 mg/kg), incision was made in the left hindlimb at mid-thigh level. A partial nerve injury was produced by tying a tight ligature with 9-0 silk suture around approximately ⅓ to ½ the diameter of the sciatic nerve. And the incision was closed with surgical micro clips. Mechanical sensitivity was assessed before and after surgery.

Immunocytochemical Staining and In Situ Hybridization:

Immunocytochemical staining and in situ hybridization were performed as previously described. The following primary antibodies were used: rabbit anti-GRP (Immunostar), rabbit anti-CGRP (Peninsula), rabbit anti-SP (Immunostar), rabbit anti-PKCγ (Santa Cruz), rabbit anti-NK1 (chemicon). The nonpeptidergic primary afferents were identified with the IB4-FITC (Sigma). Donkey anti-rabbit IgG coupled to Cy3 (Jackson Immuno Research, West Grove, Pa.) was used as the secondary antibody.

Four sections in the cervical region were counted or measured for the signal density and averaged for each mouse. Density of NK1 positive signal in the superficial spinal cord was measured by NIH ImageJ software.

Data Analysis:

Statistical comparisons were performed with two-way analysis of variance (ANOVA) or Student's t-test. All data were expressed as the mean±standard error of the mean (s.e.m.) and error bars represent s.e.m. In all cases, $P<0.05$ was considered statistically significant.

Example 18. Morphine-Induced Pruritus is Dependent on GRPR-Mediated Signaling

Figure 23:
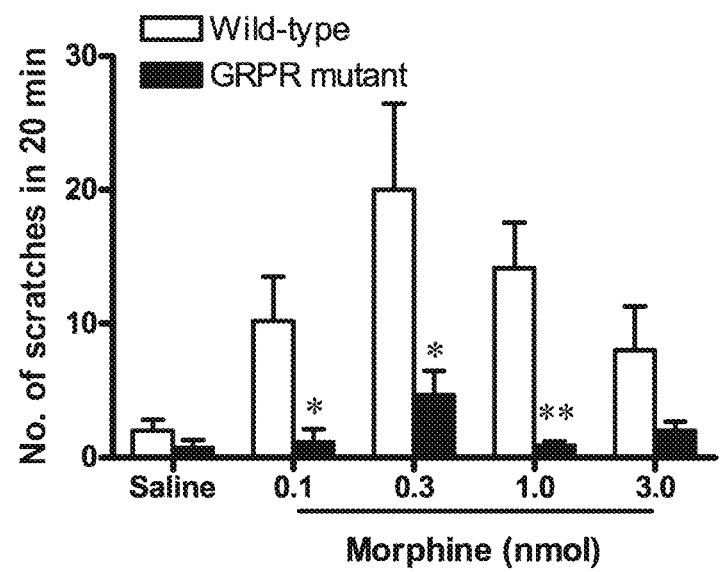
FIG. 23 depicts a graph showing that morphine-induced scratching behavior is significantly reduced in GRPR mutant mice. Different doses of morphine or saline vehicle were injected intrathecally, and scratching behavior was monitored for 20 min after injection. Intrathecal injection of morphine in wild-type mice (white bars) induced significantly elevated scratching behavior compared with the saline group. The scratching behavior was significantly reduced in GRPR mutant mice (black bars) compared with wild-type mice (white bars) at several different dosages (0.1, 0.3, and 1.0 nmol/5 μl). n=7-10. *P<0.05, **P<0.01, student's t-test. All data are presented as means±s.e.m.
Figure 24A:
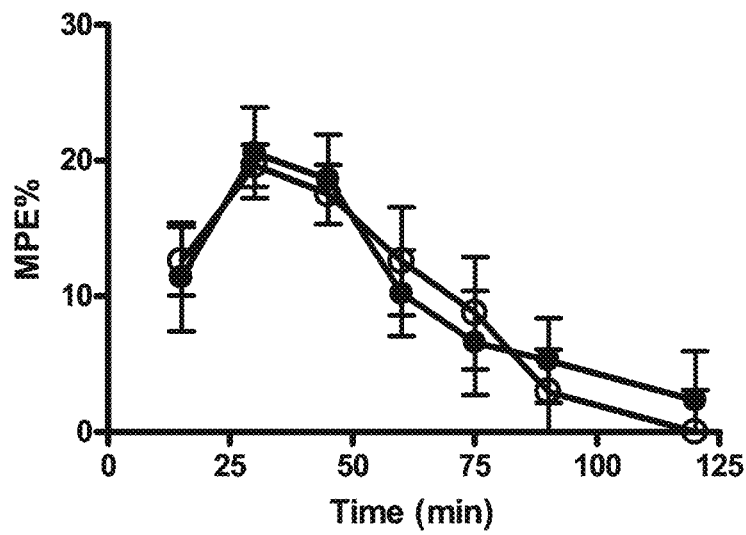
FIG. 24A-B depicts two graphs showing that the antinociceptive effect of morphine remains normal in GRPR mutant mice. The analgesic effect of intrathecal morphine was evaluated by water immersion tail-flick. The latency was tested after intrathecal injection of 0.1 nmol/5 μl (A) or 0.3 nmol/5 μl (B) of morphine in both wild-type and GRPR mutant mice. There were no significant differences in morphine analgesia between wild-type (open circles) and GRPR mutant mice (filled circles) at either dose. n=7-9. Repeated measures analysis of variance (ANOVA); P>0.05. All data are presented as means±s.e.m.
Figure 24B:
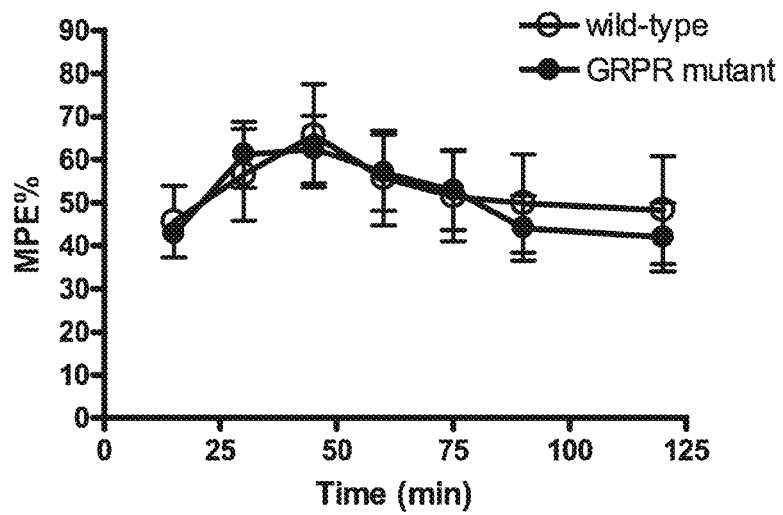

Itch/pruritus is one of the major side effects of opioid management. To examine whether morphine-induced pruritus is dependent on the GRPR-mediated signaling pathway, morphine-induced scratching behaviors were compared between GRPR mutant and wild-type littermate mice. In wild-type mice, intrathecal injection of morphine induced robust scratching behaviors, while a saline vehicle injection did not (FIG. 23). In contrast, morphine-induced scratching behavior was significantly reduced in GRPR mutant mice (FIG. 23). These results suggest that morphine-induced pruritus is dependent on the GRPR signaling pathway, and GRPR is an important mediator for morphine-induced scratching behaviors in the spinal cord. Importantly, the antinociceptive effect of intrathecal morphine tested by the tail-flick assay is comparable between wild-type and GRPR mutant mice (FIG. 24).

Figure 25A:
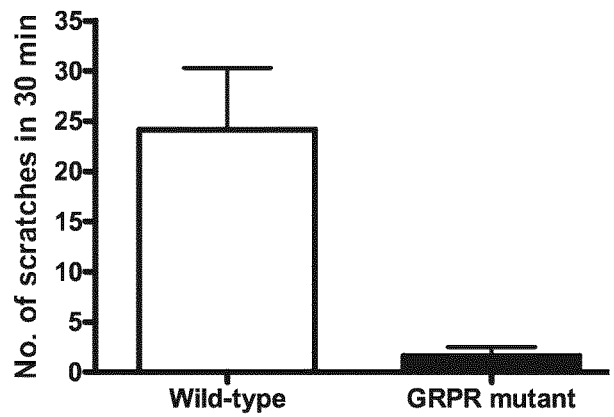
FIG. 25A-B depicts two graphs showing the effect of DAMGO, a highly selective mu opioid agonist, in wild-type and GRPR mutant mice. (A) DAMGO (0.02 nmol/5 μl) was injected intrathecally, and scratching behavior was monitored for 30 min after injection. The scratching behavior was significantly reduced in GRPR mutant mice (black bars) compared with wild-type mice (white bars). **P<0.01, student's t-test. (B) The antinociceptive effect of DAMGO (0.02 nmol/5 μl, i.t.) was tested by using tail-flick test. The antinociceptive effect of DAMGO is comparable between groups. Repeated measures analysis of variance (ANOVA); P>0.05. n=7-10. All data are presented as means±s.e.m.
Figure 25B:
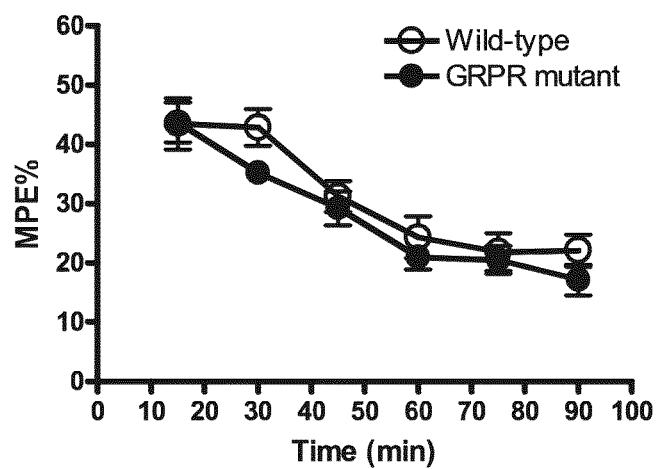

Previous studies have shown that morphine-induced scratching behavior is mainly mediated by the mu-opioid receptor (MOR). DAMGO, a MOR specific agonist, also induced scratching behavior after intrathecal injection, and this effect is almost abolished in GRPR mutant mice (FIG. 25A). In addition, the antinociceptive effect of DAMGO is comparable between wild-type and GRPR mutant mice (FIG. 25B). The expression of MOR is not affected by mutation of GRPR gene (FIG. 26), indicating that the defect morphine-induced scratching behavior is not caused by the change of MOR expression in GRPR mutant mice.

Example 19. GRPR Antagonist can Block Morphine-Induced Scratching

Figure 28:
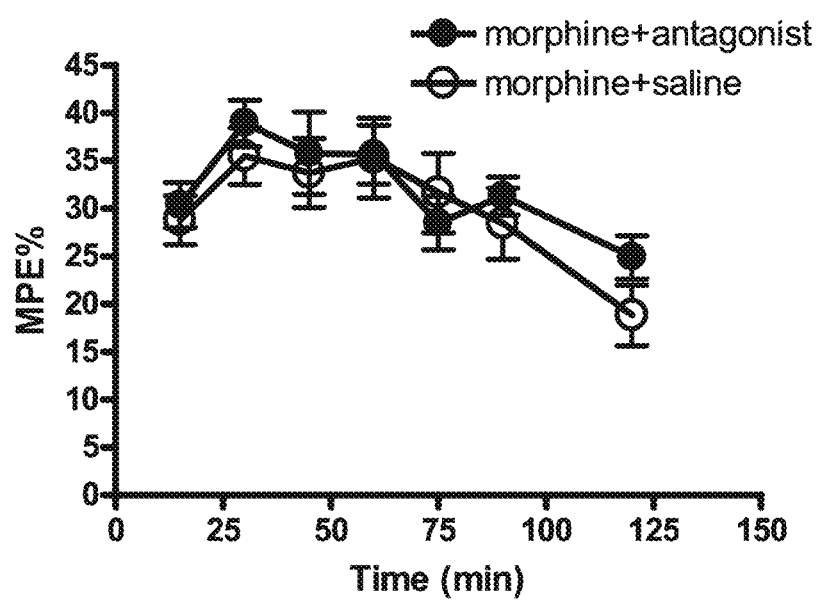
FIG. 28 depicts a graph showing that morphine analgesia is not significantly affected by co-injection of GRPR antagonist. The analgesic effect of intrathecal morphine (0.3 nmol/5 μl) was not significantly affected by GRPR antagonist [D-Phe-6-Bn(6-13)OMe, 1.0 nmol, filled circles] compared with vehicle (open circles). Repeated measures analysis of variance (ANOVA); P>0.05. n=6-8. All data are presented as means±s.e.m.
Figure 29A:
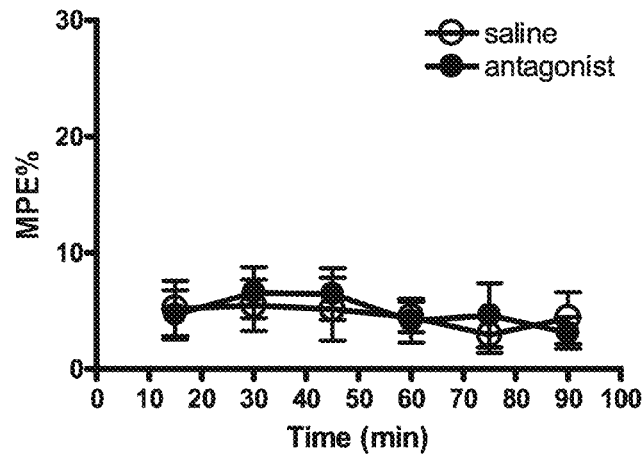
FIG. 29A-B depicts two graphs showing that the thermal and mechanical pain threshold is not affected by intrathecal injection of GRPR antagonist [D-Phe-6-Bn(6-13)Ome, 1.0 nmol] (A) Tailflick latency is comparable in the mice injected intrathecally with GRPR antagonist (filled circles) compared with vehicle control (open circles). (B) Mechanical thresholds are not significantly affected by GRPR antagonist (filled circles) compared with vehicle (open circles). Repeated measures analysis of variance (ANOVA); P>0.05. n=6. All data are presented as means±s.e.m.
Figure 29B:
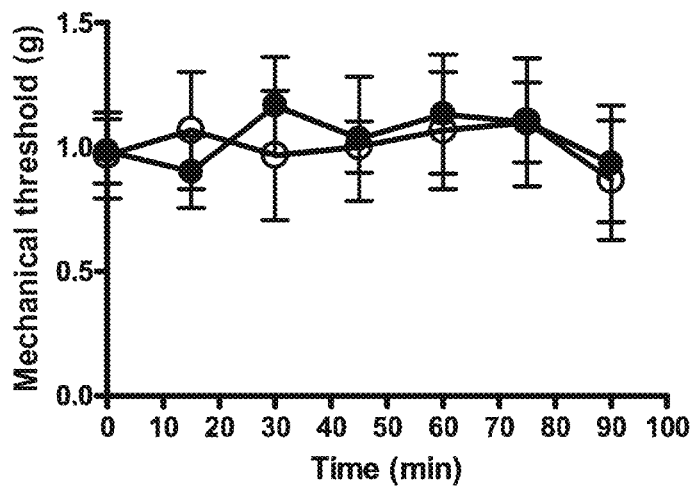

To test whether a GRPR antagonist can block morphine-induced scratching behavior, a GRPR antagonist (0.1, 1 nmol) was injected together with morphine. The GRPR antagonist can significantly block morphine-induced scratching behavior (FIG. 27). The antinociceptive effect of morphine is not affected by co-injection of GRPR antagonist (FIG. 28). So blocking of GRPR would specifically inhibit the itch induced by morphine, without compromising morphine's antinociceptive effect. Moreover, acute thermal pain and mechanical pain are not affected by intrathecal injection of GRPR antagonist compared to a control group (FIG. 29).

Example 20. Role of Primary Afferent Fibers

Presynaptic calcium channels have been implicated in the release of neuropeptides from primary afferent fibers. To further test the hypothesis that morphine-induce pruritus is mediated by the release of GRP from primary fibers, the effect of a calcium channel blocker on morphine-induce pruritus was examined. The N-type calcium channel blocker ω-Conotoxin GVIA, when coinjected with morphine, significantly inhibited the scratching behavior induced by morphine (FIG. 30). ω-Conotoxin GVIA has been reported to have an antinociceptive effect, and it has been reported to potentiate the antinociceptive effect of morphine.

Example 21. Role of GRP+ Fibers

Figure 31C:
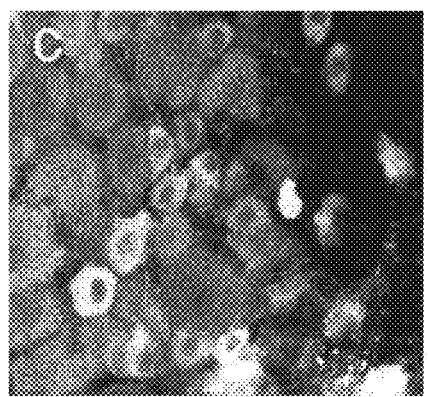
Figure 31D:
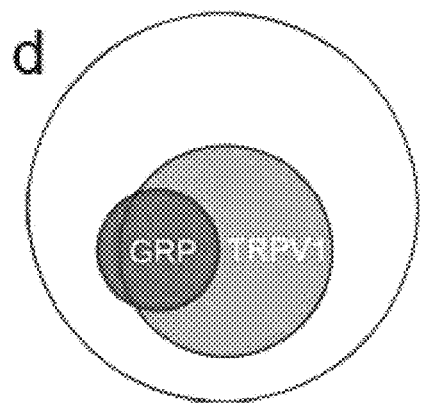
Figure 33A:
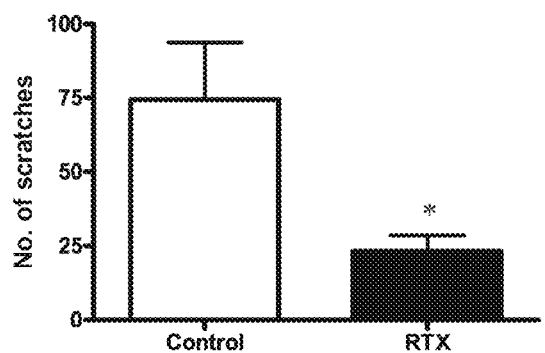
FIG. 33A-C depicts graphs illustrating that morphine-induced scratching behavior is dependent on the peptidergic primary fibers. (A) Morphine induced scratching behavior is significantly reduced after RTX treatment. (B) The motor function tested by accelerating rotarod is comparable between groups. n=5-7, *P<0.05, student's t-test. (C) Tail-flick latency is significantly increased after RTX treatment. ***P<0.001, student's t-test.
Figure 33B:
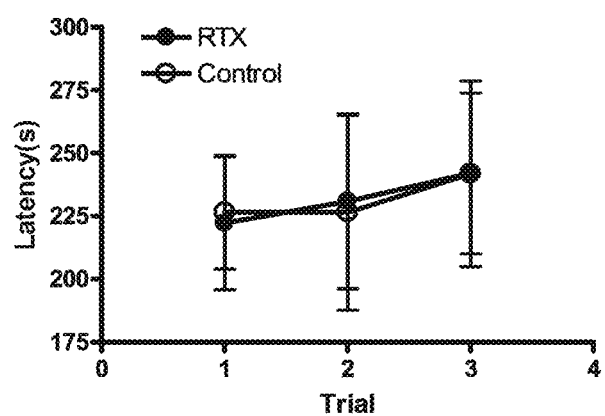
Figure 33C:
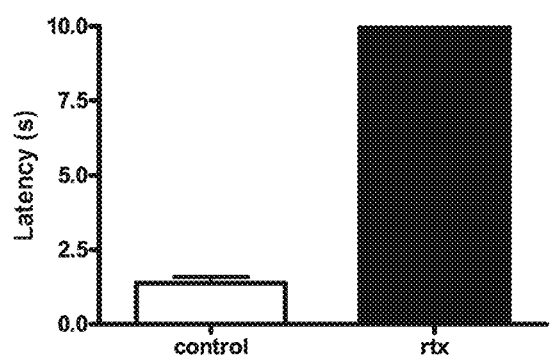

An approximate 80% of GRP+ neurons express TRPV1, a vanilloid receptor important for detecting thermal and chemical stimuli in the DRGs (FIG. 31). To further confirm that morphine-induced scratching behavior is mediated by GRP/GRPR signaling pathway, we depleted GRP+ fibers by intrathecal injection of resiniferatoxin (RTX), which is a potent VR1 vanilloid receptor agonist. Three days after the injection of resiniferatoxin, we found that the peptidergic fiber labeled by CGRP are largely diminished (FIG. 32G, H), TRPV1 signal is almost lost (FIG. 32K, L). The GRP+ fibers are also almost depleted by the RTX treatment (FIG. 32I, J). Non-peptidergic primary fibers labeled by IB4-FITC are normal (FIG. 32C, D). PKCγ which labels the LIIi layer of the spinal cord remains normal (FIG. 32A, B). Morphine-induced scratching behavior is significantly reduced after depletion of GRP fibers compared with the control group (FIG. 33A). Motor function is not affected by the depletion of TRPV1+ primary fibers (FIG. 33B). The defect of morphine-induced scratching behavior is not because of loss of GRPR, since GRPR remains normal after treatment of RTX (FIG. 32E, F).

Example 22. Role of 5-HT Fibers

5-HT fibers have been implicated in numerous animal behaviors and psychiatric disorders. Previously generated Lmx1b (LIM homeobox transcription factor 1β) conditional knock-out mice (CKO, Lmx1b$^{f/f/p}$), in which Lmx1b was only deleted in Pet1 (pheochromocytoma 12 ETS factor-1)-expressing 5-HT neurons, were used to study the role of 5-HT fibers in itch behavior.

Figure 34A:
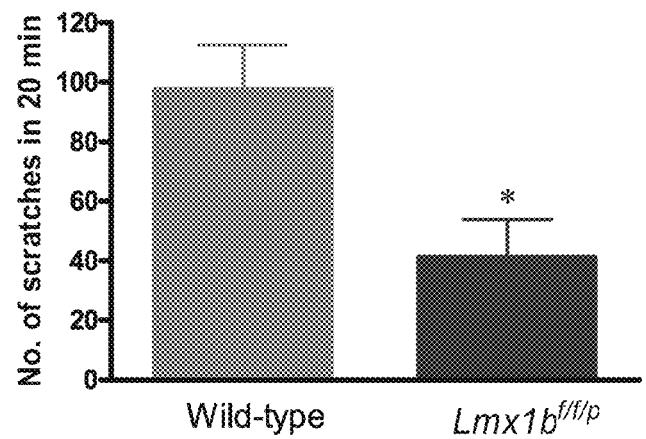
FIG. 34A-B depicts graphs showing that morphine-induced scratching behavior is only partially dependent on 5-HT fibers. (A) $Lmx1b^{f/f/p}$ mice show slightly reduced morphine-induced scratching behavior compared to wild-type mice. *P<0.05, student's t-test. (B) Morphine induced scratching behavior is slightly decreased after administration of 5,7-DHT, compared to saline vehicle. Repeated measures analysis of variance (ANOVA); *P<0.05, n=5-11.
Figure 34B:
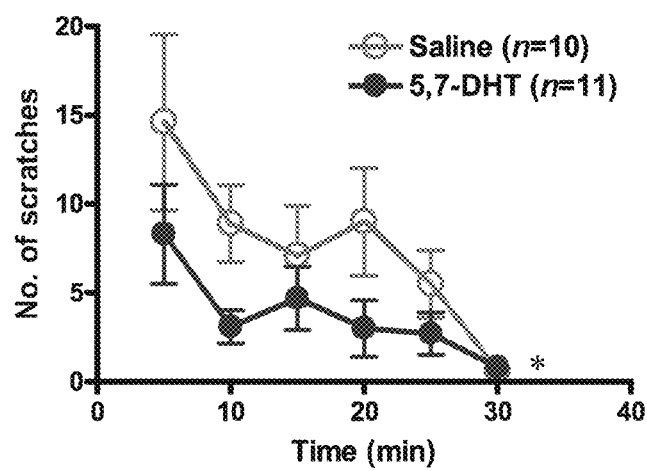

To determine the role of 5-HT fibers in morphine-induced scratching behavior, Lmx1b$^{f/f/p}$ CKO mice and wild-type mice were administered morphine. The scratching behavior was reduced in Lmx1b$^{f/f/p}$ mice, but not eliminated. (FIG. 34A). Similarly, administration of 5,7-DHT reduces, but does not eliminate scratching behavior compared to the administration of saline vehicle. (FIG. 34B). These results are inconclusive regarding the role of 5-HT fibers in morphine-induced itch behavior.

Example 23. Role of Naloxone

Figure 35A:
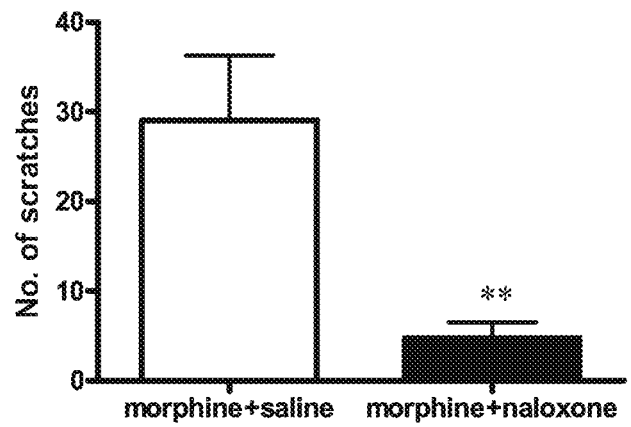
FIG. 35A-B depicts two graphs showing the effect of naloxone on scratching behavior induced by intrathecal morphine. (A) Morphine-induced scratching behavior is significantly reduced by administration of naloxone. *P<0.05, student's t-test. (B) GRP-induced scratching behavior is not significantly affected by administration of naloxone. P>0.05, student's t-test; n=7 for each group.
Figure 35B:
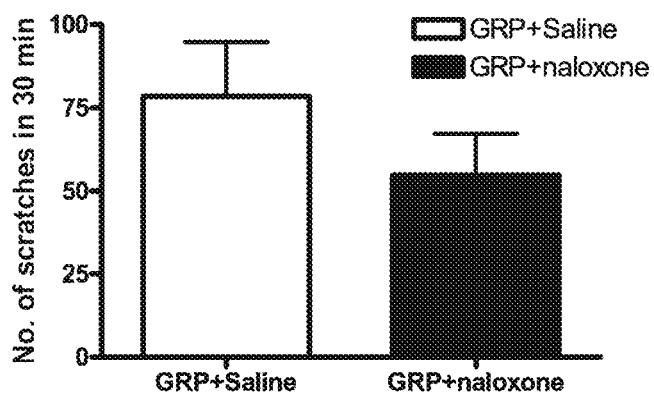

Naloxone is a mu opioid receptor antagonist. When naloxone is administered with morphine, it reduces the morphine-induced scratching behavior. (FIG. 36A) However, naloxone does not reduce the scratching behavior induced by the administration of GRP. (FIG. 35B)

Material and Methods for Examples 18-23

Morphine Induced Scratching Behavior:
Intrathecal injections into the lumbar region of unanesthetized mice were performed as described previously. Morphine (0.1, 0.3, 1.0, 3.0 nmol) or vehicle was injected at a volume of 5 μl, and the number of scratching responses was counted for 20-30 min at 5-min intervals. For the GRPR antagonist (1.0 nmol) or ω-Conotoxin GVIA (10 pmol) experiment, GRPR antagonist or ω-Conotoxin GVIA was injected together with morphine.

Tail-Flick:
A hot water bath is heated to a constant temperature of 52° C. Mice are held loosely in a towel and the lower half of each mouse's tail is dipped into the bath. A timer is stopped immediately when the mouse flicked its tail. To avoid the possibility of tissue damage, a cutoff time of 10 sec is used; if no response occurs by this time, a value of 10 sec is assigned to the experimental subject.

Mechanical Pain:
The animals are placed in a Plexiglas enclosure which rests on an elevated wire mesh grid. This allows the experimenter to probe the hind paws with the series of von Frey filaments (Touch-Test kit, Stoelting, Chicago, Ill.). Each filament was applied 5 consecutive times and the smallest filament that evoked reflexive withdrawal of the paw on at least 3 of the 5 trials was taken as the paw withdrawal threshold.

Rotarod:
The accelerating rotarod test is utilized to assess overall balance and motor coordination. The test is performed on an accelerating rotarod apparatus (Ugo Basile) with a 3 cm diameter rod starting with an initial rotation of 4 rpm and accelerating to 40 rpm over 5 min. Mice are tested 3 times with 15-min intervals.

Resiniferatoxin-Treatment:
Mice were given resiniferatoxin (Sigma, 25 ng/5 ul) or vehicle intrathecally under isoflurane-induced anesthesia. The behavior was tested 3-5 days later.

Analgesia:

For morphine analgesia studies, the tail-flick assay was performed using the 52° C. water tail-immersion approach. The baseline was measured before injection, and then the latency was measured every 15 min for 2 hrs after injection. All tail-flick results were expressed as a percentage of maximum possible effect [% MPE=(post drug latency−pre drug latency)|100/(cutoff time−pre drug latency)].

Data Analysis:

Statistical comparisons were performed with two-way analysis of variance (ANOVA) and Student's t-test. All data were expressed as the mean±standard error of the mean (s.e.m.) and error bars represent s.e.m. $P<0.05$ was considered statistically significant.

Example 24. Overlapping Expression of NMBR and GRPR in Mouse Spinal Cord

Figure 37A:
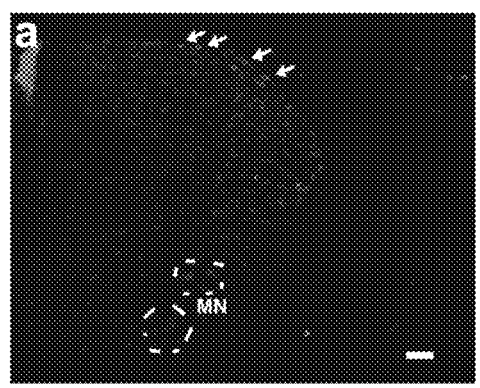
FIG. 37A-C depicts NMBR and GRPR antibody staining in P4 mouse spinal cord. Arrows in (A) and (B), NMBR+ cells in superficial DH; MN, motor neuron area in VH, respectively. Arrow heads in (C), GRPR+ cells in superficial DH. Scale bars in (A) and (C), 50 μm.
Figure 37B:
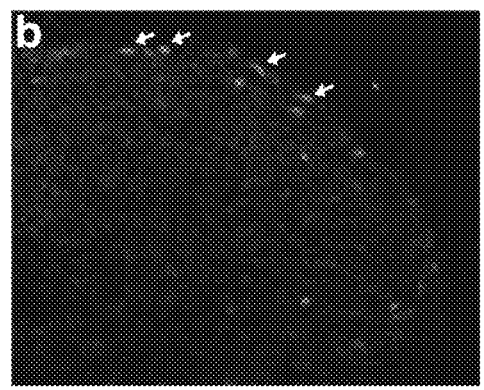
Figure 37C:
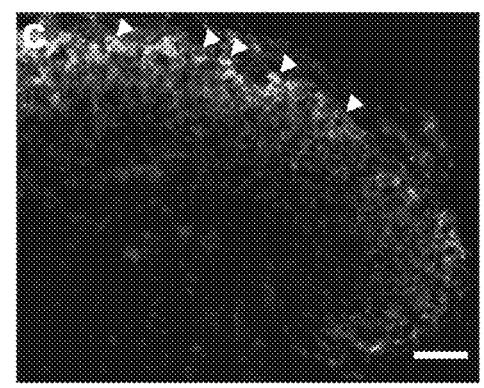
Figure 38A:
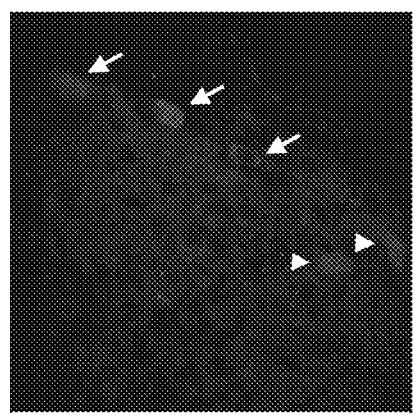
FIG. 38A-C depicts confocal immunofluorescence images showing the overlapping expression of NMBR (red) and GRPR (green) in the dorsal horn of wild-type mice at postnatal stages (P4). From left to right: Arrows, NMBR+ and GRPR+ cells in superficial DH; arrow heads, NMBR+ only cells; asterisks, GRPR+ only cells. Scale bar in (C), 10 μm.
Figure 38B:
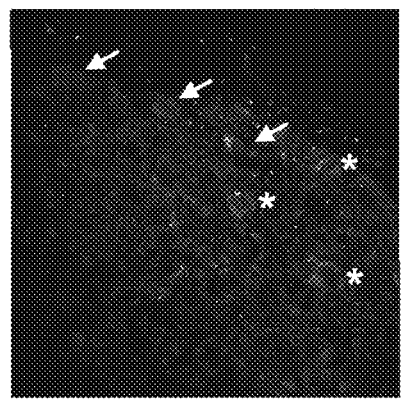
Figure 38C:
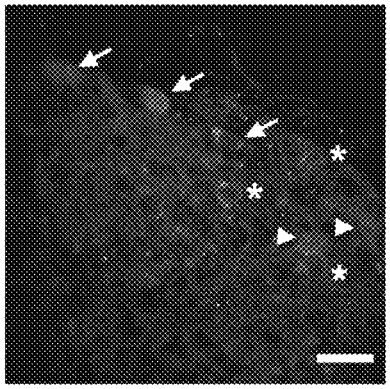
Figure 39A:
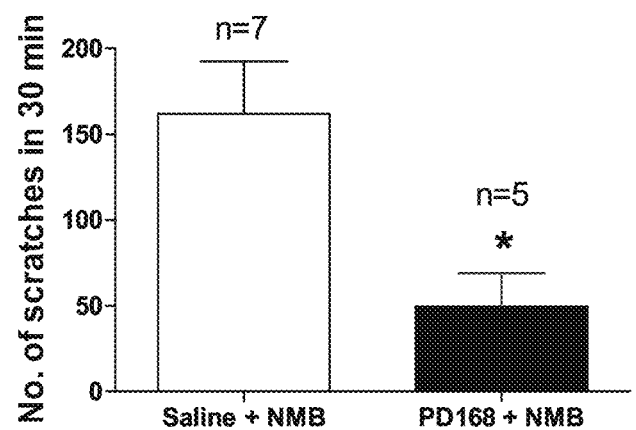
FIG. 39A-B shows that the NMBR antagonist PD168268 inhibits NMB-evoked scratching behavior in wild type mice (males, 8-12 wks). (A) NMB-induced scratching behaviors measured over 30 minutes after injection with 2 nM solution of PD168268. (B) Dose response experiment depicting the NMB-evoked scratching behavior in wild type mice measured over 30 minutes after injection with 1 and 2 nmol of PD168268. PD168268 was injected i.t. into mice at 2 nmol/mouse 10 min before NMB 2 nmol/mouse. p<0.05 (p=0.0184), Student's t-test.
Figure 39B:
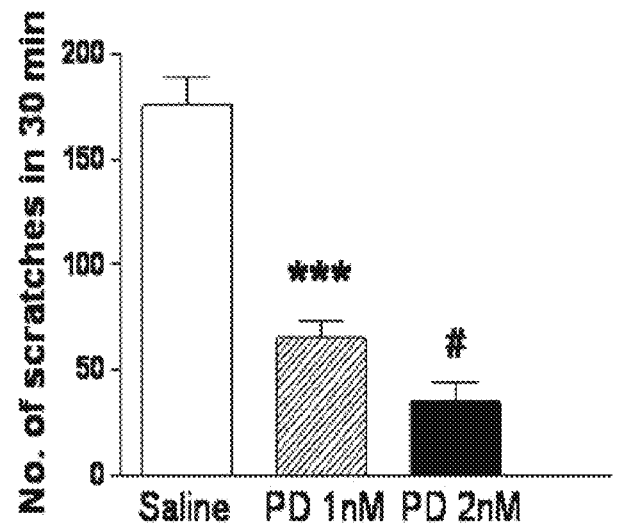

Expression of NMBR and GRPR mRNA in wild type mouse spinal cord was assessed using in-situ hybridization. As shown in FIG. 37, NMBR and GRPR mRNA expression was overlapping. NMBR and GRPR antibody staining and confocal immunofluorescence images in P4 mouse spinal cord also confirm overlapping expression of these receptors (FIGS. 37 and 38).

Goat polyclonal NMBR Antibody was from Santa Cruz Biotechnology, Inc. (NMBR (S-15): sc-34377), diluted at 1:20. Rabbit polyclonal GRPR Antibody was from NIH, diluted as 1:400. For double staining, the NMBR antibody was used at a dilution of 1:20, and visualized using a Cy3 conjugated tyramide signal amplification (TSA) kit. This was followed by staining with the GRPR antibody at a dilution of 1:300, and visualized using a FITC-conjugated secondary antibody.

Figure 40A:
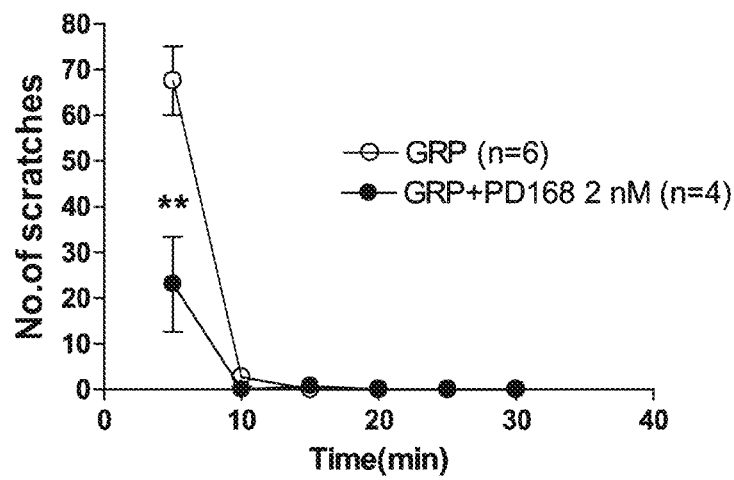
FIG. 40A-B shows that the NMBR antagonist PD168268 inhibits GRP-evoked scratching behavior in wild type mice (males, 8-12 wks). (A) Number of scratches over time. (B) Comparison of cumulative number of scratches of the results shown in (A). PD168268 was injected at 2 nmol/mouse 10 min before GRP 1 nmol/mouse. p<0.01 (p=0.0072), t test, when the data in first 5 min was compared.
Figure 40B:
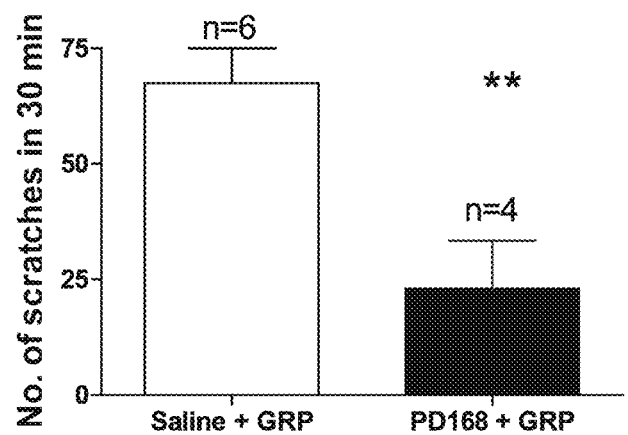
Figure 41A:
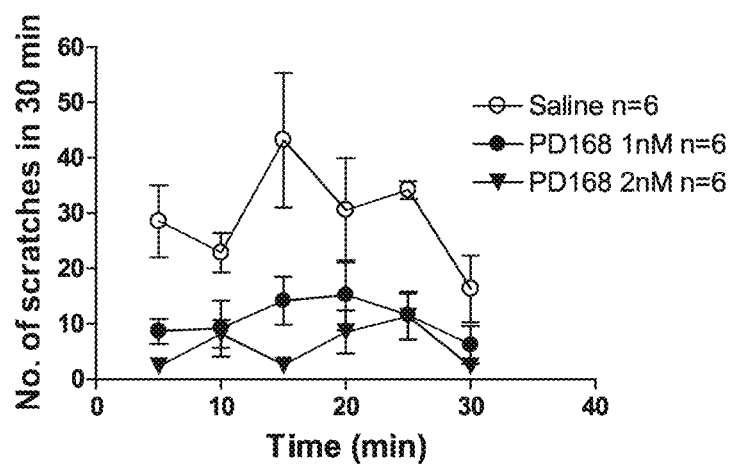
FIG. 41A-B shows that the NMBR antagonist PD168268 inhibits chloroquine-evoked scratching behavior in wild type mice (males, 8-12 wks). (A) Number of scratches over time. (B) Comparison of cumulative number of scratches of the results shown in (A). PD168268 was injected i.t. at 2 nM/mouse 10 min before i.d injection of chloroquine at 200 μg/mouse in 50 μl. ***, P<0.001, compared to vehicle; #, P<0.05, compared to 1 nmol result. One-way ANOVA followed by Newman-Keuls post hoc test.
Figure 41B:
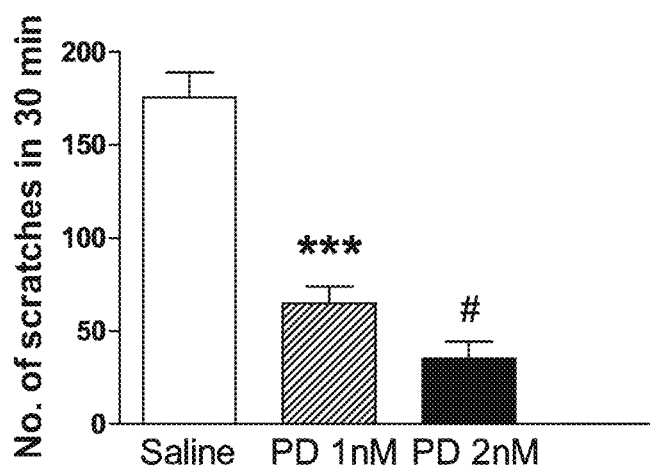

Example 25. NMBR Antagonist PD168268 Inhibits NMB-, GRP-, and Chloroquine-Evoked Scratching The effect of the NMBR antagonist PD168268 against several itch inducers was assessed. As shown in FIG. 40, PD168268 inhibited NMB-induced scratching behaviors. PD168268 also inhibited GRP-induced scratching behaviors (FIG. 40) and chloroquine-induced scratching behaviors (FIG. 41).

The NMBR antagonist, PD168268 (Tocris Bioscience, Cat#2603) was dissolved in DMSO and further diluted by saline prior to i.t. injection at 1 or 2 nM/mouse 10 minutes before injecting 2 nM/mouse of NMB. PD168268 was injected 10 minutes before intradermal (i.d.) injection of 200 µg/mouse of Chloroquine in 50 µL (Sigma).

Example 26. Silencing of NMBR by siRNA Reduces NMB-Induced Scratching

Two siRNAs from Dharmacon were used; siGENOME NMBR siRNA #1 was (cat # D-047820-01), and NMBR siRNA #3 (cat # D-047820-03). The control (mismatch) siRNA was siGENOME Non-Targeting siRNA #2 (cat # D-001210-02-05). All siRNAs were dissolved in RNAse-free water at the concentration of 1 µg/µl stock solution. siRNA was mixed with polyethyleneimine 10 (PEI, Fermentas) 10 min before injection to increase cell membrane penetration and reduce degradation. PEI was dissolved in 5% glucose, and 1 µg of siRNA was mixed with 0.18 µl of PEI. The siRNA was used at 1 ug/ul in 5 ul per mouse intrathecal injection. Reduce levels of spinal NMBR mRNA after siRNA injection was confirmed by Q-RT-PCR.

Figure 42A:
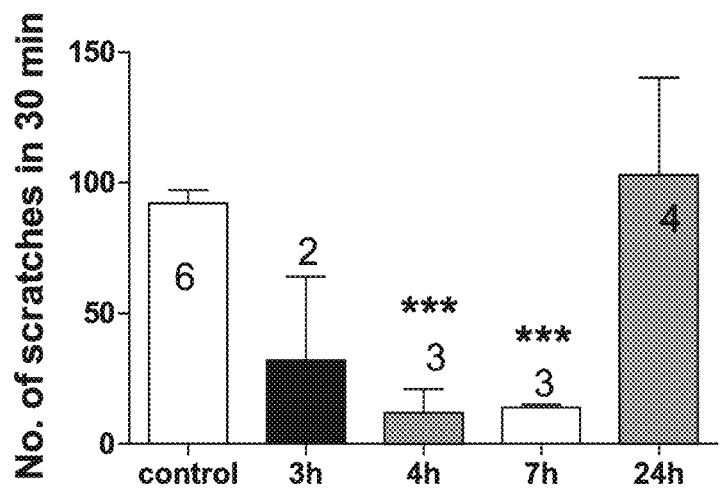
FIG. 42A-B depicts effects of NMBR siRNA #1 (Dharmacon: cat#D-047820-01) on (A) NMB-induced scratching behavior, and (B) chloroquine-induced scratching behavior after intrathecal injection of NMBR siRNA into wild type mice. Time is hours after siRNA injection. Numbers above the bar are animal n number tested. *, P<0.05, ***, P<0.001, student's t-test, compared to control (mismatch, siGENOME Non-Targeting siRNA, from Dharmacon: cat#D-001210-02-05).
Figure 42B:
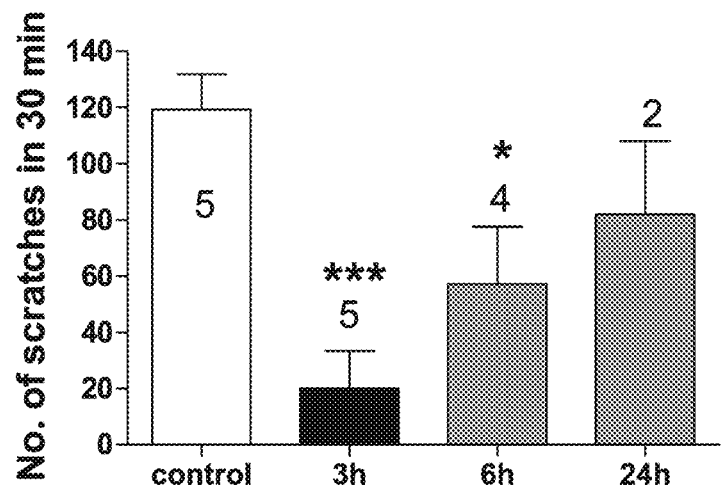

Intrathecal injection of NMBR siRNA #1 reduced the NMB-induced and chloroquine-induced scratching in WT mice (FIG. 42). The reduction in NMB-induced scratching was most significant at 4 and 7 hours after injection, and absent 24 hours after injection. The reduction in chloroquine-induced scratching was most significant at 3 hours after injection, less apparent at 6 hours after injection, and absent 24 hours after injection.

Figure 43:
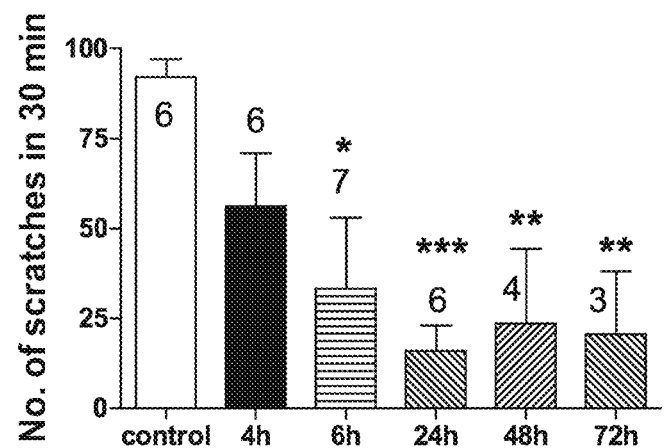
FIG. 43 depicts effects of NMBR siRNA #3 (Dharmacon: cat#D-001210-02-05) on NMB-induced scratching behavior after intrathecal injection of NMBR siRNA into wild type mice. Time is hours after siRNA injection. Numbers above the bar are animal n number tested. *, P<0.05, , P<0.01, *, P<0.001, student's t-test, compared to control (mismatch, siGENOME Non-Targeting siRNA, from Dharmacon: cat#D-001210-02-05).

Intrathecal injection of NMBR siRNA #3 reduced the NMB-induced scratching in WT mice (FIG. 43). The reduction in NMB-induced scratching was most significant at 24 after injection, with the reduction persisting 48 and 72 hours after injection.

Example 27. Itch and Pain Phenotypes of NMBR/GRPR Double Knockout Mice

Figure 44:
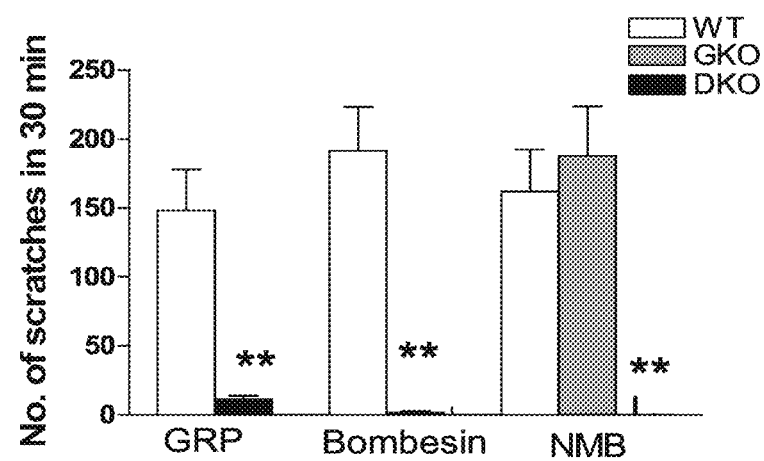
FIG. 44 depicts the itch behavior of NMBR/GRPR double knockout mice in response to 3 different bombesin-like peptides. GRP 1 nmol, Bombesin 0.05 nmol, NMB 2 nmol, all given by intrathecal administration, n=4~7. **, p<0.01, t test, compared to WT in the same treatment. GKO, GRPR mutant mice; DKO, NMBR/GRPR double KO mice.
Figure 45A:
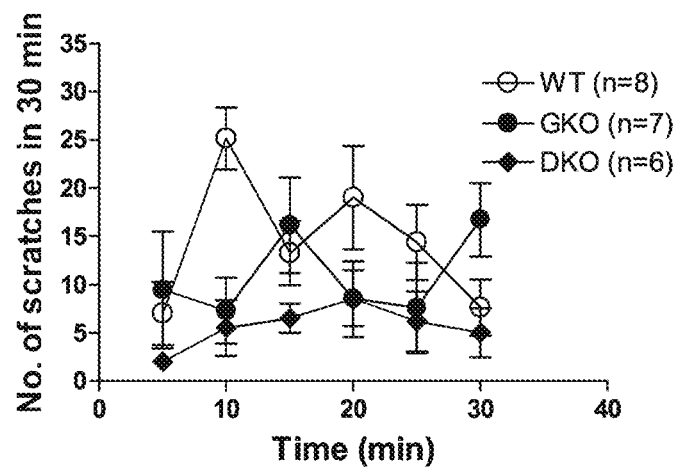
FIG. 45A-J depicts the itch phenotypes of NMBR/GRPR double knockout mice in response to histamine (A, B), compound 48/80 (C, D), ET-1 (E, F), chloroquine (G, H), and 5-HT (I, J). (A), (C), (E), (G) and (I) are time course curve, while (B), (D), (F), (H) and (J) represent the total value comparisons from the same experiment. *p<0.05, **p<0.01; One-way ANOVA followed by Newman-Keuls post hoc test was used in all statistical analysis.
Figure 45B:
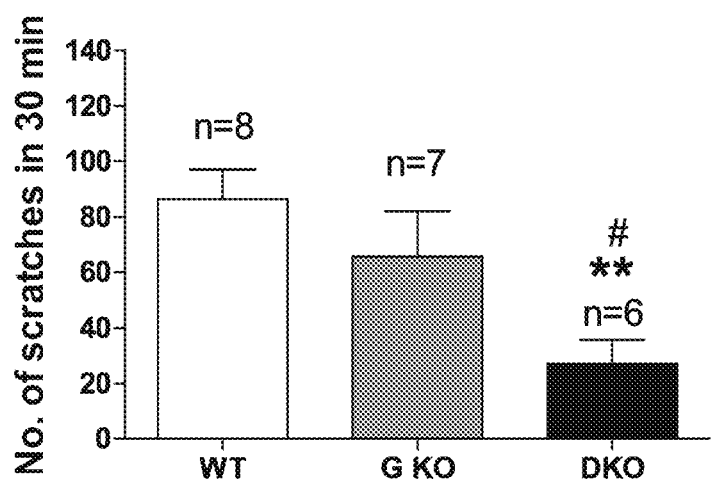
Figure 45C:
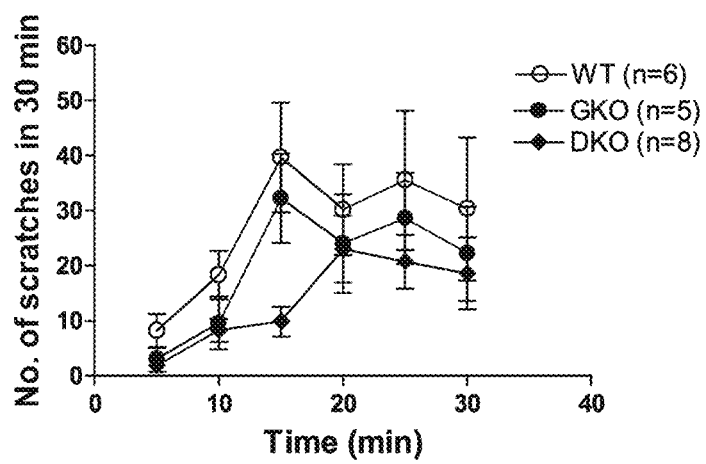
Figure 45D:
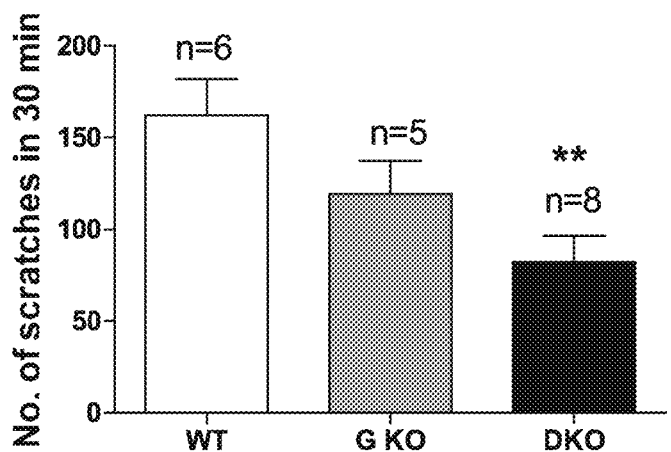
Figure 45E:
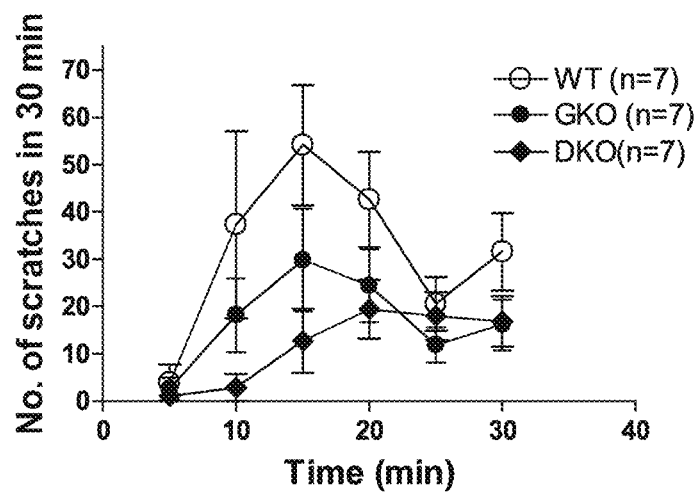
Figure 45F:
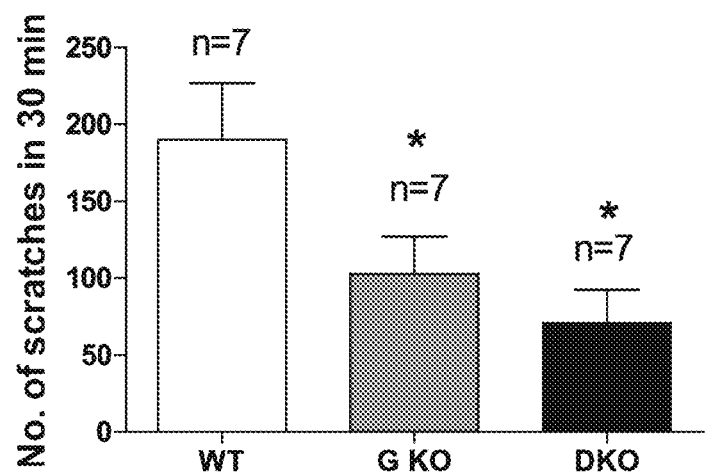
Figure 45G:
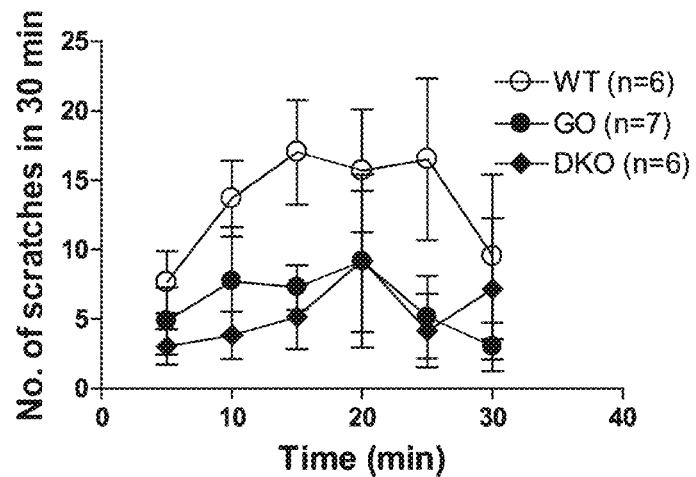
Figure 45H:
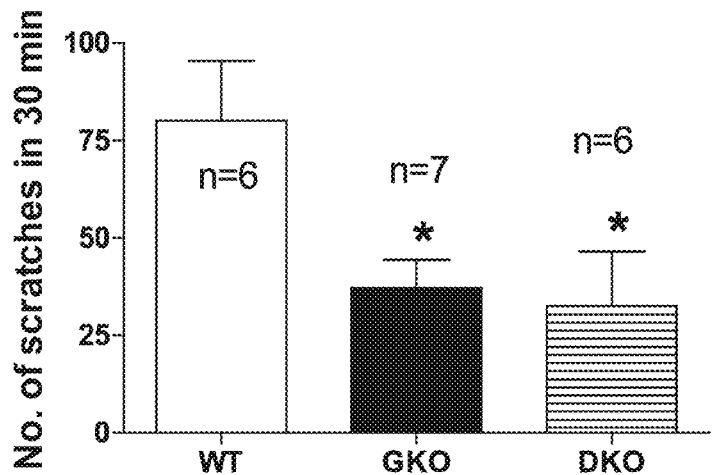
Figure 45I:
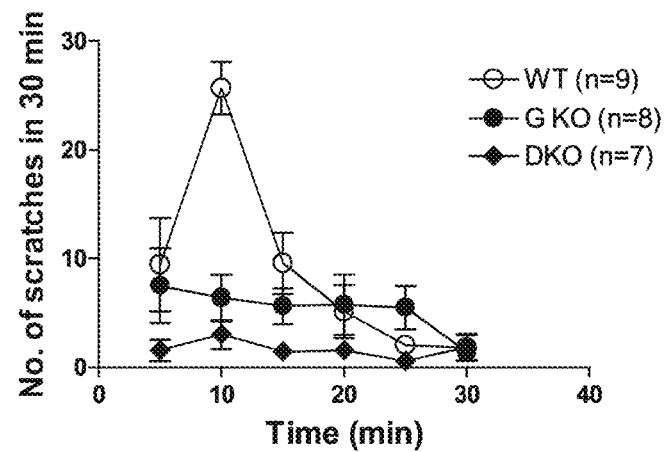
Figure 45J:
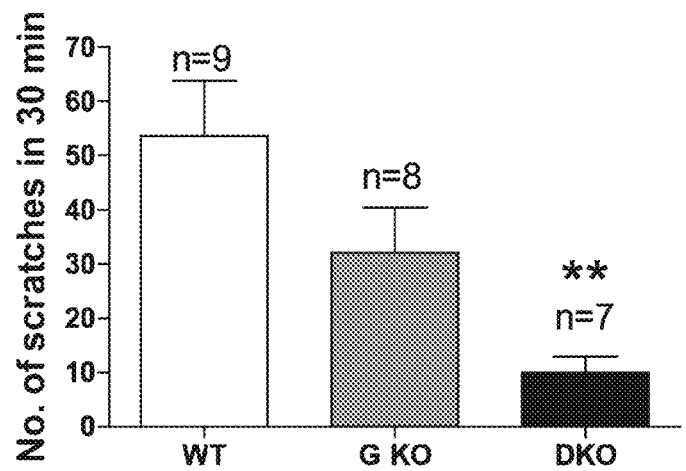
Figure 46A:
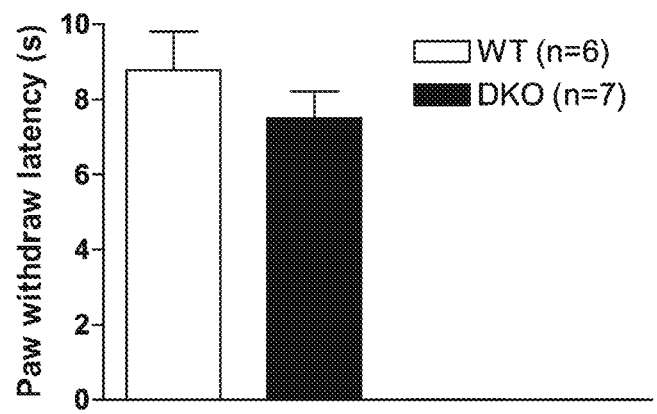
FIG. 46A-E depicts acute pain tests and rotarod test on wild type and GRPR/NMBR double knockout (DKO) mice. (A-C) Acute thermal, (D mechanical and (E) motor function evaluated by the rotarod.
Figure 46B:
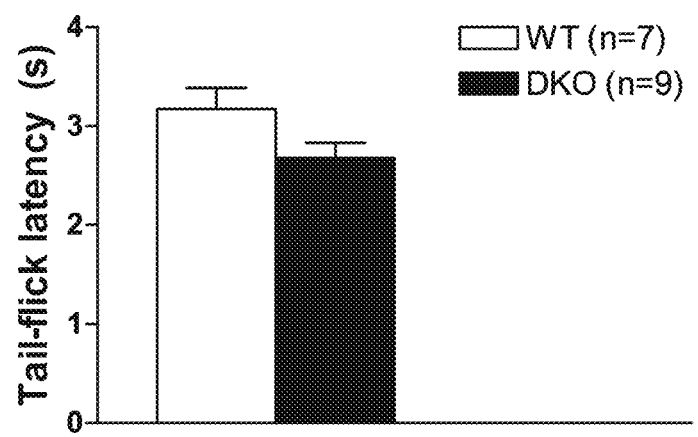
Figure 46C:
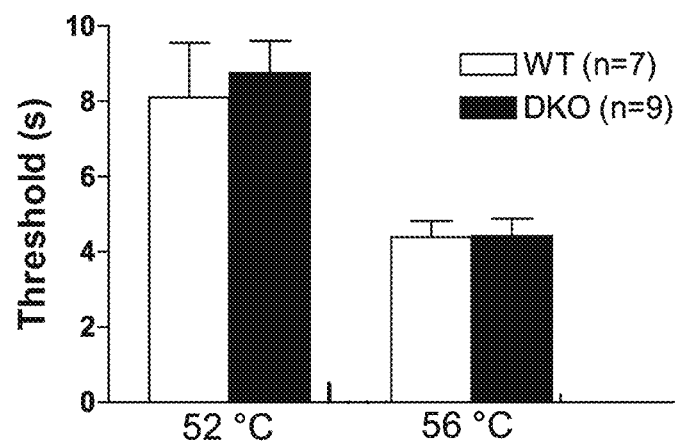
Figure 46D:
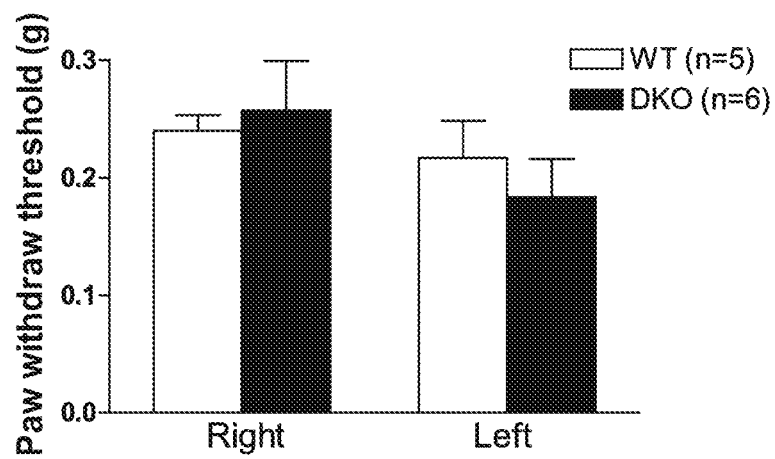
Figure 46E:
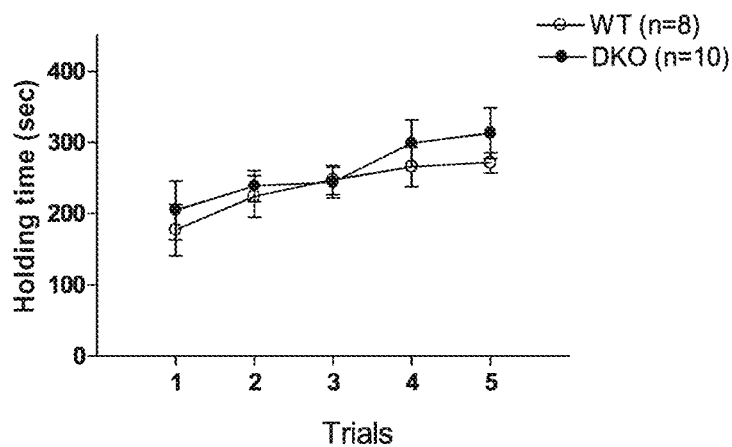
Figure 47:
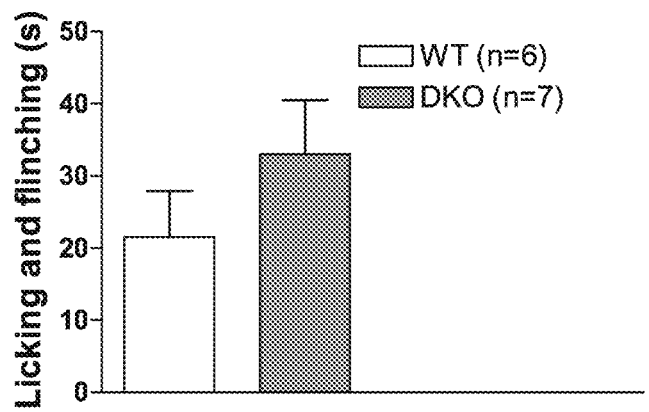
FIG. 47 depicts spontaneous pain behavior (licking and flinching to the injected hindpaw) in the first 10 min after 1 ug/10 ul Capsaicin (sigma) intraplantar injection. There is no significant difference of their response to capsaicin.
Figure 48:
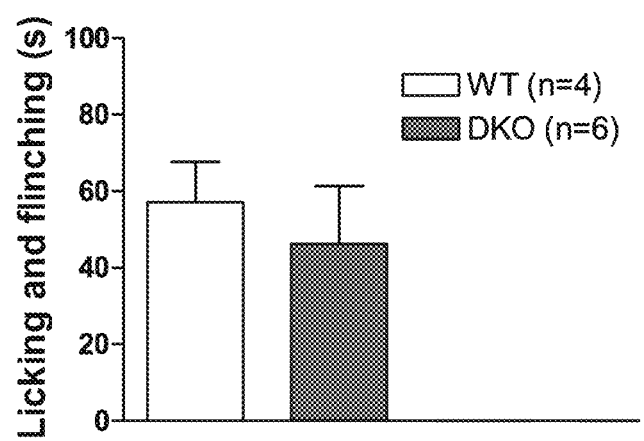
FIG. 48 depicts spontaneous pain behavior (licking and flinching to the injected hindpaw) in the first 10 min after 0.25% mustard oil (sigma, in light mineral oil, 10 ul/mouse) intraplantar injection. WT and DKO response similarly.
Figure 49A:
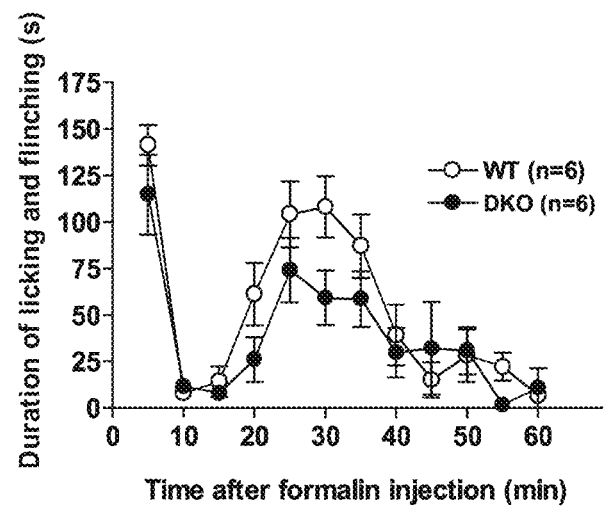
FIG. 49A-B depicts spontaneous pain behavior (licking and flinching to the injected hindpaw) after 5% Formalin intraplantar injection. (A) Spontaneous pain behavior in the first 60 min after 5% Formalin (sigma, 10 μl in saline) intraplantar injection is depicted. (B) Data from (A) is depicted as two phases. There is no difference in the first phase (0-10 min), and in the second phase (10-60 min) between DKO mice and WT mice. DKO mice show a slightly but not statistically significant decrease in pain behavior.
Figure 49B:
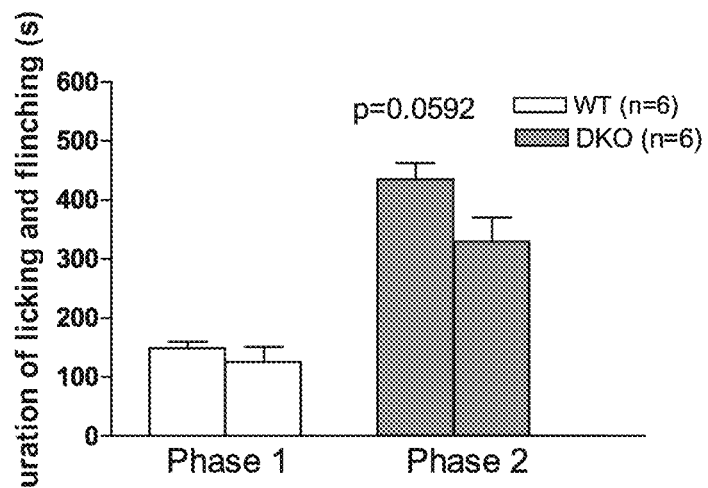
Figure 50A:
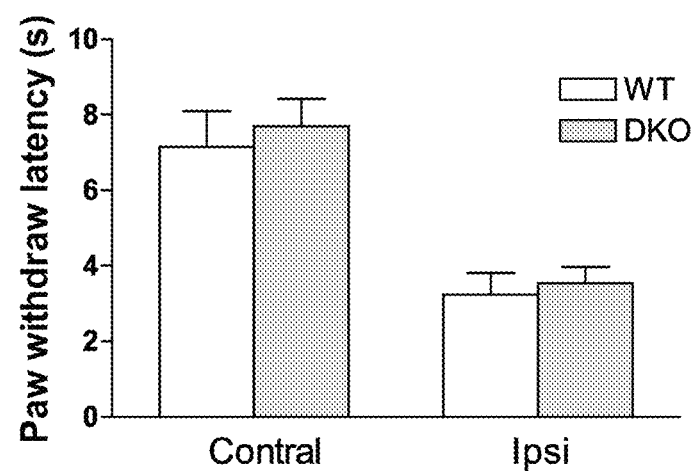
FIG. 50A-B depicts the inflammatory pain behavior 24 hours after injecting 20 μl of 50% complete form adjuvant (CFA, Sigma) in saline into the right hind paw intraplantar region. The wild type and NMBR/GRPR double knockout (DKO) mice showed similar thermal (A) and mechanical (B) hyperalgesia after inflammation.
Figure 50B:
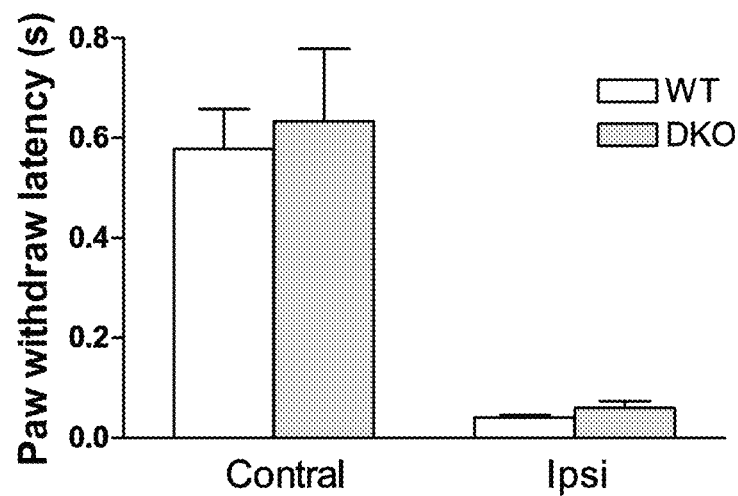

NMBR/GRPR double knockout mice exhibit deficits in response to 3 different bombesin-like peptides: GRP (1 nM), Bombesin (0.05 nM), and NMB (2 nM), all given by intrathecal administration (FIG. 44). In addition, NMBR/GRPR double knockout mice exhibit deficits in response to histamine (FIGS. 45 A and B), or the histamine-inducing compound 48/80 (FIGS. 45 C and D), ET-1 (FIGS. 45 E and F), chloroquine (FIGS. 45 G and H) and serotonin (5-HT) (FIGS. 45 I and J). Histamine was injected i.d. in 50 µl at 20 µg/mouse. Compound 48/80 was injected i.d. in 50 µl at 20 µg/mouse. ET-1 was injected i.d. in 50 µl at 1 ng/mouse. Chloroquine was injected i.d. in 50 µl at 4 µg/mouse. Serotonin (5-HT) was injected i.d. in 50 µl at 1 1 nmol/µl.

Conversely, acute, spontaneous and inflammatory pain behavior was similar between NMBR/GRPR double knockout mice and wild type mice (FIGS. 46-50).

REFERENCES

Bhattacherjee V, Mukhopadhyay P, Singh S, Roberts E A, Hackmiller R C, Greene R M, Pisano M M (2004) Laser capture microdissection of fluorescently labeled embryonic cranial neural crest cells. Genesis 39:58-64.

Birren S J, Lo L, Anderson D J (1993) Sympathetic neuroblasts undergo a developmental switch in trophic dependence. Development 119:597-610.

Buys L M (2007) Treatment options for atopic dermatitis. Am Fam Physician 75:523-528.

Carroll C L, Balkrishnan R, Feldman S R, Fleischer A B, Jr., Manuel J C (2005) The burden of atopic dermatitis: impact on the patient, family, and society. Pediatr Dermatol 22:192-199.

Davidson S, Zhang X, Yoon C H, Khasabov S G, Simone D A, Giesler G J, Jr. (2007) The itch-producing agents histamine and cowhage activate separate populations of primate spinothalamic tract neurons. J Neurosci 27:10007-10014.

Flohr C, Johansson S G, Wahlgren C F, Williams H (2004) How atopic is atopic dermatitis? J Allergy Clin Immunol 114:150-158.

Gong S, Zheng C, Doughty M L, Losos K, Didkovsky N, Schambra U B, Nowak N J, Joyner A, Leblanc G, Hatten M E, Heintz N (2003) A gene expression atlas of the central nervous system based on bacterial artificial chromosomes. Nature 425:917-925.

Green A D, Young K K, Lehto S G, Smith S B, Mogil J S (2006) Influence of genotype, dose and sex on pruritogen-induced scratching behavior in the mouse. Pain 124:50-58.

Ikoma A, Steinhoff M, Stander S, Yosipovitch G, Schmelz M (2006) The neurobiology of itch. Nat